US009175338B2

(12) United States Patent
Flusberg et al.

(10) Patent No.: US 9,175,338 B2
(45) Date of Patent: *Nov. 3, 2015

(54) METHODS FOR IDENTIFYING NUCLEIC ACID MODIFICATIONS

(75) Inventors: Benjamin Flusberg, Atlanta, GA (US); Jonas Korlach, Newark, CA (US); Jeffrey Wegener, Cupertino, CA (US); Tyson A. Clark, Menlo Park, CA (US); Igor Vilfan, East Palo Alto, CA (US); Andrey Kislyuk, San Ramon, CA (US); Stephen Turner, Menlo Park, CA (US); Jon Sorenson, Alameda, CA (US); Kevin Travers, Menlo Park, CA (US); Cheryl Heiner, San Mateo, CA (US); Austin B. Tomaney, Burlingame, CA (US); Patrick Marks, San Francisco, CA (US); Jessica Lee, Cupertino, CA (US); Lei Jia, Palo Alto, CA (US); Dale Webster, San Mateo, CA (US); John Lyle, Redwood Shores, CA (US); Jeremiah Hanes, Redwood City, CA (US); Joseph Puglisi, Stanford, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/945,767

(22) Filed: Nov. 12, 2010

(65) Prior Publication Data

US 2011/0183320 A1 Jul. 28, 2011

Related U.S. Application Data

(63) Continuation-in-part of application No. 12/635,618, filed on Dec. 10, 2009.

(60) Provisional application No. 61/201,551, filed on Dec. 11, 2008, provisional application No. 61/180,350, filed on May 21, 2009, provisional application No. 61/186,661, filed on Jun. 12, 2009.

(51) Int. Cl.
*C12Q 1/68* (2006.01)

(52) U.S. Cl.
CPC ............ *C12Q 1/6858* (2013.01); *C12Q 1/6837* (2013.01); *C12Q 1/6869* (2013.01)

(58) Field of Classification Search
None
See application file for complete search history.

(56) References Cited

U.S. PATENT DOCUMENTS

| | | | |
|---|---|---|---|
| 5,547,839 A | 8/1996 | Dower et al. | |
| 6,210,896 B1 | 4/2001 | Chan | |
| 6,235,502 B1 | 5/2001 | Weissman et al. | |
| 6,255,083 B1 | 7/2001 | Williams | |
| 6,555,311 B1 | 4/2003 | Locarnini et al. | |
| 6,787,308 B2 | 9/2004 | Balasubramanian et al. | |
| 7,056,661 B2 | 6/2006 | Korlach et al. | |
| 7,399,614 B2 | 7/2008 | Zon | |
| 7,459,274 B2 | 12/2008 | Lakey et al. | |
| 7,611,869 B2 | 11/2009 | Fan | |
| 8,137,937 B2 | 3/2012 | Markert-Hahn | |
| 8,153,375 B2 | 4/2012 | Travers et al. | |
| 8,486,634 B2 | 7/2013 | Lim et al. | |
| 2002/0102577 A1 | 8/2002 | Raillard et al. | |
| 2003/0096253 A1 | 5/2003 | Nelson et al. | |
| 2003/0190647 A1 | 10/2003 | Odera | |
| 2003/0215862 A1 | 11/2003 | Parce et al. | |
| 2004/0048300 A1 | 3/2004 | Sood et al. | |
| 2004/0152119 A1 | 8/2004 | Sood et al. | |
| 2004/0224319 A1 | 11/2004 | Sood et al. | |
| 2005/0053937 A1 | 3/2005 | Berlin | |
| 2005/0208538 A1 | 9/2005 | Kurn et al. | |
| 2005/0214812 A1 | 9/2005 | Li et al. | |
| 2005/0239085 A1 | 10/2005 | Buzby et al. | |
| 2006/0024676 A1 | 2/2006 | Uhlmann et al. | |
| 2006/0063264 A1 | 3/2006 | Turner et al. | |
| 2007/0020640 A1 | 1/2007 | McCloskey et al. | |
| 2008/0207460 A1 | 8/2008 | Gormley | |
| 2009/0012282 A1 | 1/2009 | Zon | |
| 2009/0024331 A1 | 1/2009 | Tomaney et al. | |
| 2009/0269771 A1 | 10/2009 | Schroeder | |
| 2009/0280538 A1 | 11/2009 | Patel et al. | |
| 2010/0041057 A1 | 2/2010 | Dong et al. | |
| 2010/0121582 A1 | 5/2010 | Pan et al. | |

(Continued)

FOREIGN PATENT DOCUMENTS

| | | | |
|---|---|---|---|
| WO | 9106078 A1 | 5/1991 | |
| WO | 9627025 A1 | 9/1996 | |

(Continued)

OTHER PUBLICATIONS

Colasanti, et al., "Cytosine Methylated DNA Synthesized by Taq Polymerase Used to Assay Methylation Sensitivity of Restriction Endonuclease Hinfl." Nucleic Acids Research (1991) 19(2):391-394.

Ludlum, et al., "Ribonucleic Acid Polymerase Reactions with Methylated Polycytidylic Acid Templates," Journal of Biological Chemistry (1968) 243(10):2750-2753.

Tost, et al., "DNA Methylation Analysis by Pyrosequencing," Nature Protocols (2007) 2(9):2265-2275.

(Continued)

*Primary Examiner* — Angela M Bertagna
(74) *Attorney, Agent, or Firm* — Deana A. Arnold

(57) ABSTRACT

Methods, compositions, and systems are provided for characterization of modified nucleic acids. In certain preferred embodiments, single molecule sequencing methods are provided for identification of modified nucleotides within nucleic acid sequences. Modifications detectable by the methods provided herein include chemically modified bases, enzymatically modified bases, abasic sites, non-natural bases, secondary structures, and agents bound to a template nucleic acid.

15 Claims, 28 Drawing Sheets

(56) References Cited

U.S. PATENT DOCUMENTS

| | | | |
|---|---|---|---|
| 2010/0190175 | A1 | 7/2010 | Gerard et al. |
| 2010/0221716 | A1* | 9/2010 | Flusberg et al. .................. 435/6 |
| 2010/0255487 | A1 | 10/2010 | Beechem et al. |
| 2011/0104787 | A1 | 5/2011 | Church et al. |
| 2011/0201524 | A1 | 8/2011 | Kester |
| 2011/0236894 | A1* | 9/2011 | Rao et al. ..................... 435/6.11 |
| 2011/0237444 | A1 | 9/2011 | Clancy et al. |
| 2012/0329042 | A1 | 12/2012 | Beechem et al. |

FOREIGN PATENT DOCUMENTS

| | | |
|---|---|---|
| WO | 9703210 A1 | 1/1997 |
| WO | 9905315 A2 | 2/1999 |
| WO | 2006005064 A2 | 1/2006 |
| WO | 2007068437 A1 | 6/2007 |
| WO | 2010068289 A2 | 6/2010 |
| WO | 2010003153 A2 | 7/2010 |

OTHER PUBLICATIONS

International Preliminary Report on Patentability dated Jun. 23, 2011 for corresponding PCT application PCT/US2009/006517.
EP Search Report dated May 16, 2012 for related case EP 9832251.4.
Meissner, A. et al, "Genome-scale DNA methylation maps of pluripotents and differentiated cells" Nature (2008) 454:786-770 (+ supplementary information ).
Merino, E.J. et al. "RNA Structure Analysis at Single Nucleotide Resolution by Selective 2'-Hydroxyl Acylation and Primer Extension (SHAPE)" J Am Chem Soc (2005) 127:4223-4231.
Morgan, H.D. et al. "Activation-induced cytidine deaminase aminates 5-methylcytosine in DNA and is expressed in pluripotent tissues" J Biol Chem (2004) 279:52353-52360.
Morozova, O. et al. "Applications of next generation sequencing technologies in functional genomics" Genomics (2008) 92:255-264.
Narayan, P. et al. "Unequal Distribution of N6-Methyladenosine in Influenza Virus RNAs" Mol Cell Biol (1987) 7(4):1572-1575.
Ohki, I et al. "Solution structures of the methyl-CpG-binding domain of the methylation-dependent transcriptional repressor MBD1" EMBO J (2000) 18(23):6653-6661.
Ohmori, "The Y-Family of DNA Polymerases" et al. Mol Cell (2001) 8(1):7-8.
Okamoto, A. "5-Methylcytosine-Selective Osmium Oxidation" Nucleosides, Nucleotides, Nucleic Acids (2007) 26(10-12):1601-1604.
Petrov, A.I. et al. "Spin-labeled polyribonucleotids" Nucl Acids Res (1980) 8(18):4221-4234.
Radicella. J.P. et al. "Cloning and characterization of hOGG1, a human homolog of the OGG1 gene of Saccharomyces cerevisiae" PNAS (1997) 94:8010-8015.
Rollins, R.A, et al. "Large-scale structure of genomic methylation patterns" Genome Res (2006) 16-157-163.
Sadri, R. et al. "Rapid analysis of DNA methylation using new restriction enzyme sites created by bisulfite modification" Nucl Acids Res (1996) 24(24):5058-5059.
Seo, Y.J. et al. "Optimization of an Unnatural Base Pair toward Natural-Like Replication" J Am Chem Soc (2009) 131-3246-3252.
Smith, S.S. et al. "Mechanism of human methyl-directed DNA methyltransferase and the fidelity of cytosine methylation" PNAS (1992) 89:4744-4748.
Smolina, I.V. et al. "Pausing of DNA Polymerases on Duplex DNA Templates due for Ligand Binding in Vitro" J Mol Biol (2003) 326:1113-1125.
Tahiliani, M. et al. "Conversion of 5-methylcytosine to 5-Hydroxymethytcytosine in Mammalian DNA by MLL Partner TET1" Science (2009) 324(5929):930-935.
Tahiliani, M. et al. "Supporting Online Material for Conversion of 5-Methylcytosine to 5-Hydroxymethylcytosine in Mammalian DNA by MLL Partner TET1" Science (2009) 324(5929):930-935.
Tanaka, K. et al. "Direct Labeling of 5-Methylcytosine and its Applications" J Am Chem Soc (2007) 129(17):5612-5620.

Tijerina, P. et al. "DMS Footprinting of Structured RNAs and RNA-Protein Complexes" Nature Protocols (2007) 2:2608-2623.
Vidal, A.E. et al. "Mechanism of stimulation of the DNA glycosylase activity of hOGG1 by the major human AP endonuclease: bypass of the AP lyase activity step" Nucl Acids Res (2001) 29(6):1285-1292.
Viguera, E. et al. "Replication slippage involves DNA polymerase pausing and dissociation" EMBO J (2001) 20(10):2587-2595.
Weber, J. et al. "Chromosome-wide and Promoter-specific analyses identify sites of differential DNA methylation in normal and transformed human cells" Nat Genet (2005) 37:853-862.
Yebra, M.J. et al. "A Cytosine Methyltransferase Converts 5-Methylcytosine in DNA to Thymine" Biochemistry (1995) 34(45):14752-14757.
Zheng, K-W. et al. "Molecular crowding creates an essential environment for the formation of stable G-quadruplexes in long double-stranded DNA" Nucl Acids Res (2010) 38(1):327-338.
ISR and Written Opinion issued Aug. 25, 2010 for corresponding PCT application PCT/US2009/006517.
Ahle, J.D. et al. "Sequence determination of nucleic acids containing 5-methylisceytosine and isoguanine: identification and insight into polymerase replication of the non-natural nucleobases" Nucl Acids Res (2005) 33 (10):3176-3184.
Ananiev, G.E. et al. "Optical mapping discerns genome wide DNA methylation profiles" BMC Mol Biol (2008) 9:68.
Avvakumov, G.V. et al. "Structural bases for recognition of hemi-methylated DNA by the SRA domain of human UHRF1" Nature (2008) 455(7214):822-825.
Banerjee, A. et al. "Structure of a repair enzye interrogating undamaged DNA elucidates recognition of damaged DNA" Nature (2005) 434(7033:612-618.
Bareyt, S. et al. "Selective Detection of 5-Methylcytosine Sites in DNA" Angew Chem Int Ed Engl (2008) 47(1):181-184.
Berman, AJ. et al. "Structures of phi29 DNA polymerase complexed with substrate: the mechanism of translocation in B-family polymerases" EMBO J (2007) 26:3494-3505.
Blainey, P.C. et al. "A base-excision DNA-repair protein finds intrahelical leesion bases by fast sliding in contact with DNA" PNAS (2006) 103(15):5752-5757.
Braun, J.V. et al. "Statistical Methods for DNA Sequence Segmentation" Statist Sci (1998) 13(2):142-162.
Brewer, A.C. et al. "A simplified method for in vivo footprinting using DMS" Nucl Acids Res (1990) 18:5574.
Brunner, A.L. et al. "Distinct DNA methylation patterns characterize differentiated human embryonic stem cells and developing human fetal liver" Genome Res (2009) 19:1044-1056.
Cordonnier, A.M. et al. "Impaired translesion synthesisin Xeroderma Pigmentosurn variant extracts" Mol Cell Biol (1999) 19(3):2206-2211.
Eid, J. et al. "Real-time DNA Sequencing from Single Polymerase Molecules" Science (2009) 323:133-138.
Everts "RNA's Outfits" The nucleic acid has dozens of chemical costumes C&EN (2009) 87:36:65-68.
Fellers, J.P. "Genome Filtering Using Methyiation-Sensitive Restriction Enzymes with Six Base Pair Recognition Sites" Plant Genome (2008) 1(2):146-152.
Finkel, T. et al. "Oxidants, oxidative stress and the biology of ageing" Nature (2000) 408(6809:239-247.
Flusberg, B.A. et al, "Direct detection of DNA methylation during single-molecule, real-time sequencing" Nat Meth (2010) 7(6):461-467.
Friedberg, E.C. "Suffering in Silence: The Tolerance of DNA Damage" Nat Rev Mol Cell Biol (2005) 6(12):943-953.
Fromme, J.C. et al. "Base Excision Repair" Adv Protein Chem (2004) 69:1-41.
Hafner, M. et al. "Transcriptome-wide identification of RNA-binding protein and microRNA target sites by PAR-CLIP" Cell (2010) 141(1):129-141.
Hamm, M.L. et al. "Substrate Specificity of Fpg (MutM) and hOGG1, Two Repair Glycosylasas" J Am Chem Soc. (2007) 129(25):7724-7725.
Hanes, J.W. et al. "Incorporation and replication of 8-oxo-deoxyguanosine by the human mitochondrial DNA polymerase" J Biol Chem (2008) 281(47):36241-36248.

(56) References Cited

OTHER PUBLICATIONS

Hashimoto, H. et al, "The SRA domain of UHRF1 flips 5-methylcytosine out of the DNA helix" Nature (2008) 455(7214):826-829.
Hayatsu, H. "The bisulfite genomic sequencing used in the analysis of epigenetic states, a technique in the emerging environmental genotoxicology research" Mutation Res (2008) 659(1-2):77-82.
Hendrick, B, et al. "Identification and Characterization of a Family of Main talian Methyl-CpG Binding Proteins" Mol Cell Biol (1998) 18(11):6538-6547.
Herbert, K.M. et al. "Single-Molecule Studies of RNA Polymerase: Motoring Along" Ann Rev Biochem (2008) 77:149-176.
Holmquist et al. "The bypass of DNA lesions by DNA and RNA polymerases" Mutat Res (2002) 510(1-2):1-7.
Horowitz, S. at al "Mapping of N6-methyladenosine residues in bovine prolactin mRNA" PNAS (1984) 81(18):5667-5671.
Hsu, G.W, et al. "Error-prone replicatin of oxidatively damaged DNA by a high-fidelity DNA polymerase" Nature (2004) 431(7005:217-221.
Huang, T. H-M et al. "Identification of DNA Methylation Markers for Human Breast Carcinomas Using the Methylation-sensitive Restriction Fingerprinting Technique" Cancer Res (1997) 57:1030-1034.
Ingolia, N.T. et al. "Genome-Wide Analysis in Vivo of Translation with Nucleotide Resolution Using Ribosome Profiling" Science (2009) 324(5924):218-223.
Jones, P.A. et al. "Cancer epigenetics comes of age" Nat Genet (1999) 21(2):163-167.
Jorgensen, H.F, et al. "Engineering a high-affinity methyl-CpG-binding protein" Nucl Acids Res (2006) 34(13):e96.
Kannouche, P. et al, Ubiquitination of PCNA and the Polymerase Switch in Human Cells Cell Cycle (2004) 3(8):1011-1013.
Kannouche, P.L. et al. "Interaction of Human DNA Polymerase r with Monoubiquitinated PCNA: A Possible Mechanism for the Polymerase Switch in Response to DNA Damage" Mol Cell (2004) 14(4):491-500.
Kilgore, J.A. et al. "Single-molecule and population probing of chromatin structure using DNA methyltransferases" Methods (2007)41:320-332.
Klungland, A. et al. "Oxidative damage to purities in DNA: Role of Mammalian Ogg1" DNA Repair (Amst) (2007) 6(4):481-488.
Kriaucionis, S. at al. "The Nuclear DNA Base 5-Hydroxymethylcytosine is Present in Purkinje Neurons and the Brain" Science (2009) 324(5929) :929-930.
Krueger, A.T. et al. "Redesigning the Architecture of the Base Pair: Toward Biochemical and Biological Function of New Genetic Sets" Curr Open Chem Biol (2007) 11(69):588-594.
Krueger, A.T. et al. "Model Systems for Understanding DNA Base Pairing" Chem & Biol (2009) 16(3):242-248.
Laird, P.W, "The power and the promise of DNA methylation markers" Nat Rev Cancer (2003) 3(4):253-266.
Lehmann, A.R. "Replication of damaged DNA in mammalian cells: new solutions to an old problem" Mutant Res (2002) 509(1-2):23-34.
Lehmann, A.R. "Translesion synthesis in mammalian cells" Exp Cell Res (2006) 312(14):2673-2676.
Lehmann, A.R. et al. "Transiesion synthesis: Y-family polymerases and the polymerase switch" DNA Repair (Amst) (2007) 6(7):891-899.
Levene, M.J. et al. "Zero-mode Waveguides for Single-Molecule Analysis at High Concentrations" Science (2003) 299(5607):682-686.
Lindahl, T. "Instability and decay of the primary structures of DNA" Nature (1993) 362(6422):709-715.
Lister, R. et el. "Finding the fifth base: Genome-wide sequencing at cytosine methylation" Genome Res (2009) 19:959-966.
Loakes, D. et al. "Polymerase engineering: towards the encoded synthesis of unnatural biopolymers" Chem Commun (2009) 31:4619-4631.
Masutani, C. et al. "The XPV (xeroderma pi mentosum variant gene encodes human DNA polymease" Nature (1999) 399(6737):700-704.
Matray, T.J. et at. "A specific partner for abasic damage in DNA" Nature (1999) 399:704-708.
McCullough, A.K et al. "Initiation of Base excision repair: glycosylase mechanisms and structures" Ann Rev Biochem (1999) 68-255-285.
Abbotts, J. et al. "Studies on the Mechanism of *Escherichia coli*DNA Polymerase I Large Fragment" Journal of Biological Chemistry (1988)283:15094-15103.
Galas, D.J. et el. "DNAase Footprinting: A Simple Method for the Detection of Protein-DNA Binding Specificity," Nucleic Acids Research (1978) 5(9):3157-3170.
Vlassov, V.V. et al. "Extracellular Nucleic Acids" Bioessays (2207) 29(7):654-667.
International Search Report and Written Opinion issued Jun. 26, 2012 for corresponding PCT application PCT/US2011/060338.
First Office Action for related case CN 200980166796.7 dated Nov. 26, 2012.
First Office Action dated Jul. 28, 2014 for related case AU 2011326026.
International Preliminary Report on Patentability dated May 23, 2013 for corresponding PCT application PCT/US2011/060333.
Secono Office Action for related case CN 205980156796.7 dated Jun. 3, 2013.
First Office Action dated Apr. 1, 2014 for related case AU 2009325069.
Decision on Rejection for related case CN 200980156796.7 dated Apr. 1, 2014.
First office Action dated Jul. 22, 2013 for related case EP 09832251.4.
Eid, J. et al. Supporting Online Material for "Real-time DNA Sequencing from Single Polymerase Molecules", Published Nov. 10, 2008 on Science Express DOI: 10.1126/science.1162986.
Deng, J. "Targeted Bisulfite Sequencing Reveals Changes in DNA Methylation Associated with Nuclear Programming," Nature Biotechnology (2009) 27(4):353-360.
Program for Personal Genomics Meeting, Cold Spring Harbor, Oct. 2008.
Pacific Biosciences Presentation, "Harnessing Nature's Powerful Sequencing Engines: Single Molecule Real-Time DNA Sequencing," Cold Spring Harbor Personal Genomics Meeting, Oct. 12, 2008.
Frommer, M. et al. "A Genomic Sequencing Protocol That Yields a Positive Display of 5-Methylcytosine Residues in Individual DNA Strands," PNAS (1992) 89:1827-1831.
Laird, C.D. et al. "Haimin-Bisulfite PCR: Assessing Epigenetic Methylation Patterns on Complementary Strands of Individual DNA Molecules," PNAS (2004) 101(1):204-209.
Third Office Action for related case CN 200980156796.7 dated Oct. 21, 2013.
Cheetham et al. "Structural basis for initiation of transcription from an RNA polymerase-promoter complex," Nature (1999):80-83.
Clark et al. "DNA methylation: bisulphate modification and analysis," Nature Protocols (2006) 1:2353-2364.
DeHaseth et al. "RNA polymerase-promoter interactions: the comings and goings of RNA polymerase," Journal of Bacteriology (1998) 180:1019-2025.
Guo et al. "Weakening of the T7 promoter-polymerase interaction facilitates promoter release," J. Biol. Chem. (2005) 280:14956-14961.
Gupta "Single-molecule DNA sequencing technologies for future genomics research," Trends in Biotechnology (2008) 26:602-611.
Hammond et al. "Post-transcriptional gene silencing by double-stranded RNA," Nature Reviews Genetics (2001) 2:110-119.
Laird et al. "Simplified mammalian DNA isolation procedure," Nucleic Acid Research (1991) 19:4293.
Matsumura et al. "Photochemical Transition of 5-Methlcytosine to Thymine by DNA Photo ligation," Nucleic Acids Symposium Series (2007) No. 51:233-234.
Morris et al. "Isolation and analysis of double-stranded RNA from 12 virus-infected plant and fungal tissue," Phytopathology (1979) 69:854-858.
Munroe et al. "Third-generation sequencing fireworks at Macro Island," Nature Biotechnology (2010) 28: 426-428.

(56) References Cited

OTHER PUBLICATIONS

Privat et al. "Photochemical deamination and demthylation of methylcytosine," Chem. Res. Toxicol. (1996).
Ravanat et al. "Direct and indirect effects of UV radiation on DNA and its componenets," Journal of Photochemistry and Photobiology B: Biology (2001) 63:88-102.
Sandal et al. Characterization and comparison of biofilm development by pathogenic and commensal isolates of Histophilus somni. Journal of Bacteriology (2007) 189:8179-8185.
Shadt et al. "A window into third-generation sequencing," Human Molecular Genetics (2010) 19:R227-R240.
Shendure et al. "Advanced sequencing technologies," Nature Reviews Genetics (2004) 5:335-345.
Vroom et al. "Modular construction of plasmids through ligation-free assembly of vector components with oligonucleotide linkers," BioTechniques (2008) 44:924-926.
Zilberman et al. "Genome-wide analysis of DNA methylation patterns," Development (2007) 134:3959-3965.
Second office Action dated Apr. 9, 2015 for related case EP 09832251.4.
Second Office Action dated Nov. 21, 2014 for related case AU 2009325069.

* cited by examiner

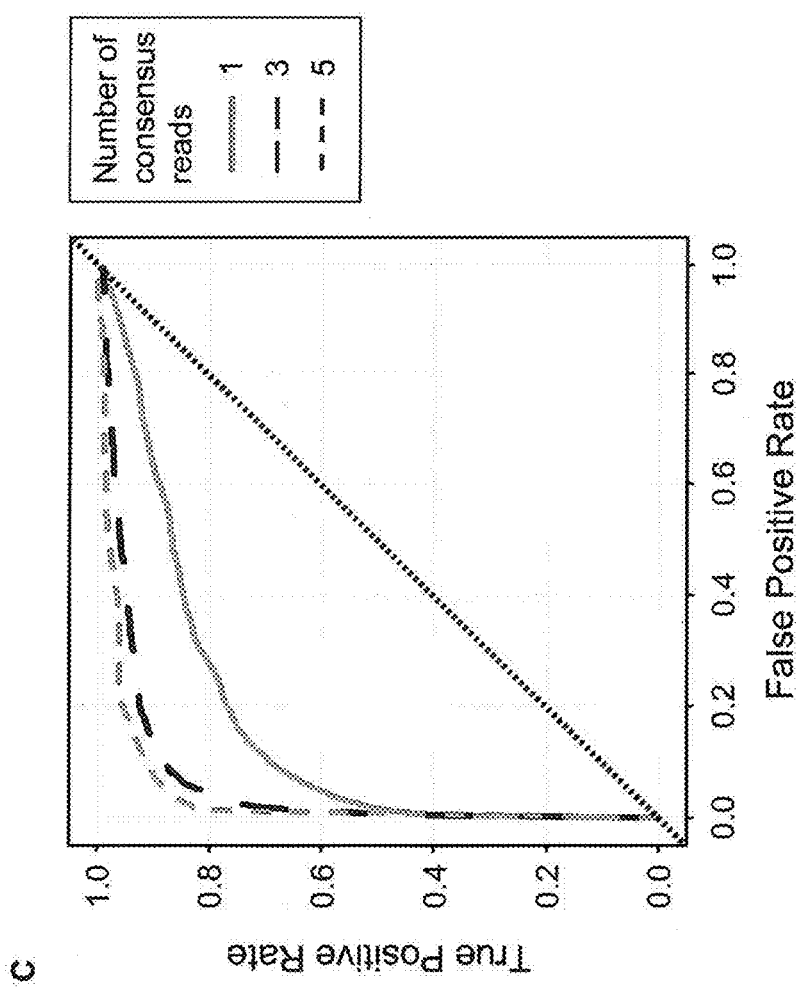
Figure 14, cont.

Ribo A   CCAGACTCGGGCAT*a*CTTGATCGACCATGCATAGGCGGAACAAC — SEQ ID NO: 1
         TGAGCCCGTATGAACTAGCTGGTACGTATCCGCCTT — SEQ ID NO: 2

Ribo C   CCAGACTCGGGCATA*c*TTGATCGACCATGCATAGGCGGAACAAC — SEQ ID NO: 3
         TGAGCCCGTATGAACTAGCTGGTACGTATCCGCCTT — SEQ ID NO: 2

Ribo U   CCAGACTCGGGCATAC*u*TGATCGACCATGCA*u*AGGCGGAACAAC — SEQ ID NO: 4
         TGAGCCCGTATGAACTAGCTGGTACGTATCCGCCTT — SEQ ID NO: 2

Ribo G   CCAGACTCGG*g*GCATACTTGATCGACCATG*g*CATAGGCGGAACAAC — SEQ ID NO: 5
         TGAGCCCGTATGAACTAGCTGGTACGTATCCGCCTT — SEQ ID NO: 2

Control  CCAGACTCGGGCATACTTGATCGACCATGCATAGGCGGAACAAC — SEQ ID NO: 6
         TGAGCCCGTATGAACTAGCTGGTACGTATCCGCCTT — SEQ ID NO: 2

Figure 20

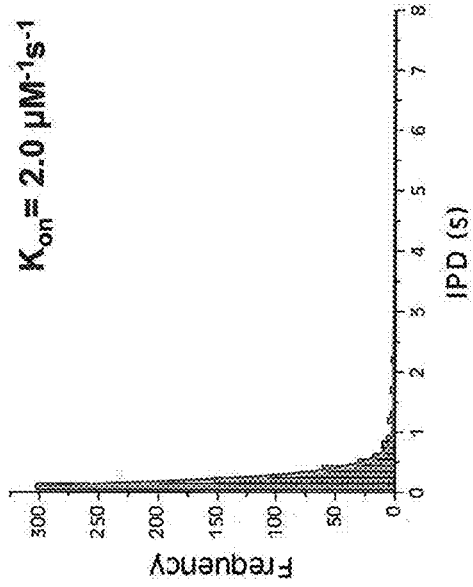
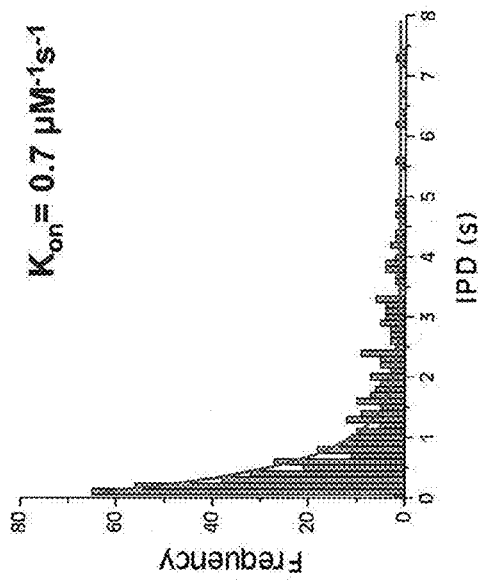
Figure 27

METHODS FOR IDENTIFYING NUCLEIC ACID MODIFICATIONS

CROSS-REFERENCE TO RELATED APPLICATIONS

This application is a continuation-in-part of U.S patent application Ser. No. 12/635,618, filed Dec. 10, 2009, which claims the benefit of Provisional U.S. Patent Application No. 61/201,551, filed, Dec. 11,2008; Provisional U.S. Patent Application No. 61/180,350, filed May 21, 2009; and Provisional U.S. Patent Application No. 61/186,661, filed Jun. 12, 2009; the full disclosures of which are hereby incorporated herein by reference in their entireties for all purposes.

STATEMENT REGARDING FEDERALLY SPONSORED RESEARCH

The U.S. government has a paid-up license in this invention and the right in limited circumstances to require the patent owner to license others on reasonable terms as provided for by the terms of Grant No. 5RC2HG005618-02 awarded by the National Human Genome Research Institute (NHGRI) of the National Institutes of Health (NIH).

BACKGROUND OF THE INVENTION

Assays for analysis of biological processes are exploited for a variety of desired applications. For example, monitoring the activity of key biological pathways can lead to a better understanding of the functioning of those systems as well as those factors that might disrupt the proper functioning of those systems. In fact, various different disease states caused by operation or disruption of specific biological pathways are the focus of much medical research. By understanding these pathways, one can model approaches for affecting them to prevent the onset of the disease or mitigate its effects once manifested.

A stereotypical example of the exploitation of biological process monitoring is in the area of pharmaceutical research and development. In particular, therapeutically relevant biological pathways, or individual steps or subsets of individual steps in those pathways, are often reproduced or modeled in in vitro systems to facilitate analysis. By observing the progress of these steps or whole pathways in the presence and absence of potential therapeutic compositions, e.g., pharmaceutical compounds or other materials, one can identify the ability of those compositions to affect the in vitro system, and potentially beneficially affect an organism in which the pathway is functioning in a detrimental way. By way of specific example, reversible methylation of the 5' position of cytosine by methyltransferases is one of the most widely studied epigenetic modifications. In mammals, 5-methylcytosine (5-MeC) frequently occurs at CpG dinucleotides, which often cluster in regions called CpG islands that are at or near transcription start sites. Methylation of cytosine in CpG islands can interfere with transcription factor binding and is associated with transcription repression and gene regulation. In addition, DNA methylation is known to be essential for mammalian development and has been associated with cancer and other disease processes. Recently, a new 5-hydroxymethylcytosine epigenetic marker has been identified in certain cell types in the brain, suggesting that it plays a role in epigenetic control of neuronal function (S. Kriaucionis, et al., *Science* 2009, 324(5929): 929-30, incorporated herein by reference in its entirety for all purposes). Further information on cytosine methylation and its impact on gene regulation, development, and disease processes is provided in the art, e.g., in A. Bird, *Genes Dev* 2002, 16, 6; M. Gardiner-Garden, et al., *J Mol Biol* 1987, 196, 261; S. Saxonov, et al., *Proc Natl Acad Sci USA* 2006, 103, 1412; R. Jaenisch, et al., *Nat Genet* 2003, 33 Suppl, 245; E. Li, et al., *Cell* 1992, 69, 915; A. Razin, et al., *Hum Mol Genet* 1995, 4 Spec No, 1.751; P. A. Jones, et al., *Nat Rev Genet* 2002, 3, 415; P. A. Jones, et al., *Nat Genet* 1999, 21, 163; and K. D. Robertson, *Nat Rev Genet* 2005, 6, 597, all of which are incorporated herein by reference in their entireties for all purposes.

In contrast to determining a human genome, mapping of the human methylome is a more complex task because the methylation status differs between tissue types, changes with age, and is altered by environmental factors (P. A. Jones, et al., *Cancer Res* 2005, 65, 11241, incorporated herein by reference in its entirety for all purposes). Comprehensive, high-resolution determination of genome-wide methylation patterns from a given sample has been challenging due to the sample preparation demands and short read lengths characteristic of current DNA sequencing technologies (K. R. Pomraning, et al., *Methods* 2009, 47, 142, incorporated herein by reference in its entirety for all purposes).

Bisulfite sequencing is the current method of choice for single-nucleotide resolution methylation profiling (S. Beck, et al., *Trends Genet* 2008, 24, 231; and S. J. Cokus, et al., *Nature* 2008, 452, 215, the disclosures of which are incorporated herein by reference in their entireties for all purposes). Treatment of DNA with bisulfite converts unmethylated cytosine, but not 5-MeC, to uracil (M. Frommer, et al., *Proc Natl Acad Sci USA* 1992, 89, 1827, incorporated herein by reference in its entirety for all purposes). The DNA is then amplified (which converts all uracils into thymines) and subsequently analyzed with various methods, including microarray-based techniques (R. S. Gitan, et al., *Genome Res* 2002, 12, 158, incorporated herein by reference in its entirety for all purposes) or $2^{nd}$-generation sequencing (K. H. Taylor, et al., *Cancer Res* 2007, 67, 8511; and R. Lister, et al., *Cell* 2008, 133, 523, both incorporated herein by reference in their entireties for all purposes). While bisulfite-based techniques have greatly advanced the analysis of methylated DNA, they also have several drawbacks. First, bisulfite sequencing requires a significant amount of sample preparation time (K. R. Pomraning, et al., supra). Second, the harsh reaction conditions necessary for complete conversion of unmethylated cytosine to uracil lead to degradation of DNA (C. Grunau, et al., *Nucleic Acids Res* 2001, 29, E65, incorporated herein by reference in its entirety for all purposes), and thus necessitate large starting amounts of the sample, which can be problematic for some applications.

Furthermore, because bisulfite sequencing relies on either microarray or $2^{nd}$-generation DNA sequencing technologies for its readout of methylation status, it also suffers from the same limitations as do these methodologies. For array-based procedures, the reduction in sequence complexity caused by bisulfite conversion makes it difficult to design enough unique probes for genome-wide profiling (S. Beck, et al., supra). Most $2^{nd}$-generation DNA sequencing techniques employ short reads and thus have difficulties aligning to highly repetitive genomic regions (K. R. Pomraning, et al., supra). This is especially problematic, since many CpG islands reside in such regions. Given these limitations, bisulfite sequencing is also not well suited for de novo methylation profiling (S. Beck, et al., supra).

In another widely used technique, methylated DNA immunoprecipitation (MeDIP), an antibody against 5-MeC is used to enrich for methylated DNA sequences (M. Weber, et al., *Nat Genet* 2005, 37, 853, incorporated herein by reference in its entirety for all purposes). MeDIP has many advantageous attributes for genome-wide assessment of methylation status, but it does not offer as high base resolution as bisulfite treatment-based methods. In addition, it is also hampered by the same limitations of current microarray and $2^{nd}$-generation sequencing technologies.

Research efforts aimed at increasing our understanding of the human methylome would benefit greatly from the development of a new methylation profiling technology that does not suffer from the limitations described above. Accordingly, there exists a need for improved techniques for detection of modifications in nucleic acid sequences, and particularly nucleic acid methylation.

Typically, modeled biological systems rely on bulk reactions that ascertain general trends of biological reactions and provide indications of how such bulk systems react to different effectors. While such systems are useful as models of bulk reactions in vivo, a substantial amount of information is lost in the averaging of these bulk reaction results. In particular, the activity of and effects on individual molecular complexes cannot generally be teased out of such bulk data collection strategies.

Single-molecule real-time analysis of nucleic acid synthesis has been shown to provide powerful advantages over nucleic acid synthesis monitoring that is commonly exploited in sequencing processes. In particular, by concurrently monitoring the synthesis process of nucleic acid polymerases as they work in replicating nucleic acids, one gains advantages of a system that has been perfected over millions of years of evolution. In particular, the natural DNA synthesis processes provide the ability to replicate whole genomes in extremely short periods of time, and do so with an extremely high level of fidelity to the underlying template being replicated.

The present invention is directed to a variety of different single-molecule real-time analyses for monitoring the progress and effectors of biological reactions, and in particular detecting modifications in nucleic acid sequences. For example, the present invention provides a direct methylation sequencing technology based on observing the kinetics of single polymerase molecules in real time and with high multiplex. This technique will provide for fast and economical analysis of methylation patterns, even in repetitive genomic regions.

BRIEF SUMMARY OF THE INVENTION

The present invention is generally directed to the detection of modified nucleic acid sequences, and particularly the detection of methylated bases within nucleic acid sequences using a real time direct detection of such methylated sites. The present invention is expected to have a major impact on research aiming to illuminate the role of DNA methylation in human health.

In certain aspects of the invention, methods are provided for identification of a modification in a nucleic acid molecule. In general, a template nucleic acid comprising the modification and an enzyme capable of processing the template are provided. The template nucleic acid is contacted with the enzyme, and the subsequent processing of the template by the enzyme is monitored. A change in the processing is detected, and this change is indicative of the presence of the modification in the template. Exemplary modifications that can be detected by the methods of the invention include, but are not limited to methylated bases (e.g., 5-methylcytosine, $N^6$-methyladenosine, etc.), pseudouridine bases, 7,8-dihydro-8-oxoguanine bases, 2'-O-methyl derivative bases, base J, s4U, s6G, nicks, apurinic sites, apyrimidic sites, pyrimidine dimers, a cis-platen crosslinking products, oxidation damage, hydrolysis damage, bulky base adducts, thymine dimers, photochemistry reaction products, interstrand crosslinking products, mismatched bases, secondary structures, and bound agents. In preferred embodiments, nucleotides or analogs thereof that are incorporated into a nascent strand synthesized by the enzyme are distinctly labeled to allow identification of a sequence of specific nucleotides or nucleotide analogs so incorporated. In certain preferred embodiments, labels are linked to nucleotides or nucleotide analogs through a phosphate group, e.g., a phosphate group other than the alpha phosphate group. As such, the labels are removed from the nucleotide or nucleotide analog upon incorporation into the nascent strand.

In some embodiments, the template nucleic acid is treated prior to processing by the enzyme, e.g., to alter the modification. The treatment may be chemical or enzymatic, and includes, e.g., glycosylase modification, bisulfite modification, DMS modification, cytosine methyltransferase modification, hydroxylation, TET1 modification, and cytidine deaminase modification. In some embodiments, non-natural nucleotide analogs (e.g., pyrene analogs) are incorporated into a nascent strand synthesized by the enzyme. In some embodiments, the methods comprise both treatment of the template and incorporation of non-natural nucleotide analogs into the nascent strand. In some embodiments, non-natural nucleotides are incorporated into a nascent strand in a position to pair with a modification in the template. For example, a methylated cytosine in the template can be paired with a modified guanine nucleotide analog; a template modification can pair with a non-natural nucleotide analog to form a non-natural base pair, e.g., isocytosine and isoguanine; 5-methyl-isocytosine and isoguanine; Im-$N^O$ and Im-$O^N$; A* and T*; and 8-oxoG and adenine. In some embodiments, non-incorporatable nucleotide analogs bind the template/enzyme complex, but are not incorporated into the nascent strand, and detection of this "nonproductive" binding serves as an indication of the modification in the template. Such non-incorporatable nucleotide analogs are preferably distinctly labeled to facilitate monitoring, and optionally to distinguish such binding from incorporation of incorporatable nucleotide analogs that comprise labels.

In certain embodiments, the template nucleic acid comprises regions of internal complementarity (e.g., a double-stranded portion) and at least one single-stranded portion, and preferably the modification is located within at least one of the regions of internal complementarity. In certain embodiments, the template is a circular template. In certain embodiments, the template is a circular template comprising at least two regions of internal complementarity. In certain embodiments, the enzyme is a polymerase, such as a DNA polymerase, and RNA polymerase, a reverse transcriptase, or a derivative or variant thereof. In preferred embodiments, the enzyme is a polymerase enzyme capable of strand displacement. In specific embodiments, the enzyme is a Φ29 polymerase, optionally comprising at least one mutation at a position selected from the group consisting of K392, K422, I93, M188, K392, V399, T421, K422; S95, Y101, M102; Q99, L123, K124, T189, A190; G191, S388; P127, L384, N387, S388; and L389, Y390, and G391.

Examples of changes in the processing of the template by the enzyme that are monitored in various embodiments of the invention include, but are not limited to, kinetics, processivity, affinity, rate, strand-displacement activity, signal characteristics, error metrics, signal context, and the like. In some embodiments, a change occurs only at the modification, and in other embodiments the change occurs at one or more positions proximal to the modification, which may also include the modification position.

In certain aspects, the methods further comprise mapping the modification. In certain preferred embodiments, mapping the modification comprises analyzing a portion of the sequence read that was generated immediately prior to, during, and/or immediately after detecting the change in processing to determine a sequence complementary to the template nucleic acid; determining the complement of the sequence complementary to the template nucleic acid; and mapping the modification at a position in the template nucleic acid that is proximal to the complement of the sequence complementary to the template nucleic acid.

In certain embodiments, a change in the processing that is indicative of the modification is a kinetic difference in the processing (e.g., detected as an alteration in one or more of interpulse duration, interpulse width, processivity, cessation of processing, etc.) and/or a change in an error metric (e.g., accuracy, an increase in binding events that do not result in incorporation, etc.) The change in processing can be indicative of the type of modification is present in the template nucleic acid, since different types of modifications have different effects on the activity and/or fidelity of the enzyme.

In preferred embodiments, the monitoring occurs in real time during the processing of the template by the enzyme. In preferred embodiments, the template nucleic acid and the enzyme form a complex that is immobilized at a reaction site on a substrate, and in more preferred embodiments a plurality of complexes are immobilized at optically resolvable reaction sites on the substrate, wherein a single complex immobilized at one of the reaction sites is optically resolvable from any other of the complexes immobilized at any other of the reaction sites. In certain embodiments, the optically resolvable reaction sites are nanometer-scale apertures in the substrate, and can be optical confinements, such as zero-mode waveguides. In preferred embodiments, the template nucleic acid is plurality of template nucleic acids that are optically resolvable from one another during the monitoring. Preferably, the template nucleic acid is not amplified prior to contacting it with the enzyme.

In some embodiments, the modification is secondary structure in the template nucleic acid, e.g., a hairpin loop, supercoiling, internal hybridization, etc., and the change in the modification is a kinetic change, e.g., an increased interpulse duration or increased pulse width. Certain methods for identifying such a secondary structure generally comprise generating a sequence read for the template nucleic acid before, during, and after the kinetic change; identifying a first portion of the sequence read generated before and/or during the kinetic change that is complementary to a second portion of the sequence read generated during and/or after the kinetic change; and determining a likelihood that the first and second portions may have been annealed in the template nucleic acid during the processing, e.g. to form a hairpin loop, based at least upon the nucleotide composition of the first portion and the second portions.

In another aspect of the invention, methods for detecting binding of an agent to a single nucleic acid template are provided. In certain embodiments, such methods generally comprise providing the single nucleic acid template in complex with a polymerase; introducing a reaction mixture to the complex, wherein the reaction mixture comprises the agent; and monitoring synthesis of a polynucleotide by the polymerase, wherein the polynucleotide is complementary to the single nucleic acid template, and wherein a change in the synthesis is indicative of binding of the agent to the single nucleic acid template. Examples of agents appropriate for use in such methods include, but are not limited to, transcription factors, polymerases, reverse transcriptases, histones, restriction enzymes, antibodies, nucleic acid binding proteins, and nucleic acid binding agents. Examples of single nucleic acid templates appropriate for use in such methods include, but are not limited to, double-stranded DNA, double-stranded RNA, single-stranded DNA, single-stranded RNA, DNA/RNA hybrids, and templates comprising both double-stranded and single-stranded regions.

In certain aspects of the invention, a consensus binding site of the agent is determined. This determination can comprise, e.g., performing a plurality of sequencing-by-synthesis reactions on a set of single nucleic acid templates in the presence of the agent to generate a set of binding-affected nascent polynucleotide sequences; performing a plurality of sequencing-by-synthesis reactions on the set of single nucleic acid templates in the absence of the agent to generate a set of full-length nascent polynucleotide sequences; analyzing the binding-affected nascent polynucleotide sequences to determine a location at which the agent bound the single nucleic acid template during the sequencing-by-synthesis reactions in the presence of the agent; and identifying a sequence common to the full-length nascent polynucleotide sequences at the location, thereby identifying the consensus binding site of the agent. In certain embodiments, the binding-affected nascent polynucleotide sequences are truncated nascent polynucleotide sequences; and in other embodiments, the binding-affected nascent polynucleotide sequences are nascent polynucleotide sequences whose synthesis was paused at the location at which the agent bound.

In yet further aspects of the invention, methods for detecting modifications in a single nucleic acid template during a sequencing-by-synthesis reaction are provided. For example, such a method can comprise providing the single nucleic acid template in complex with a polymerase; introducing a reaction mixture to the complex, wherein the reaction mixture comprises an agent that specifically binds to the modification; and monitoring synthesis of a polynucleotide by the polymerase, wherein the polynucleotide is complementary to the single nucleic acid template, and wherein a pause or cessation of the synthesis of the polynucleotide is indicative of binding of the agent to the single nucleic acid template, thereby detecting the modification in the single nucleic acid template. In certain embodiments, the modification is an 8-oxoG lesion and/or the agent is a protein is selected from the group consisting of hOGG1, FPG, yOGG1, AlkA, Nth, Nei, MutY, UDG, SMUG, TDG, NEIL, an antibody against 8-oxoG, or a binding domain thereof. In other embodiments, the modification is a methylated base and/or the agent is a protein selected from the group consisting of MECP2, MBD1, MBD2, MBD4, UHRF1, an antibody against the methylated base, or a binding domain thereof. In further embodiments, the modification is a secondary structure formation in the nucleic acid template. Preferably, the complex is immobilized in an optical confinement. The template can comprise, e.g., single-stranded linear nucleic acid, single-stranded circular nucleic acid, double-stranded linear nucleic acid, double-stranded circular nucleic acid, or a combination thereof.

In certain embodiments, a modification in a template nucleic acid can be repaired by including components of damage repair machinery in the reaction mixture, e.g., during a sequencing-by-synthesis reaction. In certain embodiments, the readlength of the sequencing-by-synthesis reaction is longer than that for a further sequencing-by-synthesis reaction performed with the single nucleic acid template in complex with the polymerase, but absent the agent and the damage repair machinery.

In other aspects of the invention, methods for bypassing one or more modifications in a single nucleic acid template during a sequencing-by-synthesis reaction are provided. Certain exemplary methods include providing the single nucleic acid template in complex with a sequencing engine; introducing a reaction mixture to the complex, wherein the reaction mixture comprises a bypass polymerase; initiating the sequencing-by-synthesis reaction; monitoring synthesis of a polynucleotide by the sequencing engine, wherein the polynucleotide is complementary to the single nucleic acid template, and wherein a pause or cessation of the synthesis of the polynucleotide is indicative that the sequencing engine has encountered a modification in the single nucleic acid template; subsequently monitoring synthesis of the polynucleotide by the bypass polymerase, which is indicative that the modification is being bypassed; and repeating the monitoring steps each time a further modification is encountered in the single nucleic acid template, thereby bypassing one or more modifications in a single nucleic acid template during a sequencing-by-synthesis reaction. In certain embodiments, the bypass polymerase comprises a detectable label and detection of a signal from the detectable label during the sequencing-by-synthesis reaction is indicative that the bypass polymerase is actively synthesizing the polynucleotide. In preferred embodiments, the readlength of the sequencing-by-synthesis reaction is longer than that for a further sequencing-by-synthesis reaction performed with the single nucleic acid template in complex with the sequencing engine, but absent the bypass polymerase. In specific embodiments, the reaction mixture comprises multiple different bypass polymerases and a processivity factor. Preferably, at least one of the single nucleic acid template, the sequencing engine, and the bypass polymerase is immobilized, directly or indirectly, in an optical confinement. For example, the template can be immobilized by hybridization to an oligonucleotide primer immobilized in the optical confinement. In certain preferred embodiments, the single nucleic acid template is processed by the sequencing engine multiple times at a single reaction site, and further wherein redundant sequence data is generated. Nucleic acid templates for use with the methods can be circular and/or can comprise multiple copies of a nucleic acid segment of interest. Further, in certain embodiments the sequencing-by-synthesis reaction generates a polynucleotide comprising multiple copies of a segment complementary to the segment of interest, and further wherein redundant sequence data is generated.

In further aspects, novel compositions are provided. For example, in certain embodiments a composition of the invention comprises a substrate having a reaction site that is optically resolvable from any other reaction site on the substrate; a single complex of a template and sequencing engine immobilized at the reaction site; a mixture of incorporatable nucleotides or nucleotide analogs; and at least one modification in the template nucleic acid, wherein the template at or proximal to the modification is processed differently than the template distal from the modification. In some embodiments the modification is a non-natural base in the template. The modification can be located in either a strand of the template nucleic acid that is complementary to a nascent strand synthesized by the sequencing engine, or a strand of the template nucleic acid that is displaced by the sequencing engine. In certain preferred embodiments, the template nucleic acid comprises internally complementary regions, and optionally, the modification is located within one of the internally complementary regions. Certain embodiments further comprise at least one type of non-incorporatable nucleotide analog. Certain embodiments comprise at least one type of non-natural incorporatable nucleotide analog. Preferably, one or more or all of the nucleotides or nucleotide analogs in a composition of the invention are tagged with distinct labels that distinguish different types of nucleotides or nucleotide analogs from one another. Compositions of the invention can also include an agent other than the sequencing engine that binds to the modification and/or chemically or enzymatically alters the modification. Preferably, compositions of the invention comprise a nascent strand generated by the sequencing engine, wherein the nascent strand is complementary to the template nucleic acid, and, optionally, comprises multiple copies of regions complementary to the template nucleic acid. Further, certain compositions comprise a nanometer-scale aperture in the substrate, where the reaction site is disposed within the nanometer-scale aperture, e.g., a zero-mode waveguide.

In further aspects of the invention, systems for identification of modifications within a nucleic acid template are provided. In certain preferred embodiments, a system of the invention comprises a solid support having a polymerase complex disposed thereon (e.g., at a reaction site, e.g., in a nanoscale aperture, e.g., in a zero-mode waveguide), the polymerase complex comprising a nucleic acid template comprising a modification; a mounting stage configured to receive the solid support; an optical train positioned to be in optical communication with at least a portion of the solid support to detect signals emanating therefrom; a translation system operably coupled to the mounting stage or the optical train for moving one of the optical train and the solid support relative to the other; and a data processing system operably coupled to the optical train. Preferably, the polymerase complex comprises a polymerase enzyme that is actively processing the nucleic acid template. More preferably, the polymerase complex comprises a polymerase enzyme that is processively synthesizing a nascent strand by template-directed synthesis. In preferred embodiments, the optical train detects signals emanating from the solid support during the processing of the nucleic acid template.

In certain aspects, the invention provides method for identifying modifications within nucleic acids molecules comprising introducing a further modification into a template nucleic acid already comprising a modification of interest. An enzyme processes the template nucleic acid, and the processing of the template by the enzyme is monitored. Changes in the processing are indicative of the further modification, and therefore, indirectly, the modification of interest is identified. The modification of interest can be any modification useful for directing or marking the template to facilitate introduction of the further modification. For example, the modification of interest can be chosen from the following: a methylated base, a hydroxymethylated base, HOMedU, β-D-glucosyl-HOMedU, cytosine-5-methylenesulfonate, a pseudouridine base, an 7,8-dihydro-8-oxoguanine base, a 2'-O-methyl derivative base, a nick, an apurinic site, an apyrimidic site, a pyrimidine dimer, a cis-platen crosslinking, oxidation damage, hydrolysis damage, a bulky base adduct, a thymine dimer, a photochemistry reaction product, an interstrand crosslinking product, a mismatched base, a secondary structure, and a bound agent. In some preferred embodiments, the template nucleic acid comprises a single-stranded portion and a double-stranded portion, and in some cases the double-stranded portion is a result of complementarity between two separate portions of the template nucleic acid. In some embodiments, the template nucleic acid comprises a first polynucleotide region comprising the modification and a second polynucleotide region complementary to the first polynucleotide region, where the first polynucleotide region and the second polynucleotide region are on a single strand of the template nucleic acid, e.g., in different regions of a single-stranded circular template nucleic acid. Typically, the template nucleic acid is subjected to a treatment to introduce the further modification, and such a treatment can comprise exposure to a modifying agent, e.g., a glycosylase, bisulfite, DMS, a cytosine methyltransferase, a hydroxylase (e.g., TET1 protein), a restriction enzyme, a glucosyltransferase, NMIA, CDI, and a cytidine deaminase. For example, the treatment can comprise exposure to bisulfite that converts 5-hmC to CMS in the template. The treatment can also comprise addition of a sugar moiety (e.g., sucrose, glucose, maltose, galactose, dextrose, lactose, etc.) or group to a nucleobase comprising the modification. The addition of the sugar moiety serves to increase the response of the enzyme, e.g., polymerase, resulting in a greater change is processing that would occur in the absence of the sugar moiety. For example, the nucleobase can be a hydroxymethylcytosine nucleobase, which is converted to β-glucosyl-5-hydroxymethylcytosine by the addition of the sugar moiety. Addition of the sugar moiety can occur via an alpha or beta linkage. Further, a plurality of sugar moieties can be added. In further embodiments, the treatment comprises replacement of the modification with the further modification, e.g., when the modification is a methylated base and the further modification is an abasic site or a pyrene analog. In certain preferred embodiments, the processing of the template is monitored for kinetic changes, which can be indicative of a modification or a further modification. The nucleic acid template can be RNA or DNA, or can comprise both ribo- and deoxyribonucleotides, is preferably not amplified. The enzyme is preferably a polymerase enzyme, e.g., a DNA polymerase, and RNA polymerase, a reverse transcriptase, or a derivative thereof. Preferably, the processing is a sequencing reaction (e.g., a single-molecule sequencing reaction), and where the template is a closed circular template and the polymerase is capable of strand displacement, the processing can comprise rolling-circle replication of the template, which can generate redundant sequence data for the template. The change in processing can occur at the modification or further modification, or can occur at one or more positions upstream or downstream of the modification or further modification, and can be a kinetic change such as an alteration in interpulse duration or pulse width. The change in processing is preferably indicative of the type of modification and/or further modification present in the template. In certain embodiments, mapping the modification further comprises analyzing a portion of the sequence read that was generated immediately prior to, during, or immediately after the detecting the change in processing to determine a sequence complementary to the template nucleic acid; determining the complement of the sequence complementary to the template nucleic acid in f; and mapping the modification at a position in the template nucleic acid that is proximal to the complement of the sequence complementary to the template nucleic acid in f. In preferred embodiments, the monitoring occurs in real time during the processing. In further aspects, the template nucleic acid and enzyme form a complex that is immobilized at a reaction site on a substrate, and a plurality of such complexes can be immobilized at optically resolvable reaction sites on the substrate. Optionally, these optically resolvable reaction sites are nanometer-scale apertures in the substrate, preferably with optical confinement properties, e.g., such as zero-mode waveguides.

Methods are also provided for mapping binding sites of binding agents bound to or previously bound to a nucleic acid template. In certain embodiments, a method of mapping a binding site comprises exposing a single nucleic acid template to a binding agent, subjecting the template to a template-directed synthesis reaction, and monitoring the reaction for a change indicative of the binding site. The binding agent can be any agent that binds to the template, including transcription factors, polymerases, reverse transcriptases, histones, restriction enzymes, antibodies, nucleic acid binding proteins, nucleic acid binding agents, and nucleic acid damage binding agents. The single nucleic acid template is typically one of a double-stranded DNA, a double-stranded RNA, a single-stranded DNA, a single-stranded RNA, a DNA/RNA hybrid, and a combination thereof. In certain embodiments, the methods further comprise crosslinking the binding agent to the single nucleic acid template prior to the template-directed synthesis, and in some cases the crosslinking is photoactivatable crosslinking. Optionally, prior to the template-directed synthesis the crosslinked binding agent can be removed from the single nucleic acid template, e.g., by protease or other degradative treatment. In certain embodiments, the change in the synthesis reaction is detected at or proximal to a remnant of the crosslinking that remains on the nucleic acid template after removal of the binding agent. In some embodiments, an affinity purification is performed to isolate portions of the nucleic acid template to which the binding agent is associated, e.g., after crosslinking. Optionally, the single nucleic acid template can comprise thiol-modified nucleosides, e.g., 4-thiouridine, 6-thioguanosine, 2-thiocytosine, or 4-thiothymidine. In certain embodiments, the binding agent is linked to a modifying agent that introduces a modification into the single nucleic acid template proximal to the binding site, and further wherein the modification causes the change in the synthesis. A modifying agent linked to a binding agent can be one or more reactants that introduce modifications into a nucleic acid, e.g., methyltransferases, glycosylases, glucosytransferases, hydroxylases (e.g., TET1), and nucleic acid damaging agents. For example, a Dam adenine methyltransferase linked to a transcription factor will convert adenosine to N6-methyladenosine at loci proximal to the binding site of the transcription factor. In certain embodiments, a plurality of different binding agents can be assayed simultaneously, e.g., with each linked to a different modifying agent such that the detection of a particular modification in the template is indicative of the binding of a particular one of the binding agents proximal to that modification. Optionally, where the nucleotide sequences of binding sites for multiple different binding agents are distinct from one another, the same modifying agent can be linked to the different binding agents. In such an embodiment, the presence of a modification indicates there was a binding event, and nucleotide sequence information from that region coupled with prior knowledge of the consensus binding sites for the binding agents informs as to which binding agent was bound. The sequence data is preferably generated during the monitoring of the template-directed synthesis reaction, e.g., in real time. In further embodiments, both sequence data and modification detection and identification are used in combination to determine a binding site of a binding agent linked to a modifying agent. Preferably, the single nucleic acid template is in an optical confinement, e.g., a zero mode waveguide.

In yet further aspects, the invention provides methods for mapping a modification in a single nucleic acid sample that comprises splitting the sample and subjecting different portions of the sample to different treatments and/or manipulations. For example, a single nucleic acid sample comprising multiple nucleic acid molecules having a modification at a particular locus can be divided into two aliquots. A first aliquot is subjected to an amplification reaction that does not maintain the modification in the amplicons, and the second aliquot is not amplified. Both aliquots are subjected to a sequencing reaction, together or separately, and the nucleotide sequence reads generated are analyzed to determine the locus at which the modification occurred, that is, to "map" the modification. A optional procedure can be employed to enrich the nucleic acids comprising the modification in the single nucleic acid sample. For example, a binding agent that specifically binds the modification can be used to select the molecules having the modification by forming a binding agent/modification complex that is retained, e.g., by immobilization, while the nucleic acids not bound to the binding agent (e.g., those not comprising the modification) are removed. The selected nucleic acids are subsequently subjected to sequencing, e.g., after being released from the binding agents, or optionally, with the binding agents still bound to enhance the response of the polymerase to the modification site. The enrichment procedure can occur before or after the amplification of the first aliquot. In yet further embodiments, barcode sequences are added to nucleic acids in one or both aliquots. These barcodes are sequenced along with the template, and they serve to identify the source of a particular template, e.g., whether it came from the first or second aliquot. For example, a first barcode can be included in the nucleic acid templates in the first aliquot (e.g., before or after amplifications), and a second barcode can be included in the nucleic acid templates in the second aliquot. The two aliquots are combined and sequenced in a single sequencing reaction mixture and the sequence data generated not only provides information about the location of any modifications, but also provides the barcode sequence data to identify the source of the template. Preferably, the sequencing reactions are performed on single, optically resolvable templates to produce a separate individual sequence read for each template molecule.

In yet further aspects, the invention provides machine-implemented methods for transforming reaction data into modification detection data, wherein the reaction data is representative of a series of events during a sequencing-by-synthesis reaction wherein a nascent strand is synthesized based upon a nucleotide sequence of a template nucleic acid, and the modification detection data is representative of a presence of one or more modifications within a template nucleic acid. Preferably, one or more steps of the machine-implemented method are performed via a user interface implemented in a machine that comprises instructions stored in machine-readable medium and a processor that executes the instructions. In a final aspect of the invention, a computer program products are provided. In certain embodiments, machine-implemented methods for transforming reaction data comprise a classifier to distinguish between true incorporations and stochastic pulses, a segmenting algorithm based on a hidden Markov model architecture, and/or a segmenting algorithm based on a conditional random field framework. In certain specific embodiments, the methods identify regions in the template having a higher density of stochastic pulses than true incorporations. In certain specific embodiments, the methods identify regions in the template having higher IPD. Exemplary computer program products of the invention typically comprise a computer usable medium having a computer readable program code embodied therein, said computer readable program code adapted to be executed to implement the machine-implemented methods of the invention; and the machine-readable medium on which the results of one or more steps of the machine-implemented method are stored.

BRIEF DESCRIPTION OF THE DRAWINGS

FIG. 4A depicts fragmentation of genomic DNA to generate the DNA template. FIG. 4B illustrates DNA glycosylase excising a 5-MeC from the template.

FIG. 20 provides nucleic acid sequences from the templates used to generate the data depicted in FIGS. 21-24.

FIG. 27 provides graphs plotting IPDs in the presence and absence of $N^6$-methyladenosine modifications in RNA templates.

DETAILED DESCRIPTION OF THE INVENTION

I. General

Figure 1:
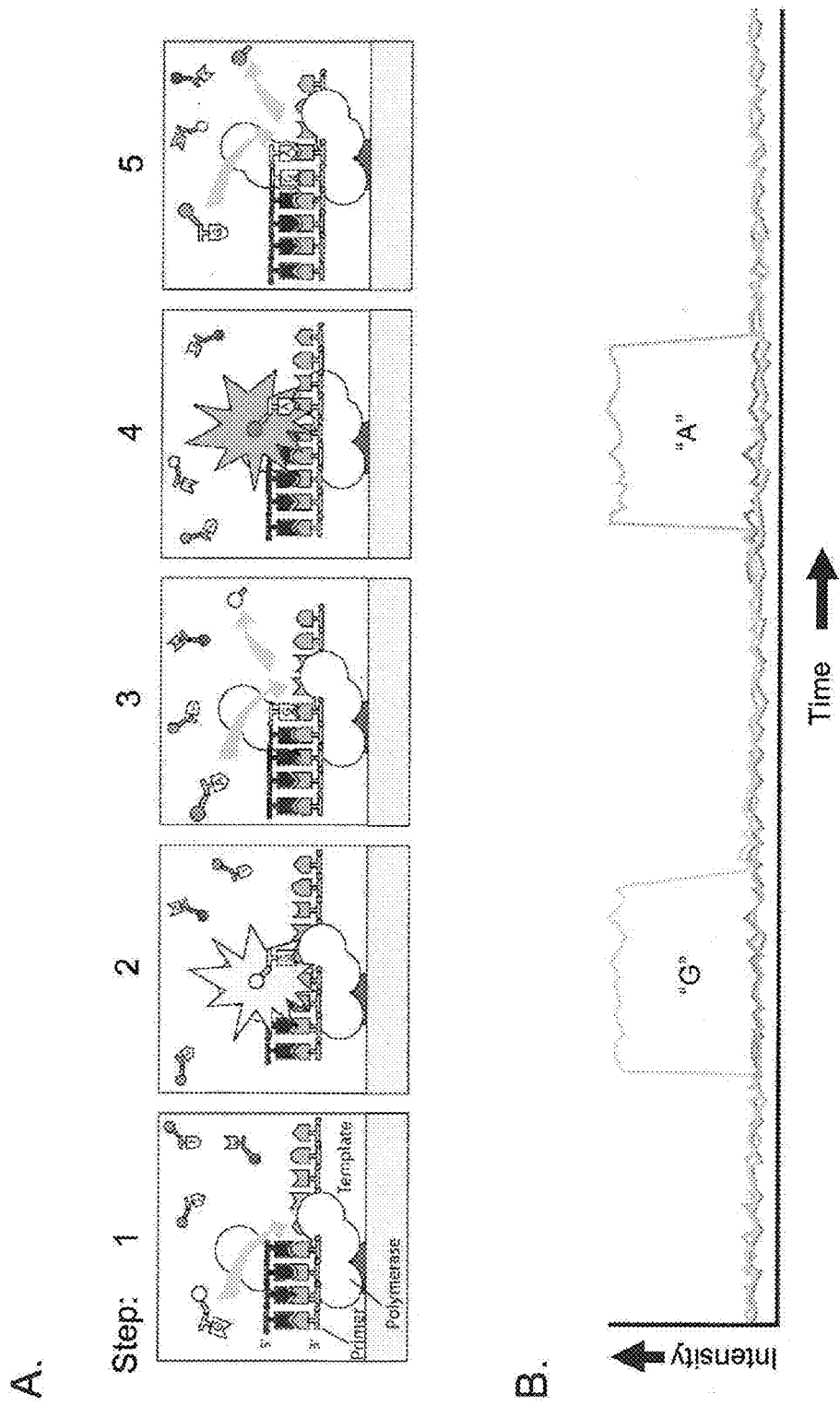
FIG. 1A and FIG. 1B provide an exemplary illustration of single-molecule, real-time (SMRT™) nucleic acid sequencing.

The present invention is generally directed to methods, compositions, and systems for detecting modifications within nucleic acid sequences, and in particularly preferred aspects, methylated nucleotides within sequence templates through the use of single molecule nucleic acid analysis. The ability to detect modifications within nucleic acid sequences is useful for mapping such modifications in various types and/or sets of nucleic acid sequences, e.g., across a set of mRNA transcripts, across a chromosomal region of interest, or across an entire genome. The modifications so mapped can then be related to transcriptional activity, secondary structure of the nucleic acid, siRNA activity, mRNA translation dynamics, kinetics and/or affinities of DNA- and RNA-binding proteins, and other aspects of nucleic acid (e.g., DNA and/or RNA) metabolism.

Although certain embodiments of the invention are described in terms of detection of modified nucleotides or other modifications in a single-stranded DNA molecule (e.g., a single-stranded template DNA), various aspects of the invention are applicable to many different types of nucleic acids, including e.g., single- and double-stranded nucleic acids that may comprise DNA (e.g., genomic DNA, mitochondrial DNA, viral DNA, etc.), RNA (e.g., mRNA, siRNA, microRNA, rRNA, tRNA, snRNA, ribozymes, etc.), RNA-DNA hybrids, PNA, LNA, morpholino, and other RNA and/or DNA hybrids, analogs, mimetics, and derivatives thereof, and combinations of any of the foregoing. Nucleic acids for use with the methods, compositions, and systems provided herein may consist entirely of native nucleotides, or may comprise non-natural bases/nucleotides (e.g., synthetic and/or engineered) that may be paired with native nucleotides or may be paired with the same or a different non-natural base/nucleotide. In certain preferred embodiments, the nucleic acid comprises a combination of single-stranded and double-stranded regions, e.g., such as the templates described in U.S. Ser. No. 12/383,855 and 12/413,258, both filed on Mar. 27, 2009 and incorporated herein by reference in their entireties for all purposes. In particular, mRNA modifications are difficult to detect by technologies that require reverse transcriptase PCR amplification because such treatment does not maintain the modification in the amplicons. The present invention provides methods for analyzing modifications in RNA molecules that do not require such amplification. In certain embodiments, methods are provided that do not require amplification of a modification-containing nucleic acid. In other embodiments, methods are provided for amplification of a modification-containing nucleic acid such that the modifications are maintained in the amplicons.

Generally speaking, the methods of the invention involve monitoring of an analytical reaction to collect "reaction data," wherein the reaction data is indicative of the progress of the reaction. Reaction data includes data collected directly from the reaction, as well as the results of various manipulations of that directly collected data, any or a combination of which can serve as a signal for the presence of a modification in the template nucleic acid. For example, certain types of reaction data are collected in real time during the course of the reaction, such as metrics related to reaction kinetics, affinity, rate, processivity, signal characteristics, and the like. As used herein, "kinetics," "kinetic signature," "kinetic response," "activity," and "behavior" of an enzyme (or other reaction component, or the reaction as a whole) generally refer to reaction data related to the function/progress of the enzyme (or component or reaction) under investigation and are often used interchangeably herein. Signal characteristics vary depending on the type of analytical reaction being monitored. For example, some reactions use detectable labels to tag one or more reaction components, and signal characteristics for a detectable label include, but are not limited to, the type of signal (e.g., wavelength, charge, etc.) and the shape of the signal (e.g., height, width, curve, etc.). Further, signal characteristics for multiple signals (e.g., temporally adjacent signals) can also be used, including, e.g., the distance between signals during a reaction, the number of extra signals (e.g., that do not correspond to the progress of the reaction), internal complementarity, and the local signal context (i.e., one or more signal that precede and/or follow a given signal). For example, template-directed sequencing reactions often combine signal data from multiple nucleotide incorporation events to generate a sequence read for a nascent strand synthesized, and this sequence read is used to derive, e.g., by complementarity, the sequence of the template strand. Other types of reaction data are generated from statistical analysis of real time reaction data, including, e.g., accuracy, precision, conformance, etc. In some embodiments, data from a source other than the reaction being monitored is also used. For example, a sequence read generated during a nucleic acid sequencing reaction can be compared to sequence reads generated in replicate experiments, or to known or derived reference sequences from the same or a related biological source. Alternatively or additionally, a portion of a template nucleic acid preparation can be amplified using unmodified nucleotides and subsequently sequenced to provide an experimental reference sequence to be compared to the sequence of the original template in the absence of amplification. Although certain specific embodiments of the use of particular types of reaction data to detect certain kinds of modifications are described at length herein, it is to be understood that the methods, compositions, and systems are not limited to these specific embodiments. Different types of reaction data can be combined to detect various kinds of modifications, and in certain embodiments more than one type of modification can be detected and identified during a single reaction on a single template. Such variations to the detailed embodiments of the invention will be clear to one of ordinary skill based upon the teachings provided herein.

In certain embodiments, redundant sequence information is generated and analyzed to detect one or more modifications in a template nucleic acid. Redundancy can be achieved in various ways, including carrying out multiple sequencing reactions using the same original template, e.g., in an array format, e.g., a ZMW array. In some embodiments in which a lesion is unlikely to occur in all the copies of a given template, reaction data (e.g., sequence reads, kinetics, signal characteristics, signal context, and/or results from further statistical analyses) generated for the multiple reactions can be combined and subjected to statistical analysis to determine a consensus sequence for the template. In this way, the reaction data from a region in a first copy of the template can be supplemented and/or corrected with reaction data from the same region in a second copy of the template. Similarly, a template can be amplified (e.g., via rolling circle amplification) to generate a concatemer comprising multiple copies of the template, and the concatemer can be subjected to sequencing, thereby generating a sequencing read that is internally redundant. As such, the sequence data from a first segment of the concatemer (corresponding to a first region of the template) can be supplemented and/or corrected with sequence data from a second segment of the concatemer also corresponding to the first region of the template. Alternatively or additionally, a template can be subjected to repeated sequencing reactions to generate redundant sequence information that can be analyzed to more thoroughly characterize the modification(s) present in the template.

The term "modification" as used herein is intended to refer not only to a chemical modification of a nucleic acids, but also to a variation in nucleic acid conformation or composition, interaction of an agent with a nucleic acid (e.g., bound to the nucleic acid), and other perturbations associated with the nucleic acid. As such, a location or position of a modification is a locus (e.g., a single nucleotide or multiple contiguous or noncontiguous nucleotides) at which such modification occurs within the nucleic acid. For a double-stranded template, such a modification may occur in the strand complementary to a nascent strand synthesized by a polymerase processing the template, or may occur in the displaced strand. Although certain specific embodiments of the invention are described in terms of 5-methylcytosine detection, detection of other types of modified nucleotides (e.g., $N^6$-methyladenosine, $N^3$-methyladenosine, $N^7$-methylguanosine, 5-hydroxymethylcytosine, other methylated nucleotides, pseudouridine, thiouridine, isoguanosine, isocytosine, dihydrouridine, queuosine, wyosine, inosine, triazole, diaminopurine, β-D-glucopyranosyloxymethyluracil (a.k.a., β-D-glucosyl-HOMedU, β-glucosyl-hydroxymethyluracil, "dJ," or "base J"), 8-oxoguanosine, and 2'-O-methyl derivatives of adenosine, cytidine, guanosine, and uridine) are also contemplated. Further, although described primarily in terms of DNA templates, such modified bases can be modified RNA bases and can be detected in RNA (or primarily RNA) templates. These and other modifications are known to those of ordinary skill in the art and are further described, e.g., in Narayan P, et al. (1987) Mol Cell Biol 7(4):1572-5; Horowitz S, et al. (1984) Proc Natl Acad Sci U.S.A. 81(18):5667-71; "RNA's Outfits: The nucleic acid has dozens of chemical costumes," (2009) C&EN; 87(36):65-68; Kriaucionis, et al. (2009) Science 324 (5929): 929-30; and Tahiliani, et al. (2009) Science 324 (5929): 930-35; Matray, et al. (1999) Nature 399(6737):704-8; Ooi, et al. (2008) Cell 133: 1145-8; Petersson, et al. (2005) J Am Chem Soc. 127(5):1424-30; Johnson, et al. (2004) 32(6):1937-41; Kimoto, et al. (2007) Nucleic Acids Res. 35(16):5360-9; Ahle, et al. (2005) Nucleic Acids Res 33(10):3176; Krueger, et al., Curr Opinions in Chem Biology 2007, 11(6):588); Krueger, et al. (2009) Chemistry & Biology 16(3):242; McCullough, et al. (1999) Annual Rev of Biochem 68:255; Liu, et al. (2003) Science 302(5646):868-71; Limbach, et al. (1994) Nucl. Acids Res. 22(12):2183-2196; Wyatt, et al. (1953) Biochem. J. 55:774-782; Josse, et al. (1962) J. Biol. Chem., 237:1968-1976; Lariviere, et al. (2004) J. Biol. Chem. 279:34715-34720; and in International Application Publication No. WO/2009/037473, the disclosures of which are incorporated herein by reference in their entireties for all purposes. Modifications further include the presence of non-natural base pairs in the template nucleic acid, including but not limited to hydroxypyridone and pyridopurine homo- and hetero-base pairs, pyridine-2,6-dicarboxylate and pyridine metallo-base pairs, pyridine-2,6-dicarboxamide and a pyridine metallo-base pairs, metal-mediated pyrimidine base pairs T-Hg(II)-T and C—Ag (I)-C, and metallo-homo-basepairs of 2,6-bis(ethylthiomethyl)pyridine nucleobases Spy, and alkyne-, enamine-, alcohol-, imidazole-, guanidine-, and pyridyl-substitutions to the purine or pyridimine base (Wettig, et al. (2003) J Inorg Biochem 94:94-99; Clever, et al. (2005) Angew Chem Int Ed 117:7370-7374; Schlegel, et al. (2009) Org Biomol Chem 7(3):476-82; Zimmerman, et al. (2004) Bioorg Chem 32(1):13-25; Yanagida, et al. (2007) Nucleic Acids Symp Ser (Oxf) 51:179-80; Zimmerman (2002) J Am Chem Soc 124(46):13684-5; Buncel, et al. (1985) Inorg Biochem 25:61-73; Ono, et al. (2004) Angew Chem 43:4300-4302; Lee, et al. (1993) Biochem Cell Biol 71:162-168; Loakes, et al. (2009), Chem Commun 4619-4631; and Seo, et al. (2009) J Am Chem Soc 131:3246-3252, all incorporated herein by reference in their entireties for all purposes). Other types of modifications include, e.g., a nick, a missing base (e.g., apurinic or apyridinic sites), a ribonucleoside (or modified ribonucleoside) within a deoxyribonucleoside-based nucleic acid, a deoxyribonucleoside (or modified deoxyribonucleoside) within a ribonucleoside-based nucleic acid, a pyrimidine dimer (e.g., thymine dimer or cyclobutane pyrimidine dimer), a cis-platin crosslinking, oxidation damage, hydrolysis damage, other methylated bases, bulky DNA or RNA base adducts, photochemistry reaction products, interstrand crosslinking products, mismatched bases, and other types of "damage" to the nucleic acid. As such, certain embodiments described herein refer to "damage" and such damage is also considered a modification of the nucleic acid in accordance with the present invention. Modified nucleotides can be caused by exposure of the DNA to radiation (e.g., UV), carcinogenic chemicals, crosslinking agents (e.g., formaldehyde), certain enzymes (e.g., nickases, glycosylases, exonucleases, methylases, other nucleases, glucosyltransferases, etc.), viruses, toxins and other chemicals, thermal disruptions, and the like. In vivo, DNA damage is a major source of mutations leading to various diseases including cancer, cardiovascular disease, and nervous system diseases (see, e.g., Lindahl, T. (1993) Nature 362(6422): 709-15, which is incorporated herein by reference in its entirety for all purposes). The methods and systems provided herein can also be used to detect various conformations of DNA, in particular, secondary structure forms such as hairpin loops, stem-loops, internal loops, bulges, pseudoknots, base-triples, supercoiling, internal hybridization, and the like; and are also useful for detection of agents interacting with the nucleic acid, e.g., bound proteins or other moieties.

In certain aspects, methods, compositions, and systems for detection and/or reversal of modifications in a template for single-molecule sequencing are provided, as well as determination of their location (i.e. "mapping") within a nucleic acid molecule. In certain preferred embodiments, high-throughput, real-time, single-molecule, template-directed sequencing assays are used to detect the presence of such modified sites and to determine their location on the DNA template, e.g., by monitoring the progress and/or kinetics of a polymerase enzyme processing the template. For example, when a polymerase enzyme encounters certain types of damage or other modifications in a DNA template, the progress of the polymerase can be temporarily or permanently blocked, e.g., resulting in a paused or dissociated polymerase. As such, the detection of a pause in or termination of nascent strand synthesis is indicative of the presence of such damage or lesion. By analysis of the sequence reads produced prior to the pause or stop in synthesis, and alternatively or additionally after reinitiation of synthesis, one can map the site of the damage or lesion on the template. Since different types of lesions can have different effects on the progress of the polymerase on the substrate, in certain cases the behavior of the polymerase on the template not only informs as to where the lesion occurs, but also what type of lesion is present. Further, in certain embodiments a modification may be bypassed by incorporation of a non-nucleotide binding partner with the lesion in the template strand. For example, abasic sites (e.g., produced by glycosylases) can be "paired" with pyrenes or other similar analogs. (See, e.g., Matray, et al. (1999) Nature 399(6737): 704-8). Such an analog can also be labeled with a detectable label optically distinguishable from those on the nucleotides in the reaction mixture to allow optical detection of its incorporation. Certain aspects of the invention provide a means for reversing such modifications in real time, thereby allowing reinitiation of the sequencing reaction and continued generation of sequence information for the template nucleic acid. Such methods can additionally be used to study effects of various agents (e.g., drugs, chemicals, enzymes, etc.) and reaction conditions on the creation, association with, and/or repair of such lesions and/or damage, as described elsewhere herein. These and other aspects of the invention are described in greater detail in the description and examples that follow.

II. Single Molecule Sequencing

In certain aspects of the invention, single molecule real time sequencing systems are applied to the detection of modified nucleic acid templates through analysis of the sequence and/or kinetic data derived from such systems. In particular, modifications in a template nucleic acid strand alter the enzymatic activity of a nucleic acid polymerase in various ways, e.g., by increasing the time for a bound nucleotide to be incorporated and/or increasing the time between incorporation events. In certain embodiments, polymerase activity is detected using a single molecule nucleic acid sequencing technology. In certain embodiments, polymerase activity is detected using a nucleic acid sequencing technology that detects incorporation of nucleotides into a nascent strand in real time. In preferred embodiments, a single molecule nucleic acid sequencing technology is capable of real-time detection of nucleotide incorporation events. Such sequencing technologies are known in the art and include, e.g., the SMRT™ sequencing and nanopore sequencing technologies. For more information on nanopore sequencing, see, e.g., U.S. Pat. No. 5,795,782; Kasianowicz, et al. (1996) Proc Natl Acad Sci USA 93(24):13770-3; Ashkenas, et al. (2005) Angew Chem Int Ed Engl 44(9):1401-4; Howorka, et al. (2001) Nat Biotechnology 19(7):636-9; and Astier, et al. (2006) J Am Chem Soc 128(5):1705-10, all of which are incorporated herein by reference in their entireties for all purposes. With regards to nucleic acid sequencing, the term "template" refers to a nucleic acid molecule subjected to template-directed synthesis of a nascent strand. A template may comprise, e.g., DNA, or analogs, mimetics or derivatives thereof, as described elsewhere herein. Further, a template may be single-stranded, double-stranded, or may comprise both single- and double-stranded regions. A modification in a double-stranded template may be in the strand complementary to the newly synthesized nascent strand, or may by in the strand identical to the newly synthesized strand, i.e., the strand that is displaced by the polymerase.

The preferred direct methylation sequencing described herein may generally be carried out using single molecule real time sequencing systems, i.e., that illuminate and observe individual reaction complexes continuously over time, such as those developed for SMRT™ DNA sequencing (see, e.g., P. M. Lundquist, et al., *Optics Letters* 2008, 33, 1026, which is incorporated herein by reference in its entirety for all purposes). The foregoing SMRT™ sequencing instrument generally detects fluorescence signals from an array of thousands of ZMWs simultaneously, resulting in highly parallel operation. Each ZMW, separated from others by distances of a few micrometers, represents an isolated sequencing chamber.

Detection of single molecules or molecular complexes in real time, e.g., during the course of an analytical reaction, generally involves direct or indirect disposal of the analytical reaction such that each molecule or molecular complex to be detected is individually resolvable. In this way, each analytical reaction can be monitored individually, even where multiple such reactions are immobilized on a single substrate. Individually resolvable configurations of analytical reactions can be accomplished through a number of mechanisms, and typically involve immobilization of at least one component of a reaction at a reaction site. Various methods of providing such individually resolvable configurations are known in the art, e.g., see European Patent No. 1105529 to Balasubramanian, et al.; and Published International Patent Application No. WO 2007/041394, the full disclosures of which are incorporated herein by reference in their entireties for all purposes. A reaction site on a substrate is generally a location on the substrate at which a single analytical reaction is performed and monitored, preferably in real time. A reaction site may be on a planar surface of the substrate, or may be in an aperture in the surface of the substrate, e.g., a well, nanohole, or other aperture. In preferred embodiments, such apertures are "nanoholes," which are nanometer-scale holes or wells that provide structural confinement of analytic materials of interest within a nanometer-scale diameter, e.g., ~1-300 nm. In some embodiments, such apertures comprise optical confinement characteristics, such as zero-mode waveguides, which are also nanometer-scale apertures and are further described elsewhere herein. Typically, the observation volume (i.e., the volume within which detection of the reaction takes place) of such an aperture is at the attoliter ($10^{-18}$ L) to zeptoliter ($10^{-21}$ L) scale, a volume suitable for detection and analysis of single molecules and single molecular complexes.

The immobilization of a component of an analytical reaction can be engineered in various ways. For example, an enzyme (e.g., polymerase, reverse transcriptase, kinase, etc.) may be attached to the substrate at a reaction site, e.g., within an optical confinement or other nanometer-scale aperture. In other embodiments, a substrate in an analytical reaction (for example, a nucleic acid template, e.g., DNA, RNA, or hybrids, analogs, derivatives, and mimetics thereof, or a target molecule for a kinase) may be attached to the substrate at a reaction site. Certain embodiments of template immobilization are provided, e.g., in U.S. patent application Ser. No. 12/562,690, filed Sep. 18, 2009 and incorporated herein by reference in its entirety for all purposes. One skilled in the art will appreciate that there are many ways of immobilizing nucleic acids and proteins into an optical confinement, whether covalently or non-covalently, via a linker moiety, or tethering them to an immobilized moiety. These methods are well known in the field of solid phase synthesis and microarrays (Beier et al., Nucleic Acids Res. 27:1970-1-977 (1999)). Non-limiting exemplary binding moieties for attaching either nucleic acids or polymerases to a solid support include streptavidin or avidin/biotin linkages, carbamate linkages, ester linkages, amide, thiolester, (N)-functionalized thiourea, functionalized maleimide, amino, disulfide, amide, hydrazone linkages, among others. Antibodies that specifically bind to one or more reaction components can also be employed as the binding moieties. In addition, a silyl moiety can be attached to a nucleic acid directly to a substrate such as glass using methods known in the art.

In some embodiments, a nucleic acid template is immobilized onto a reaction site (e.g., within an optical confinement) by attaching a primer comprising a complementary region at the reaction site that is capable of hybridizing with the template, thereby immobilizing it in a position suitable for monitoring. In certain embodiments, an enzyme complex is assembled in an optical confinement, e.g., by first immobilizing an enzyme component. In other embodiments, an enzyme complex is assembled in solution prior to immobilization. Where desired, an enzyme or other protein reaction component to be immobilized may be modified to contain one or more epitopes for which specific antibodies are commercially available. In addition, proteins can be modified to contain heterologous domains such as glutathione S-transferase (GST), maltose-binding protein (MBP), specific binding peptide regions (see e.g., U.S. Pat. Nos. 5,723,584, 5,874,239 and 5,932,433), or the Fc portion of an immunoglobulin. The respective binding agents for these domains, namely glutathione, maltose, and antibodies directed to the Fc portion of an immunoglobulin, are available and can be used to coat the surface of an optical confinement of the present invention. The binding moieties or agents of the reaction components they immobilize can be applied to a support by conventional chemical techniques which are well known in the art. In general, these procedures can involve standard chemical surface modifications of a support, incubation of the support at different temperature levels in different media comprising the binding moieties or agents, and possible subsequent steps of washing and cleaning.

In some embodiments, a substrate comprising an array of reaction sites is used to monitor multiple biological reactions, each taking place at a single one of the reaction sites. Various means of loading multiple biological reactions onto an arrayed substrate are known to those of ordinary skill in the art and are described further, e.g., in U.S. Ser. No. 61/072,641, incorporated herein by reference in its entirety for all purposes. For example, basic approaches include: creating a single binding site for a reaction component at the reaction site; removing excess binding sites at the reaction site via catalytic or secondary binding methods; adjusting the size or charge of the reaction component to be immobilized; packaging or binding the reaction component within (or on) a particle (e.g., within a viral capsid), where a single such particle fits into the relevant reaction site (due to size or charge of the particle and/or observation volume); using non-diffusion limited loading; controllably loading the reaction component (e.g., using microfluidic or optical or electrical control); sizing or selecting charges in the reaction sites/observation volumes (e.g., the sizes of optical confinements in an array) to control which reaction components will fit (spatially or electrostatically) into which reaction sites/observation volumes; iterative loading of reaction components, e.g., by masking active sites between loading cycles; enriching the activity of the reaction components that are loaded; using self-assembling nucleic acids to sterically control loading; adjusting the size of the reaction site/observation volume; and many others. Such methods and compositions provide for the possibility of completely loading single-molecule array reaction sites (instead of about 30% of such sites as occurs in "Poisson limited" loading methods) with single reaction components (e.g., molecular complexes).

In preferred aspects, the methods, compositions, and systems provided herein utilize optical confinements to facilitate single molecule resolution of analytical reactions. In preferred embodiments, such optical confinements are configured to provide tight optical confinement so only a small volume of the reaction mixture is observable. Some such optical confinements and methods of manufacture and use thereof are described at length in, e.g., U.S. Pat. Nos. 7,302,146. 7,476,503, 7,313,308, 7,315,019, 7,170,050, 6,917,726, 7,013,054, 7,181,122, and 7,292,742; U.S. Patent Publication Nos. 20080128627, 20080152281, and 200801552280; and U.S. Ser. Nos. 11/981,740 and 12/560,308, all of which are incorporated herein by reference in their entireties for all purposes.

Where reaction sites are located in optical confinements, the optical confinements can be further tailored in various ways for optimal confinement of an analytical reaction of interest. In particular, the size, shape, and composition of the optical confinement can be specifically designed for containment of a given enzyme complex and for the particular label and illumination scheme used.

In certain preferred embodiments of the invention, single-molecule real-time sequencing systems already developed are applied to the detection of modified nucleic acid templates through analysis of the sequence and kinetic data derived from such systems. As described below, methylated cytosine and other modifications in a template nucleic acid will alter the enzymatic activity of a polymerase processing the template nucleic acid. In certain embodiments, polymerase kinetics in addition to sequence read data are detected using a single molecule nucleic acid sequencing technology, e.g., the SMRT™ sequencing technology developed by Pacific Biosciences (Eid, J. et al. (2009) *Science* 2009, 323, 133, the disclosure of which is incorporated herein by reference in its entirety for all purposes). This technique is capable of long sequencing reads and provides high-throughput methylation profiling even in highly repetitive genomic regions, facilitating de novo sequencing of modifications such as methylated bases. SMRT™ sequencing systems typically utilize state-of-the-art single-molecule detection instruments, production-line nanofabrication chip manufacturing, organic chemistry, protein mutagenesis, selection and production facilities, and software and data analysis infrastructures.

Certain preferred methods of the invention employ real-time sequencing of single DNA molecules (Eid, et al., supra), with intrinsic sequencing rates of several bases per second and average read lengths in the kilobase range. In such sequencing, sequential base additions catalyzed by DNA polymerase into the growing complementary nucleic acid strand are detected with fluorescently labeled nucleotides. The kinetics of base additions and polymerase translocation are sensitive to the structure of the DNA double-helix, which is impacted by the presence of base modifications, e.g, 5-MeC, 5-hmC, base J, etc., and other perturbations (secondary structure, bound agents, etc.) in the template. By monitoring the activity of DNA polymerase during sequencing, sequence read information and base modifications can be simultaneously detected. Long, continuous sequence reads that are readily achievable using SMRT™ sequencing facilitate modification (e.g., methylation) profiling in low complexity regions that are inaccessible to some technologies, such as certain short-read sequencing technologies. Carried out in a highly parallel manner, methylomes can be sequenced directly, with single base-pair resolution and high throughput.

The principle of SMRT™ sequencing is illustrated in FIG. 1. Two important technology components of certain embodiments of this process are: (i) optical confinement technology that allows single-molecule detection at concentrations of labeled nucleotides relevant to the enzyme, and (ii) phospholinked nucleotides that enable observation of uninterrupted polymerization.

In preferred embodiments, optical confinements are ZMW nanostructures, preferably in an arrayed format. Typically, ZMWs arrays comprise dense arrays of holes, ~100 nm in diameter, fabricated in a ~100 nm thick metal film deposited on a transparent substrate (e.g., silicon dioxide). These structures are further described in the art, e.g., in M. J. Levene, et al., *Science* 2003, 299, 682; and M. Foquet, et A, *J. Appl. Phys.* 2008, 103, 034301, the disclosures of which are incorporated herein by reference in their entireties for all purposes. Each ZMW becomes a nanophotonic visualization chamber for recording an individual polymerization reaction, providing a detection volume of just 100 zeptoliters ($10^{-21}$ liters). This volume represents a ~1000-fold improvement over diffraction-limited confocal microscopy, facilitating observation of single incorporation events against the background created by the relatively high concentration of fluorescently labeled nucleotides. Polyphosphonate and silane-based surface coatings mediate enzyme immobilization to the transparent floor of the ZMW while blocking non-specific attachments to the metal top and side wall surfaces (Eid, et al., supra; and J. Korlach, et al., *Proc Natl Acad Sci USA* 2008, 105, 1176, the disclosures of which are incorporated herein by reference in their entireties for all purposes). While certain methods described herein involve the use of ZMW confinements, it will be readily understood by those of ordinary skill in the art upon review of the teachings herein that these methods may also be practiced using other reaction formats, e.g., on planar substrates or in nanometer-scale apertures other than zero-mode waveguides. (See, e.g., U.S. Ser. No. 12/560,308, filed Sep. 15, 2009; and U.S. Patent Publication No. 20080128627, incorporated herein supra.)

The second important component is phospholinked nucleotides for which a detectable label (e.g., comprising a fluorescent dye) is attached to the terminal phosphate rather than the base (FIG. 1). (See, e.g., J. Korlach, et al., *Nucleos. Nucleot. Nucleic Acids* 2008, 27, 1072, which is incorporated herein by reference in its entirety for all purposes.) 100% replacement of unmodified nucleotides by phospholinked nucleotides is performed, and the enzyme cleaves away the label as part of the incorporation process, leaving behind a completely natural, double-stranded nucleic acid product. Each of the four different nucleobases is labeled with a distinct detectable label to discriminate base identities during incorporation events, thus enabling sequence determination of the complementary DNA template. During incorporation, the enzyme holds the labeled nucleotide in the ZMW's detection volume for tens of milliseconds, orders of magnitude longer than the average diffusing nucleotide is present. Signal (e.g., fluorescence) is emitted continuously from the detectable label during the duration of incorporation, causing a detectable pulse of increased fluorescence in the corresponding color channel. The pulse is terminated naturally by the polymerase releasing the pyrophosphate-linker-label group. Preferably, the removal of the linker and label during incorporation is complete such that the nucleotide incorporated has no remnants of the linker or label remaining. The polymerase then translocates to the next base, and the process repeats.

As shown in FIG. 1A, single DNA polymerase molecules with bound DNA template are attached to a substrate, e.g., at the bottom of each zero-mode waveguide. Polymerization of the complementary DNA strand is observed in real time by detecting fluorescently labeled nucleotides. Reactions steps involved in SMRT™ sequencing are as follows: Step 1: The DNA template/primer/polymerase complex is surrounded by diffusing fluorescently labeled nucleotides which probe the active site. Step 2: A labeled nucleotide makes a cognate binding interaction with the next base in the DNA template that lasts for tens of milliseconds, during which fluorescence is emitted continuously. Step 3: The polymerase incorporates the nucleotide into the growing nucleic acid chain, thereby cleaving the α-β phosphodiester bond, followed by release of the nucleotide. Steps 4-5: The process repeats. A prophetic trace is shown in FIG. 1B that comprises each step shown in 1A. At steps 2 and 4, a fluorescent signal is emitted during binding and incorporation of a nucleotide into the growing nucleic acid chain, and monitoring of these fluorescent signals provides a sequence of nucleotide incorporations that can be used to derive the sequence of the template nucleic acid. For example, a 5'-G-A-3' sequence in the growing chain indicates a 5'-T-C-3' sequence in the complementary template strand.

Figure 2:
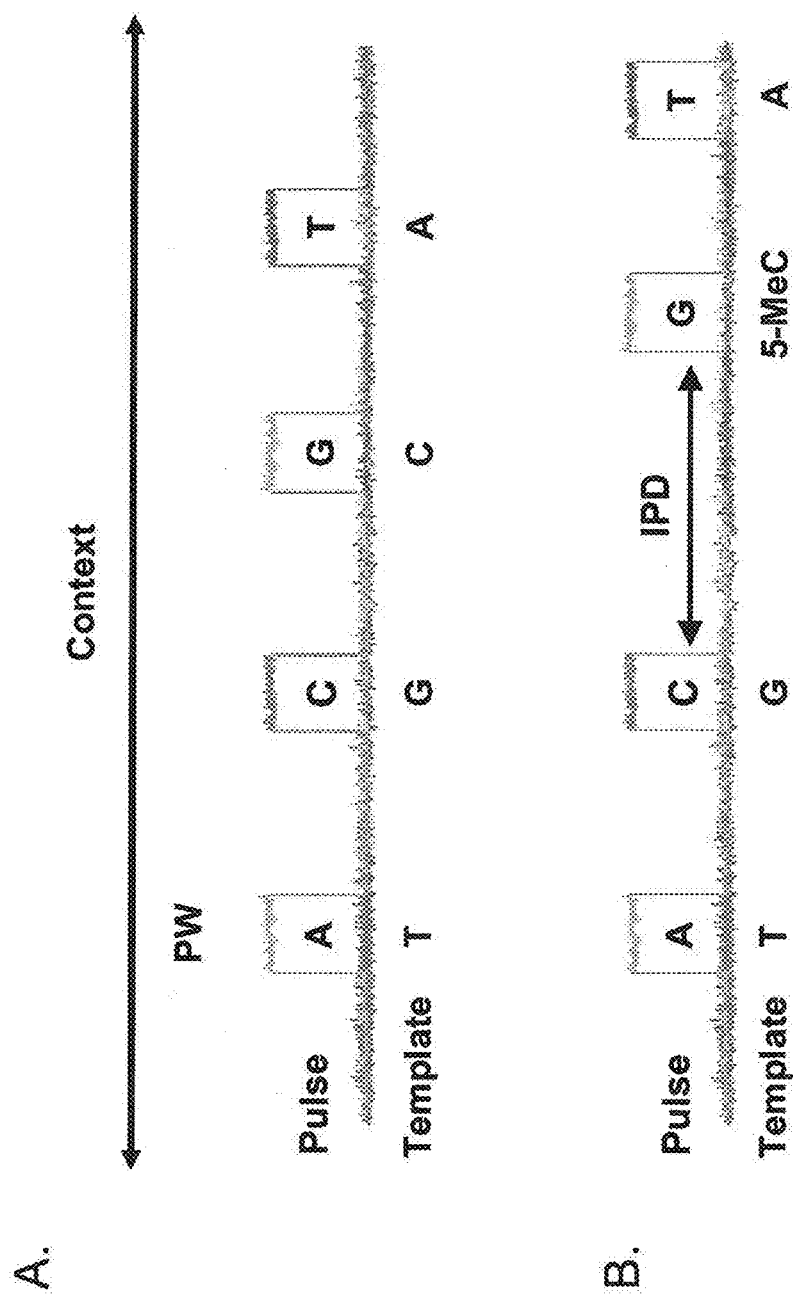
FIG. 2A and FIG. 2B provide illustrative examples of various types of reaction data in the context of a pulse trace.

As described above, reaction data is indicative of the progress of a reaction and can serve as a signal for the presence of a modification in the template nucleic acid. Reaction data in single molecule sequencing reaction reactions using fluorescently labeled bases is generally centered around characterization of detected fluorescence pulses, a series of successive pulses ("pulse trace" or one or more portions thereof), and other downstream statistical analyses of the pulse and trace data. Fluorescence pulses are characterized not only by their spectrum, but also by other metrics including their duration, shape, intensity, and by the interval between successive pulses (see, e.g., Eid, et al., supra; and U.S. Patent Publication No. 20090024331, incorporated herein by reference in its entirety for all purposes). While not all of these metrics are generally required for sequence determination, they add valuable information about the processing of a template, e.g., the kinetics of nucleotide incorporation and DNA polymerase processivity and other aspects of the reaction. Further, the context in which a pulse is detected (i.e., the one or more pulses that precede and/or follow the pulse) can contribute to the identification of the pulse. For example, the presence of certain modifications alters not only the processing of the template at the site of the modification, but also the processing of the template upstream and/or downstream of the modification. For example, the presence of modified bases in a template nucleic acid has been shown to change the width of a pulse and/or the interpulse duration (IPD), either at the modified base or at one or more positions proximal to it. A change in pulse width may or may not be accompanied by a change in IPD. In addition, the types of nucleotides or nucleotide analogs being incorporated into a nascent strand can also affect the sensitivity and response of a polymerase to a modification. For example, certain nucleotide analogs increase the sensitivity and/or response of the enzyme as compared to that in the presence of native nucleotides or different nucleotide analogs, thereby facilitating detection of a modification. In particular, nucleotide analogs comprising different types of linkers and/or fluorescent dyes have been shown to have different effects on polymerase activity, and can impact the incorporation of a base into a nascent strand opposite a modification, and/or can impact the incorporation kinetics for a polynucleotide region proximal to (e.g., upstream or downstream of) the modification. The region proximal to the modification can, in certain embodiments, correspond to the region of the template complementary to the portion of the nascent strand synthesized while the footprint of the polymerase overlapped the locus of the modification. These analog-based differences in polymerase sensitivity and response can be used in redundant sequencing strategies to further enhance the detection of modifications. For example, exchanging nucleotide analogs between iterations of an iterative sequencing reaction elicits changes in polymerase activity between the iterations. Statistical analysis of the differences in the sequencing reads from each iteration combined with the knowledge of how each type of nucleotide analog affects polymerase activity can facilitate identification of modifications present in the reaction. FIG. 2 provides illustrative examples of various types of reaction data in the context of a pulse trace including IPD, pulse width (PW), pulse height (PH), and context. FIG. 2A illustrates these reaction data on a pulse trace generated on an unmodified template, and FIG. 2B illustrates how the presence of a modification (5-MeC) can elicit a change in one of these reaction data (IPD) to generate a signal (increased IPD) indicative of the presence of the modification.

In yet further embodiments, reaction data is generated by analysis of the pulse and trace data to determine error metrics for the reaction. Such error metrics include not only raw error rate, but also more specific error metrics, e.g., identification of pulses that did not correspond to an incorporation event, incorporations that were not accompanied by a detected pulse, incorrect incorporation events, and the like. Any of these error metrics, or combinations thereof, can serve as a signal indicative of the presence of one or more modifications in the template nucleic acid. In some embodiments, such analysis involves comparison to a reference sequence and/or comparison to replicate sequence information from the same or an identical template, e.g., using a standard or modified multiple sequence alignment. Certain types of modifications cause an increase in one or more error metrics. For example, some modifications can be "paired" with more than one type of incoming nucleotide or analog thereof, so replicate sequence reads for the region comprising the modification will show variable base incorporation opposite such a modification. Such variable incorporation is thereby indicative of the presence of the modification. Certain types of modifications cause an increase in one or more error metrics proximal to the modification, e.g., immediately upstream or downstream. The error metrics at a locus or within a region of a template are generally indicative of the type of modification(s) present at that locus or in that region of the template, and therefore serve as a signal of such modification(s). In preferred embodiments, at least some reaction data is collected in real time during the course of the reaction, e.g., pulse and/or trace characteristics.

Although described herein primarily with regards to fluorescently labeled nucleotides, other types of detectable labels and labeling systems can also be used with the methods, compositions, and systems described herein including, e.g., quantum dots, surface enhanced Raman scattering particles, scattering metallic nanoparticles, FRET systems, intrinsic fluorescence, non-fluorescent chromophores, and the like. Such labels are generally known in the art and are further described in Provisional U.S. Patent Application No. 61/186,661, filed Jun. 12, 2009; U.S. Pat. Nos. 6,399,335, 5,866,366, 7,476,503, and 4,981,977; U.S. Patent Pub. No. 2003/0124576; U.S. Ser. No. 61/164,567; WO 01/16375; Mujumdar, et al Bioconjugate Chem. 4(2):105-111, 1993; Ernst, et al, Cytometry 10:3-10, 1989; Mujumdar, et al, Cytometry 10:1119, 1989; Southwick, et al, Cytometry 11:418-430, 1990; Hung, et al, Anal. Biochem. 243(1):15-27, 1996; Nucleic Acids Res. 20(10:2803-2812, 1992; and Mujumdar, et al, Bioconjugate Chem. 7:356-362, 1996; Intrinsic Fluorescence of Proteins, vol. 6, publisher: Springer US, ©2001; Kronman, M. J. and Holmes, L. G. (2008) Photochem and Photobio 14(2): 113-134; Yanushevich, Y. G., et al. (2003) Russian J. Bioorganic Chem 29(4) 325-329; and Ray, K., et al. (2008) J. Phys. Chem. C 112(46): 17957-17963, all of which are incorporated herein by reference in their entireties for all purposes. Many such labeling groups are commercially available, e.g., from the Amersham Biosciences division of GE Healthcare, and Molecular Probes/Invitrogen Inc. (Carlsbad, Calif.)., and are described in 'The Handbook—A Guide to Fluorescent Probes and Labeling Technologies, Tenth Edition' (2005) (available from Invitrogen, Inc./Molecular Probes and incorporated herein in its entirety for all purposes). Further, a combination of the labeling strategies described herein and known in the art for labeling reaction components can be used.

Various strategies, methods, compositions, and systems are provided herein for detecting modifications in a nucleic acid, e.g., during real-time nascent strand synthesis. For example, since DNA polymerases can typically bypass 5-MeC in a template nucleic acid and properly incorporate a guanine in the complementary strand opposite the 5-MeC, additional strategies are desired to detect such altered nucleotides in the template. Various such strategies are provided herein, such as, e.g., a) modification of the polymerase to introduce an specific interaction with the modified nucleotide; b) detecting variations in enzyme kinetics, e.g., pausing, retention time, etc.; c) use of a detectable and optionally modified nucleotide analog that specifically base-pairs with the modification and is potentially incorporated into the nascent strand; d) chemical treatment of the template prior to sequencing that specifically alters 5-MeC sites in the template; e) use of a protein that specifically binds to the modification in the template nucleic acid, e.g., delaying or blocking progression of a polymerase during replication; and f) use of sequence context (e.g., the higher frequency of 5-MeC nucleotides in CpG islands) to focus modification detection efforts on regions of the template that are more likely to contain such a modification (e.g., GC-rich regions for 5-MeC detection). These strategies may be used alone or in combination to detect 5-MeC sites in a template nucleic acid during nascent strand synthesis.

III. Polymerase Modifications

Various different polymerases may be used in template-directed sequence reactions, e.g., those described at length, e.g., in U.S. Pat. No. 7,476,503, the disclosure of which is incorporated herein by reference in its entirety for all purposes. In brief, the polymerase enzymes suitable for the present invention can be any nucleic acid polymerases that are capable of catalyzing template-directed polymerization with reasonable synthesis fidelity. The polymerases can be DNA polymerases or RNA polymerases (including, e.g., reverse transcriptases), DNA-dependent or RNA-dependent polymerases, thermostable polymerases or thermally degradable polymerases, and wildtype or modified polymerases. In some embodiments, the polymerases exhibit enhanced efficiency as compared to the wildtype enzymes for incorporating unconventional or modified nucleotides, e.g., nucleotides linked with fluorophores. In certain preferred embodiments, the methods are carried out with polymerases exhibiting a high degree of processivity, i.e., the ability to synthesize long stretches (e.g., over about 10 kilobases) of nucleic acid by maintaining a stable nucleic acid/enzyme complex. In certain preferred embodiments, sequencing is performed with polymerases capable of rolling circle replication. A preferred rolling circle polymerase exhibits strand-displacement activity, and as such, a single circular template can be sequenced repeatedly to produce a sequence read comprising multiple copies of the complement of the template strand by displacing the nascent strand ahead of the translocating polymerase. Since the methods of the invention can increase processivity of the polymerase by removing lesions that block continued polymerization, they are particularly useful for applications in which a long nascent strand is desired, e.g. as in the case of rolling-circle replication. Non-limiting examples of rolling circle polymerases suitable for the present invention include but are not limited to T5 DNA polymerase, T4 DNA polymerase holoenzyme, phage M2 DNA polymerase, phage PRD1 DNA polymerase, Klenow fragment of DNA polymerase, and certain polymerases that are modified or unmodified and chosen or derived from the phages Φ29 (Phi29), PRD1, Cp-1, Cp-5, Cp-7, Φ15, Φ1, Φ21, Φ25, BS 32 L17, PZE, PZA, Nf, M2Y (or M2), PR4, PR5, PR722, B103, SF5, GA-1, and related members of the Podoviridae family. In certain preferred embodiments, the polymerase is a modified Phi29 DNA polymerase, e.g., as described in U.S. Patent Publication No. 20080108082, incorporated herein by reference in its entirety for all purposes. Additional polymerases are provided, e.g., in U.S. Ser. No. 11/645,125, filed Dec. 21, 2006; 11/645,135, filed Dec. 21, 2006; 12/384,112, filed Mar. 30, 2009; and 61/094,843, filed Sep. 5, 2008; as well as in U.S. Patent Publication No. 20070196846, the disclosures of which are incorporated herein by reference in their entireties for all purposes.

Figure 3:
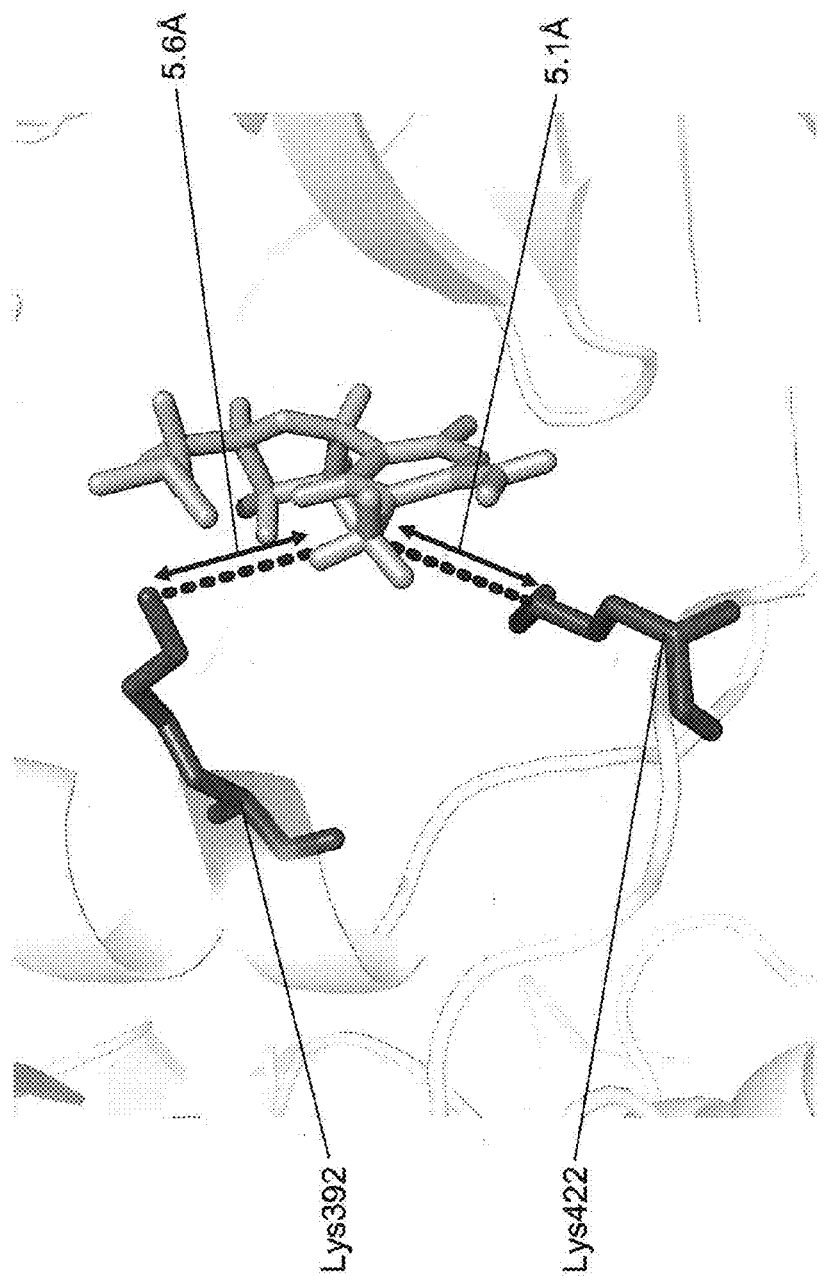
FIG. 3 schematically illustrates a structural model of 5-MeC positioned one base in the 5' direction relative to the DNA polymerase active site.

Further optimization is achieved through improvement of enzyme kinetics, either through the screening of polymerase libraries and/or the engineering of polymerases, which include, e.g., DNA polymerases, RNA polymerases, reverse transcriptases, and the like. In particular, DNA polymerases may be screened to identify those that have desirable properties for detection of nucleic acid modifications described herein. Further, polymerases can be engineered through directed mutagenesis of one or more residues involved in various aspects of template-directed nascent strand synthesis. For example, careful examination of the crystal structure of the polymerase-DNA-nucleotide complex for certain polymerase enzymes has shown that the polymerase rotates and flips out the base on the single-stranded region of the template DNA that is adjacent to the active site in the 5' direction (i.e., the base in the "−1" position). During the subsequent DNA translocation process, this base is flipped into the active site. As such, amino acids that interact with a modified base in the −1 position or during the subsequent tranlocation can be altered or substituted to increase the enzyme's sensitivity to the modified base. In fact, any protein residues that come into close contact with a modification in the template are candidates for substitution or alteration. For example, family B polymerases mostly contain replicative polymerases and include the major eukaryotic DNA polymerases α, δ, ε, and also DNA polymerase ζ. Family B also includes DNA polymerases encoded by some bacteria and bacteriophages, e.g., T4, Phi29, and RB69 bacteriophages. Most family B polymerases share common structural features for DNA binding, and the residues along the DNA primer-template junction and the residues around the base binding pocket at the −1 location (pre-insertion position) can be mutated and the resulting mutants screened for enhanced response to a modification of interest. Specifically, when 5-MeC is in the "flipped-out" (−1) position, it is surrounded by several Φ29 polymerase amino acid residues, such as K392 and K422 which are positioned close to the methyl group (FIG. 3). Mutations such as K392R/W/M and K422R/W/M that substitute the native lysine residue with amino acids with larger side chains (e.g., arginine, tryptophan, or methionine) may increase the polymerase's sensitivity to modified bases, potentially delaying the translocation step and slowing incorporation of the complementary dGTP. This is schematically illustrated with reference to FIG. 3, which shows a structural model of 5-MeC positioned one base in the 5' direction relative to the Φ29 DNA polymerase active site. As shown, two polymerase residues, K392 and K422, are close to the methyl group of 5-MeC. These two residues are potential targets for site-specific mutagenesis to amino acids with larger side chains that will interact sterically with the methyl group. 5-MeC is shown as the chemical structure in the right center, while the K392 and K422 residues are left center.

Any residues that come in close contact with a modified base are candidates for mutation. For example, using molecular morphing and energy minimization to model the translocation path of 5-MeC, a number of protein residues in the Φ29 polymerase have been identified within 5 Å of the methyl moiety as it is being flipped into the active site during the translocation step. The following groups of residues (listed in the order of the translocation path) are targets of mutations to residues with larger side chains: I93, M188, K392, V399, T421, K422; S95, Y101, M102; Q99, L123, K124, T189, A190; G191, S388; P127, L384, N387, S388; and L389, Y390, G391. In particular, I93Y and V399Y may introduce a 5-methylcytosine specific binding region, analogous to those shown by the crystal structures of the SRA/5-methylcytosine binding complex. For example, see G. V. Avvakumov, et al., *Nature* 2008, 455, 822; and H. Hashimoto, et al., *Nature* 2008, 455, 826, the disclosures of both of which are incorporated herein by reference in their entireties for all purposes. Although the residues identified above are specific to the Φ29 polymerase, one of ordinary skill will readily recognize that the structural similarity between the family B polymerases, and to a lesser extent family A polymerases and other polymerases, allows identification of homologous positions on related polymerases as targets for mutation based on the teachings herein.

In addition to the foregoing, additional improvements are derived from a molecular evolution program using these polymerases to enhance their ability to sense 5-MeC. Such programs have already been used to successfully improve large numbers of different enzymes for a variety of applications, including improving DNA polymerases for sequencing. Such methods may include diversification of the amino acid sequence space by mutagenic PCR and DNA shuffling, and/or yeast displays for expression and selection (see, e.g., S. A. Gai, et al., *Curr Opin Struct Biol* 2007, 17, 467; and D. Lipovsek, et al., *Chem Biol* 2007, 14, 1176, which are incorporated herein by reference in their entireties for all purposes, in which ~$10^4$ copies of a recombinant protein are displayed on the surface of a single yeast cell carrying the transgene for the protein. The genotype-phenotype linkage is provided by the yeast cell, but no protein purification is necessary as the displayed proteins have the same properties as bulk solutions of polymerase. With the available infrastructure in house, this program can be initiated without startup costs as soon as polymerase candidates emerge.

IV. Secondary Structure Detection

During single molecule sequencing as described supra, an otherwise highly processive trace is sometimes interrupted by a long pause or complete cessation of sequencing, or other change in the kinetics of the reaction. Such kinetic changes can be caused by secondary structure, e.g., a hairpin loop, supercoiling, internal hybridization, etc. in the template strand. In certain aspects, the invention provides methods for not only identifying secondary structure in a template nucleic acid, but also for improving the overall accuracy of single molecule sequencing.

In certain embodiments, a sequencing read or "trace" is generated by subjecting a template nucleic acid to a real-time, template-directed sequencing reaction. The trace is examined to identify long pauses by finding portions of the trace at which the interpulse duration (IPD) is significantly longer than the average IPD. For example, find pauses that are at least 2-, 3-, 5-, 10-, or 20-times longer than the average IPD. In some embodiments, an IPD averaged over a few neighboring bases is used, in other embodiments an IPD averaged over a window of about 20, 30, 50, 70, or 100 bases is used, and in yet other embodiments, an IPD averaged over all or substantially all of the template is used. It will be understood that a "pause" as used herein includes cases in which the reaction does not reinitiate, e.g., where the reaction is effectively terminated. For example, a polymerase may dissociate or may be unable to translocate past a modification, and the detection of the resulting interruption in sequencing is indicative of the presence of the modification in a template nucleic acid.

The sequence reads generated before and after the pause are analyzed within about a 20-, 30-, 50-, 70-, or 100-base window centered on the pause, and regions that flank the pause site and are complementary to one another are identified. Based upon the complementary sequences, their spacing, and other known factors that impact secondary structure formation (e.g., GC content, pH, salt concentration, and the like), the probability of a hairpin loop at that location in the template is determined. If this probability is high, the sequence reads flanking the pause site are re-examined to identify basecalls that do not match the complementarity of the hairpin, e.g., a non-complementary basecall or missing basecall within a stretch of complementary basecalls. Such non-complementary or missing basecalls have a higher probability of being errors than basecalls in the region that do not interrupt the complementarity between the regions upstream and downstream of the pause site. As such, the basecalls at these positions are reevaluated to determine if the initial basecall was erroneous. Further, knowledge of a given template's propensity for forming secondary structures that interfere with processivity of a polymerase can be used in future rounds of template-directed sequencing of the template to better call base positions in the vicinity of the interfering secondary structure, thereby improving accuracy of basecalls in the future rounds.

Additionally, since the duration of the pause is likely related to the strength of the secondary structure formed within the template, the duration can be used as a metric in determining the type, size, compositions, and likelihood of a secondary structure in the template molecule. Further, other non-limiting examples of kinetic changes that can be indicative of secondary structure in the template include changes in rate, fidelity, processivity, and the amount of non-cognate binding prior to an incorporation event. In addition, for applications in which a single template is repeatedly subjected to template-directed synthesis, the replicate sequence reads that are generated are compared to one another to determine if a given portion of the template consistently produces a pause in the synthesis reaction, which provides further evidence that the pause is due to the sequence context, e.g., secondary structure spontaneously forming in the template.

V. Modified and Non-Natural Nucleotide Analogs and Base Pairing

In certain aspects, methods, compositions, and systems are provided that utilize modified and/or non-natural nucleotide analogs and/or base pairing. For example, certain non-natural nucleotide analogs can be incorporated by a polymerase into a nascent strand opposite a modification, e.g., missing or damaged base. In certain embodiments, such non-natural nucleotide analogs are detectably labeled such that their incorporation can be distinguished from incorporation of a natural nucleotide or nucleotide analog, e.g., during template-directed nascent strand synthesis. This strategy allows real-time sequencing that generates reads that not only provide base sequence information for native bases in the template, but also modified bases without requiring further modifications to the standard methods (Bid, et al, supra). This method facilitates modification profiling in the absence of repeated sequencing of each DNA template, and is particularly well suited to de novo applications. In certain embodiments, the modified or non-natural nucleotide analogs are not incorporatable into the nascent strand and the polymerase can bypass the modification using a native nucleotide or nucleotide analog, which may or may not be labeled. Since the modified or non-natural analog has a higher affinity for the modification than a native analog, it will bind to the polymerase complex multiple times before a native analog is incorporated, resulting in multiple signals for a single incorporation event, and thereby increasing the likelihood of accurate detection of the modification. Similar methods for use in sequencing unmodified template nucleic acids are described in greater detail in U.S. Ser. No. 61/186,661, filed Jun. 12, 2009 and incorporated herein by reference in its entirety for all purposes.

Since 5-MeC retains Watson-Crick hydrogen bonding with guanine, a modified guanine nucleotide analog can be used to detect 5-MeC in the template strand. For example, a guanine nucleotide analog can be constructed to cross the major groove and sense the modified cytosine therein. In particular embodiments, a fused aromatic ring is linked to the N7 atom of the guanine of the nucleotide analog. This modified guanine nucleotide analog can "sense" the methyl group of 5-MeC and affect the base-pairing as compared to an unmodified guanine nucleotide analog. Such guanine nucleotide analogs are further described elsewhere, e.g., in International Application Pub. No. WO/2006/005064 and U.S. Pat. No. 7,399,614. Similar modifications can be made to nucleotide analogs appropriate for SMRT™ sequencing applications, e.g., those with terminal-phosphate labels, e.g., as described in U.S. Pat. Nos. 7,056,661 and 7,405,281; U.S. Patent Pub. Nos. 20070196846 and 20090246791; and U.S. Ser. No. 12/403,090, all of which are incorporated herein by reference in their entireties for all purposes. In certain embodiments, 5-MeC detection may be carried out using a modified guanine nucleotide analog described above that carries a detectable label that is distinguishable from detectable labels on other reaction components, e.g., other nucleotide analogs being incorporated. Such a strategy allows 5-MeC detection by observation of a signal, rather than or in addition to altered polymerase kinetics, which facilitates methylation profiling even in the absence of redundant or replicate sequencing of the template.

Certain embodiments use other non-natural base pairs that are orthogonal to the natural nucleobases pairs. For example, isoguanine (isoG) can be incorporated by a polymerase into DNA at sites complementary to isocytosine (isoC) or 5-methylisocytosine ($^{Me}$isoC), and vice versa, as shown by the following chemical structure and described in A. T. Krueger, et al., "Redesigning the Architecture of the Base Pair: Toward Biochemical and Biological Function of New Genetic Sets."*Chemistry & Biology* 2009, 16(3), 242, incorporated herein by reference in its entirety for all purposes.

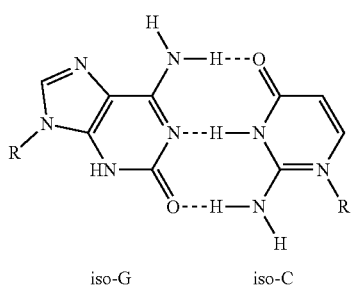

iso-G   iso-C

Other non-natural base pairs that are orthogonal to the natural nucleobases pairs can also be used, e.g., Im-N$^O$/Im-O$^N$ or A*/T* (described further in J. D. Ahle, et al., *Nucleic Acids Res* 2005, 33(10), 3176; A. T. Krueger, et al., supra; and A. T. Krueger, et al., Curr Opinions in Chem Biology 2007, 11(6), 588).

In certain embodiments, a nucleic acid modification to be detected by the methods herein is 7,8-dihydro-8-oxoguanine ("8-oxoG") (also known as 8-oxo-7,8-dihydroguanine, 8-oxoguanine, and 8-hydroxyguanine). 8-oxoG is the major oxidative DNA lesion found in human tissue. Due to the relatively subtle modification to guanine in 8-oxoG, it may be bypassed by replicative DNA polymerases, which preferentially incorporate an adenine nucleotide into the nascent nucleic acid strand at the position where the complementary cytosine should be incorporated, thereby resulting in a mutation in the nascent strand (see, e.g., Hsu, et al. (2004) Nature 431(7005): 217-21; and Hanes, et al. (2006) J. Biol. Chem. 281:36241-8, which are incorporated herein by reference in their entireties for all purposes). As well as introducing mutations in vivo, the bypass of such lesions by a polymerase during template-dependent sequencing reactions introduces errors into the sequence reads generated, and the presence of the damaged guanine nucleotide can also cause base misalignment, potentially adding further errors into a resulting sequence read. DNA synthesis opposite an 8-oxoG lesion has relatively very low specificity (kcat/Km) that is about 10$^6$-fold lower than incorporating a C opposite an unmodified G. See, e.g., Hsu, et al., supra. Further, due to its very low redox potential 8-oxoG can be more easily oxidized than unmodified guanine, and the 8-oxoG oxidation products are very effective blockers of DNA polymerases. See, e.g., Duarte, et al. (1999) Nucleic Acids Res 27(2):496-502; and Kornyushyna, et al. (2002) Biochemistry 41(51): 15304-14, the disclosures of which are incorporated herein by reference in their entireties for all purposes.

It has been shown that 8-oxoG alters both $k_{cat}$ and $K_m$ of steady-state incorporation kinetics, which are likely to cause altered pulse widths and IPD before incorporation of a nucleotide (G or A) into the complementary position in the nascent strand during template-directed sequencing reactions (see, e.g., Hsu, et al. and Hanes, et al., supra). These altered kinetic characteristics can be used to detect 8-oxoG in a template nucleic acid during real-time sequencing reactions. Further, a circular template that comprises both complementary strands of a region of interest (e.g., as described in U.S. Ser. No. 12/383,855 and 12/413,258, both filed Mar. 27, 2009 and incorporated herein by reference in their entireties for all purposes) can be used to repeatedly sequence both strands of a region of interest, thereby generating redundant sequence information that can be analyzed to statistically determine how often a given position in the template has an A-G mismatch as compared to how often the correct base is incorporated at that position. The redundant sequence information increases the accuracy of correctly calling a position as a G or an 8-oxoG. For example, if the mismatch rate is 100%, then if one detects an A at the position, but then a G at the complementary position, then it is highly likely that the A detected was Hoogsteen base pairing with an 8-oxoG in the template. This strategy is similar to detection of 5-MeC modifications that have been deaminated to uracil prior to sequencing, as described in greater detail below.

The mismatch incorporation rate opposite 8-oxoG sites, as well as the degree to which IPD and pulse width are affected by 8-oxoG depend on the type of polymerase used in the reaction (see, e.g., Hsu, et al. and Hanes, et al., supra). As such, polymerase mutants can be designed to have increased kinetic sensitivity to 8-oxoG, or increased/decreased misincorporation rate opposite an 8-oxoG. Methods for designing polymerases for various embodiments of the invention are known in the art and provided elsewhere herein. Further, multiple binding events are very likely at the site of modification, resulting in one or more signals not associated with incorporation into the nascent strand, and these multiple binding events can also occur at positions proximal to the modification, e.g., continuing for a few bases after the site of damage. These additional signaling events would provide a robust indicator of the site of modification. In addition, multiple sequencing reads for the region of the template comprising the modification are expected to contain variable numbers of extra signaling events at or proximal to the modification. As such, comparison of this redundant sequence data will also facilitate identification of loci comprising the modification.

In some aspects, base J is detected and/or mapped in a sample nucleic acid. Base J is a DNA modification found in certain species of trypanosomes, including the one responsible for African sleeping sickness, which afflicts hundreds of thousands of people per year. It is the result of two enzymatic steps. First, thymidine-hydroxylase converts dT into hydroxymethyluracil (HOMedU); second, β-glucosyl-transferase converts HOMedU into base J (β-D-glucosyl-HOMedU or "dJ"). Base J is found predominantly in telomeric repeat genomic regions and is involved in expression of variant surface glycoproteins (VSG), which are important for mammalian host infection. The present invention provides methods for precise mapping of genomic locations of base J that do not require the conventional detection methods of thin layer chromatography, mass spectrometry, or base J-specific antibodies. The single-molecule sequencing-by-incorporation methods described herein facilitate real-time detection of base J in a template during polymerase-mediated nascent strand synthesis. The impact of base J on polymerase activity allow detection of the base in a template nucleic acid, and the sequence data generated during the reaction provides the nucleotide sequence of the region comprising the modified base. Further, sequencing kinetics can also distinguish between. HOMedU and base J in a template, thus providing information about the efficiency and rate of enzymatic conversion from one modified base to the other. As such, such sequencing operations can be used to map precise locations of base J and HOMedU in the trypanosome genome, and this information will help elucidate its role in disease. For more information on base J, see Borst, et at (2008) Annu. Rev. Microbiol. 62:235-51, incorporated by reference herein in its entirety for all purposes.

VI. Chemical Modification of Template

Direct detection of modifications (e.g., methylated bases as described above) without pre-treatment of the DNA sample, has many benefits. Alternatively or additionally, complementary techniques may be employed, such as the use of non-natural or modified nucleotide analogs and/or base pairing described elsewhere herein. In general, such complementary techniques serve to enhance the detection of the modification, e.g., by amplifying a signal indicative of the modification. Further, while the methods described herein focus primarily on detection of 5-MeC nucleotides, it will be clear to those of ordinary skill in the art that these methods can also be extended to detection of other types of nucleotide modifications or damage. In addition, since certain sequencing technologies (e.g., SMRT™ sequencing) do not require amplification of the template, e.g., by PCR, other chemical modifications of the 5-MeC or other modifications can be employed to facilitate detection of these modified nucleotides in the template, e.g., by employing modifying agents that introduce additional modifications into the template at or proximal to the modified nucleotides. For example, the difference in redox potential between normal cytosine and 5-MeC can be used to selectively oxidize 5-MeC and further distinguish it from the nonmethylated base. Such methods are further described elsewhere, and include halogen modification (S. Bareyt, et al., *Angew Chem Int Ed Engl* 2008, 47(1), 181) and selective osmium oxidation (A. Okamoto, *Nucleosides Nucleotides Nucleic Acids* 2007, 26(10-12), 1601; and K. Tanaka, et al., *J Am Chem Soc* 2007, 129(17), 5612), and these references are incorporated herein by reference in their entireties for all purposes.

Glycosylase Modification

By way of example, DNA glycosylases are a family of repair enzymes that excise altered (e.g., methylated), damaged, or mismatched nucleotide residues in DNA while leaving the sugar-phosphate backbone intact. Additional information on glycosylase mechanisms and structures is provided in the art, e.g., in A. K. McCullough, et al., *Annual Rev of Biochem* 1999, 68, 255. In particular, four DNA glycosylases (ROS1, DME, DML2, and DML3) have been identified in *Arabidopsis thaliana* that remove methylated cytosine from double-stranded DNA, leaving an abasic site. (See, e.g., S. K. Ooi, et al., *Cell* 2008, 133, 1145, incorporated herein by reference in its entirety for all purposes.) Furthermore, it has been shown that a 5'-triphosphate derivative of the pyrene nucleoside (dPTP) is efficiently and specifically inserted by certain DNA polymerases into abasic DNA sites through steric complementarity. (See, e.g., T. J. Matray, et al., *Nature* 1999, 399(6737), 704, incorporated herein by reference in its entirety for all purposes.)

Figure 4:
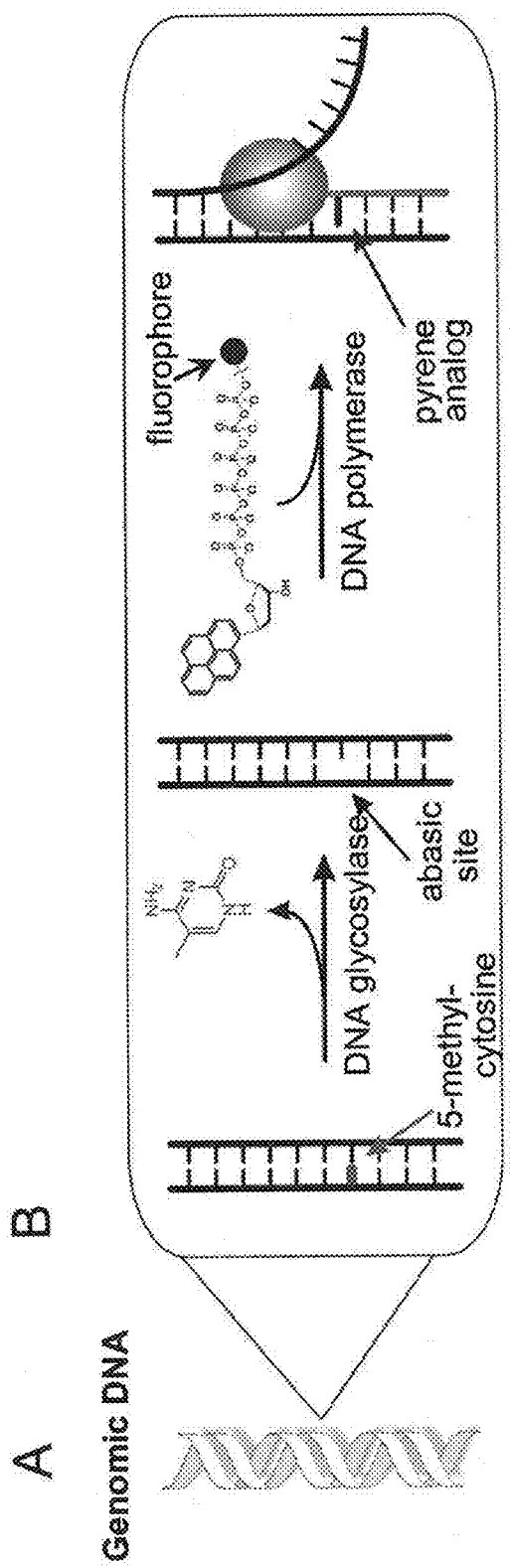
FIG. 4 illustrates an exemplary embodiment of five-base DNA methylation sequencing.

In certain embodiments of single-molecule, five-color DNA methylation sequencing, DNA glycosylase activity can be combined with polymerase incorporation of a non-natural nucleotide analog (e.g., a pyrene analog (dPTP) as shown in FIG. 4). For example, in certain embodiments, methylated cytosines are excised from a DNA sample treated with an *Arabidopsis* DNA glycosylase. Covalent linkage of a fifth fluorophore to the terminal phosphate of dPTP allows detection of abasic sites during polymerase-mediated DNA synthesis.

FIG. 4 shows the principle of five-base DNA methylation sequencing. As shown in FIG. 4A, genomic DNA is fragmented into pieces up to several kilobases in length, which serve as the DNA template. FIG. 4B illustrates DNA glycosylase excising a 5-MeC from the template (black), leaving an abasic site. During SMRT™ sequencing, the DNA polymerase synthesizes the complementary strand and preferentially incorporates a fluorophore-phospholinked pyrene analog opposite the abasic site. This fluorophore has spectral characteristics distinct from those of the other four labeled nucleotides and indicates the presence of a 5-MeC in the original template. Further, error metrics can also be used to identify the modification, e.g., an increase in binding events for the pyrene analog may occur at the abasic site, as well as at downstream positions as the incorporated pyrene analog is "buried" in the nascent strand during subsequent incorporation events. In certain embodiments, a non-hydrolyzable pyrene analog carrying a detectable label is used at a concentration sufficient to bind (and be detected) several times at the abasic site before a hydrolyzable (and, preferably, distinctly labeled) analog is incorporated. Methods using non-hydrolyzable analogs are further described below.

A potential challenge in carrying out the above-described methods is that many DNA glycosylases display some lyase activity, e.g., bifunctional DNA glycosylase/AP lyases. These enzymes can cleave the phosphodiester backbone 3' to the AP (abasic) site generated by the glycosylase activity resulting in an abasic and unsaturated ribose derivative at that site, which could prevent a polymerase from incorporating the pyrene analog complementary to this site. In certain cases, it may be desirable to suppress any lyase activity of the *Arabidopsis* repair enzymes and enhance the desired glycosylase activity. Strategies for achieving this include site directed mutagenesis and the addition of a catalytically inactive AP endonuclease to the glycosylase reaction. (See, e.g., A. E. Vidal, et al., *Nucleic Acids Res* 2001, 29, 1285, incorporated herein by reference in its entirety for all purposes.) A parallel protein mutagenesis program aims to enhance polymerase processivity in the presence of a dPTP analog. Other variations exploit ways in which the kinetics of pyrene incorporation into the abasic site are effected by fluorophore identity, the number of phosphates attached to the pyrene analog, and the structure of the linker connecting the fluorophore to the terminal phosphate group.

In other embodiments of single-molecule, five-color DNA methylation sequencing, DNA glycosylase activity can be combined with addition of a non-natural base (e.g., an otherwise modified cytosine) to replace the methylated base. Briefly, after glycosylase-catalyzed excision of 5-MeC (with or without cleavage of the phosphodiester backbone), a class I or class II AP endonuclease is added to remove the abasic ribose derivative by cleavage at the phosphate groups 3' and 5' to the abasic site, thereby leaving 3'-OH and 5'-phosphate termini. A polymerase capable of extending from the free 3'-OH (e.g., Pol I or human pol β) and a non-natural base (e.g., isoC, isoG, or $^{Me}$isoC) are added to incorporate the non-natural base into the abasic site. A DNA ligase (e.g., LigIII) is added to close the phosphodiester backbone by forming covalent phosphodiester bonds between the free 3'-OH and 5'-phosphates via ATP hydrolysis. Finally, a processive polymerase (e.g., Φ29 DNA polymerase) is used to synthesize a nascent nucleic acid strand complementary to the template strand, where the fifth nucleotide analog is the complement of the non-natural base that replaced 5-MeC in the template. For example, if the replacement base was isoC or $^{Me}$isoC, then the fifth analog would be isoG. As such, the fifth analog would only incorporate into the nascent strand at positions complementary to 5-MeC sites in the template nucleic acid. In preferred embodiments, the fifth analog has a detectable label (e.g., fluorescent dye) that is distinct from labels on other reaction components, e.g, detectable labels on other nucleotide analogs in the reaction mixture. Further, in certain embodiments, a non-natural or altered nucleotide that can base pair with one of the four nucleotide analogs, e.g., A, G, C, or T, can be used to replace the excised base in the template. In such embodiments no fifth fluorophore is required, and the non-natural or altered nucleotide in the template is detected primarily by virtue of the polymerase behavior during template-directed synthesis, as described at length elsewhere herein. This is particularly beneficial where the presence of the excised base causes a smaller response by the polymerase than the presence of the base with which it is replaced. As such, by removing the initial modified base and replacing it with a different modified base at which a polymerase has a more distinct or extreme kinetic signature, the practitioner enhances detection of the modified locus in the template.

Further, glycosylases exist or can be engineered for various DNA modifications, damage, or mismatches, so the methods described above are applicable not only for detection of 5-MeC, but also provide methods for detecting those other types of modifications, as well. Methods for the use of glycosylases for detection of other types of DNA damage are described in U.S. Ser. No. 61/186,661, filed Jun. 12, 2009 and incorporated herein by reference in its entirety for all purposes. In certain embodiments, the pyrene (or similar) nucleotide analog can be non-hydrolyzable to increase the residence time and, therefore, lengthen the emitted signal indicative of the presence of the particular lesion of interest. A non-hydrolyzable fifth-base is eventually displaced by a hydrolysable analog and synthesis of the nascent strand continues. Alternatively, a fifth-base may be hydrolysable but may produce multiple separate signals prior to incorporation to increase the likelihood of detection.

Bisulfite Modification

In certain embodiments, the template may be modified by treatment with bisulfite. Bisulfite sequencing is a common method for analyzing CpG methylation patterns in DNA. Bisulfite treatment deaminates unmethylated cytosine in a single-stranded nucleic acid to form uracil (P. W. Laird, *Nat Rev Cancer* 2003, 3(4), 253; and H. Hayatsu, *Mutation Research* 2008, 659, 77, incorporated herein by reference in their entireties for all purposes). In contrast, the modified 5-MeC base is resistant to treatment with bisulfite. As such, pretreatment of template DNA with bisulfite will convert cytosines to uracils, and subsequent sequencing reads will contain guanine incorporations opposite 5-MeC nucleotides in the template and adenine incorporations opposite the uracil (previously unmethylated cytosine) nucleotides. If a nucleic acid to be treated with bisulfite is double-stranded, it is denatured prior to treatment. In conventional methods, amplification, e.g., PCR, typically precedes sequencing, which amplifies the modified nucleic acid, but does not preserve information about the complementary strand. In contrast, certain embodiments of the present invention include use of a template molecule comprising both strands of a double-stranded nucleic acid that can be converted to a single-stranded molecule, e.g., by adjusting pH, temperature, etc. Treatment of the single-stranded molecule with bisulfite is followed by single-molecule sequencing, and because the template retains both strands of the original nucleic acid, sequence information from both is generated. Comparison of the resulting sequence reads for each strand of the double-stranded nucleic acid will identify positions at which an unmethylated cytosine was converted to uracil in the original templates since the reads from the two templates will be non-complementary at that position (A-C mismatch). Likewise, reads from the two templates will be complementary at a cytosine position (G-C match) where the cytosine position was methylated in the original template. In certain preferred embodiments, a circular template is used, preferably having regions of internal complementarity that can hybridize to form a double-stranded region, e.g., as described in U.S. Ser. No. 12/383,855 and U.S. Ser. No. 12/413,258, both filed on Mar. 27, 2009, and both incorporated herein by reference in their entireties for all purposes.

As described elsewhere herein, methylcytosine has an effect on IPD over a number of neighboring positions when compared to non-methylated cytosine. Uracil compared to thymine is like unmethylated cytosine compared to methylcytosine (i.e. the only difference between U and T is that T has an additional methyl group). Thus, the invention provides methods for performing bisulfite sequencing in which the polymerase kinetics (e.g., IPD and pulse width) or the mismatch incorporation rate are monitored in addition to the actual nucleotides being incorporated. Detection of a change in either of these kinetic parameters or in the mismatch rate at the position in question, or at neighboring positions, is used to determine whether or not a position was always a T or is a U that was originally an unmethylated cytosine.

In certain embodiments, polymerase mutants are designed that are more sensitive to the difference between thymine and uracil in order to enhance the effect described above. Methods for designing polymerase variants are described in detail above and need not be repeated here.

Additionally or alternatively, PCR of uracil-containing oligonucleotides is not necessarily as efficient as PCR without uracil. This issue can bias the PCR amplification of bisulfite-converted DNA. Certain methods of sequencing-by-synthesis using bisulfite-modified templates described herein circumvent this problem by not using PCR amplification. However, the kinetics of these sequencing-by-synthesis reactions can be monitored to detect changes in kinetics due to the presence of uracil residues.

Further, the methods presented herein are useful for detecting PCR bias in the amplification of bisulfite-treated nucleic acids. For example, a few rounds of PCR can be performed on various oligos, some with uracil and some without (including controls with the same sequence but containing thymine in place of uracil). After performing sequencing-by-synthesis on all the resulting oligos, one could determine the percentage of oligos that still contain uracil. If it's different than the expected percentage given ideal (unbiased) PCR amplification, then a bias has been detected.

In yet further embodiments, a template nucleic acid is exposed to a reagent that transforms a modified nucleotide to a different nucleotide structure. For example, a bacterial cytosine methyl transferase converts 5-MeC to thymine (M. J. Yebra, et al., *Biochemistry* 1995, 34(45), 14752, incorporated herein by reference in its entirety for all purposes). Alternatively, the reagent may convert a methyl-cytosine to 5-hydroxy-methylcytosine, e.g., the hydroxylase enzyme TET1 (M. Tahiliani, et al., *Science* 2009, 324(5929), 930, incorporated herein by reference in its entirety for all purposes). In further embodiments, the reagent may include a cytidine deaminase that converts methyl-cytosine to thymine (H. D. Morgan, et al., *J Biological Chem* 2004, 279, 52353, incorporated herein by reference in its entirety for all purposes). In yet further embodiments, a restriction enzyme that specifically alters a modification of interest can be used to create a lesion at the modification site. For example, DPNI cleaves at a recognition site comprising methyladenosine. Optionally, the cleaved template could be repaired during an analytical reaction by inclusion of a ligase enzyme in the reaction mixture. As noted elsewhere herein, nucleotides other than 5-MeC can also be modified and detected by the methods provided herein. For example, adenine can be converted to inosine through deamination, and this conversion affected by methylation of adenine, allowing differential treatment and detection of adenine and MeA.

Another modified base that can be detected using the methods provided herein is 5-hydroxymethylcytosine (5-hmC). It was recently found to be abundant in human and mouse brains, as well as in embryonic stem cells (see, e.g., Kriaucionis, et al. (2009) "The nuclear DNA base 5-hydroxymethylcytosine is present in Purkinje neurons and the brain" *Science* 324 (5929): 929-30; Tahiliani M et al. (May 2009) "Conversion of 5-methylcytosine to 5-hydroxymethylcytosine in mammalian DNA by MLL partner TET1" *Science* 324 (5929): 930-35; and WO/2010/037001, incorporated herein by reference in their entireties for all purposes). In mammals, it can be generated by oxidation of 5-methylcytosine, a reaction mediated by the Tet family of enzymes. Conventional bisulfite sequencing does not effectively distinguish 5-hmC from 5-MeC because 5-hmC tends to remain unmodified like 5-MeC. As such, mass spectrometry is the typical means of detecting 5-hmC in a nucleic acid sample. The methods described herein provide a high-throughput, real-time method to distinguish between C, 5-MeC, and 5-hmC by monitoring deviations from normal polymerase kinetics, including IPD and pulse width.

In certain embodiments, bisulfite conversion can be used in methods for distinguishing 5-MeC from 5-hydroxymethylcytosine (5-hmC). As noted above, bisulfite conversion changes cytosine into uracil and does not change 5-MeC. Bisulfite conversion also changes hydroxymethyl-cytosine (5-hmC) to cytosine-5-methylenesulfonate (CMS), which contains a bulky $SO_3$ adduct in place of the OH adduct of 5-hmC. Like methyl-cytosine, CMS base-pairs with guanine. As such, simply knowing the identity of the base (G) incorporated at a position complementary to a modified base does not alone distinguish between a 5-MeC modified base and a 5-hmC modified base. Furthermore, PCR amplification of hmC-containing oligonucleotides is highly inefficient, which hinders identification of hmC in a template by methods that require PCR amplification prior to detection, at least in part because there will be fewer hmC-containing amplicons produced. The present invention provides strategies that overcome these issues by combining bisulfite conversion with detection of changes in polymerase activity during template-directed nascent strand synthesis. For example, a duplex nucleic acid suspected of containing 5-MeC and/or 5-hmC can be subjected to bisulfite conversion, which converts cytosine to uracil, does not change 5-MeC, and converts 5-hmC to CMS. The template is subsequently subjected to a single-molecule template-directed sequencing reaction. The uracils present in the template (due to bisulfite conversion) can be distinguished from thymines using polymerase behavior, e.g., interpulse duration, pulse width, frequency of cognate sampling, accuracy of pairing, etc. If a complementary strand is also subjected to sequencing, then the complementary nucleotide sequence information can also be used to identify bases, as described above. Further, the $SO_3$ adduct added during the conversion of 5-hmC to CMS will enhance the response of the polymerase to the modified base (e.g., causing increased pausing) and thereby facilitate identification of CMS versus 5-MeC in the template.

As such, in certain embodiments a nucleic acid sample is fragmented and universal primers are attached to each resulting fragment. Bisulfite conversion is performed; the nucleic acid fragments are single-stranded and comprise the primer site, which facilitates subsequent priming and sequencing of the fragments. U is discriminated from T based on polymerase kinetics and standard bisulfite sequencing algorithms, with those bases detected as U known to have originally been C. Bases detected as C based on their base-pairing with G are known to be 5-MeC or CMS (originally 5-hmC). 5-MeC and CMS are discriminated based upon their relatively different kinetics, due at least in part to the $SO_3$ adduct present in CMS and absent in 5-MeC. Further, as with other modification-detection methods, nucleic acids known to have or suspected of having one or more modifications of interest can be targeted, e.g., using antibodies or other binding agents specific to the one or more modifications, and the nucleic acids containing the one or more modifications can be selected or "captured" by various methods known in the art, e.g., immunoprecipitation, column chromatography, bead separations, etc. Once the nucleic acids that do not contain the one or more modifications are removed, e.g., by washing, buffer exchange, etc., the selected nucleic acids can be subjected to template-directed sequencing to identify and/or map the one or more modifications. For additional information on the behavior of 5-hydroxymethylcytosine in conventional bisulfite sequencing, see Huang, et al. (2010) PLoS ONE 5(1):e8888, the disclosure of which is incorporated herein by reference in its entirety for all purposes.

Although methods are described in which bisulfite conversion is used to sequence unamplified nucleic acid templates, the invention also contemplates methods for improving amplification of bisulfite converted nucleic acids. In particular, amplification of bisulfite converted DNA is challenging, at least in part because it is difficult to design primers that can anneal to the converted DNA. This leads to amplification bias and a lower yield of amplicons from certain regions of the original nucleic acid sample. Multiple displacement amplification (MDA) is an isothermal, highly branched amplification technique that utilizes random hexamer primers and strand-displacing polymerases (e.g., phi29). In certain aspects, the present invention provides a method of performing amplification of bisulfite converted nucleic acid using MDA. This avoids the need to design PCR primers since the primers used are randomly generated. In certain embodiments, the primers can be modified to bind to bisulfite converted fragments by replacing the Gs with Ts. (Such modified primers could also be used in conventional PCR.) This strategy could improve the efficiency of and reduce the bias in MDA using post-bisulfite-conversion nucleic acids. The resulting amplicons can be sequenced, e.g., using single-molecule sequencing methods described herein, and compared to sequences generated using unconverted and optionally amplified nucleic acids to identify the modified bases (e.g., 5-MeC or 5-hmC) in the original nucleic acids. Further, the amplicons could be incorporated into circular constructs (e.g., as described in U.S. Ser. No. 12/383,855 and 12/413,258, both filed on Mar. 27, 2009 and incorporated herein by reference in their entireties for all purposes) for iterative sequencing reactions to generate redundant sequence information.

Electrophile Modification of 5-hmC

In certain embodiments, modification of the template by addition of bulky group to 5-hmC facilitates detection of 5-hmC and its discrimination from 5-MeC and unmodified cytosine. In particular, certain electrophilic compounds have been shown to react specifically with hydroxyl groups of nucleic acids under mild conditions in aqueous solution, resulting in addition of a bulky adduct to the nucleic acids. For example, selective acylation of the ribose 2'-hydroxyl position using N-methylisatoic anhydride (NMIA) and selective 2'-hydroxyl acylation analyzed by primer extension (SHAPE) to analyze local tRNA$^{Asp}$ transcript structure in yeast tRNA$^{Asp}$ have been demonstrated. (See, e.g., Merino, et al. (2005) J. Am. Chem. Soc. 127: 4223-4231, which is incorporated herein by reference in its entirety for all purposes.) Additionally, procedures for selective modification of RNA with the spin label N-(2,2',5,5') tetramethyl-3-carboxypyrrolidine-1-oxyl)-imidazole have been developed. This spin label was shown to interact with hydroxyl groups of 5-hydroxymethyl-2 deoxycytidines and the 2' OH ribose groups of polynucleotides and to transfer a bulky adduct to the bases.

Figure 5:
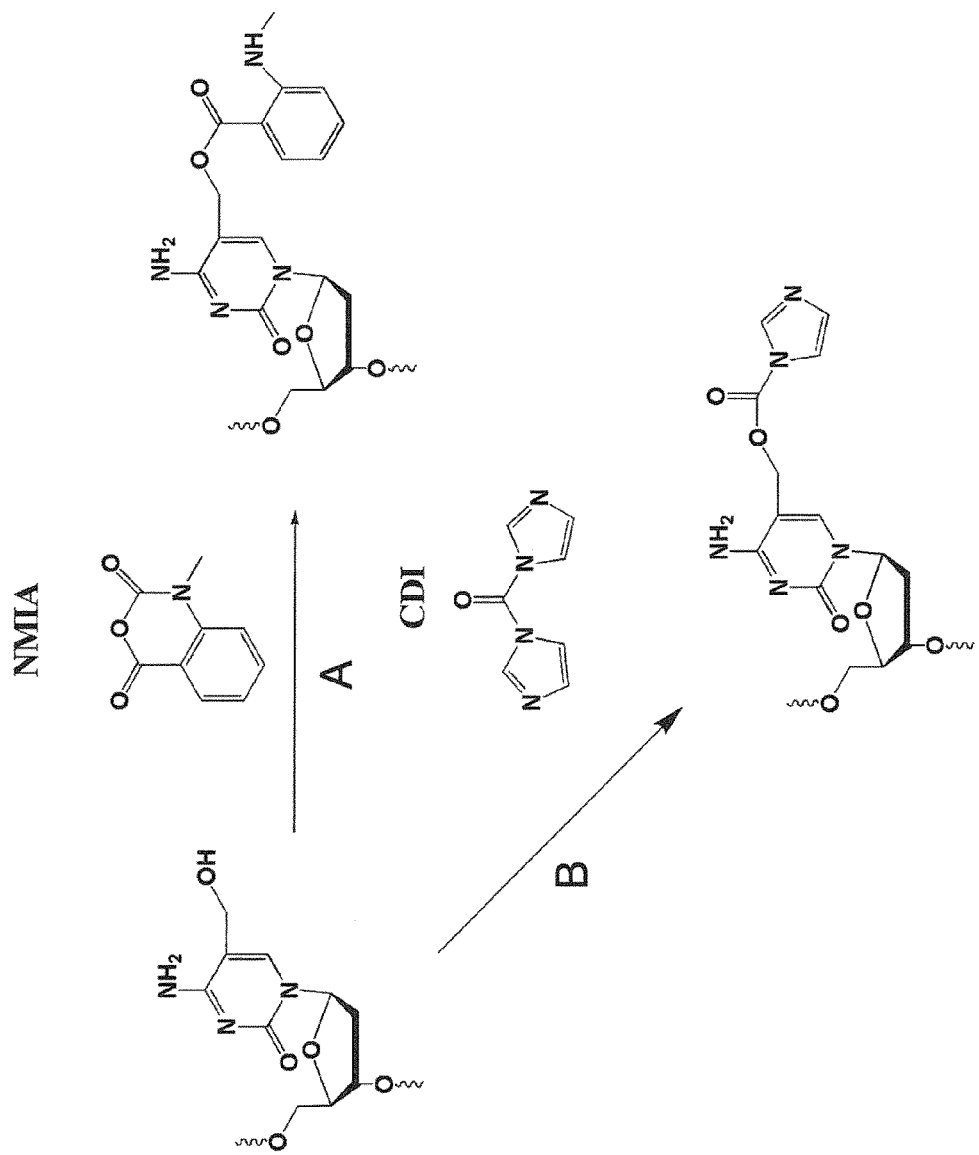
FIG. 5 provides a schematic illustration of addition of bulky adducts to 5-hmC by treatment with NMIA (A) and CDI (B).

The modification did not affect secondary structure, conformation, or template properties in a cell-free system. (See, e.g., Petrov, A. I. (1980) Nuc. Ac. Res. 8(23):5913-5929; Petrov, et al. (1980) Nuc. Ac. Res. 8(18):4221-4234; and Kamzolova, S. G. (1987) Biokhimiia 52(9):1577-82, the disclosures of which are incorporated herein by reference in their entireties for all purposes.) In addition, carbonyldiimidazone (CDI) also reacts with hydroxymethyl groups to transfer a bulky adduct. FIG. 5 provides a schematic showing addition of bulky base adducts to 5-hmC by treatment with NMIA (A) and CDI (B). One potential outcome of the instant methods is the additional modification of terminal phosphate or other hydroxyl groups of a nucleoside. Addition of a bulky group at the OH group of 5-hmC alters the kinetics of the DNA polymerase-mediated incorporation of a nucleoside into a nascent strand opposite the modified 5-hmC, and this alteration facilitates detection and mapping of the 5-hmC within a template nucleic acid. These and other electrophilic compounds known in the art can be used similarly to those described above to add bulky adducts to nucleic acids and, thereby, provide a characteristic kinetic signature during single molecule sequencing reactions that is indicative of the presence of a given base so modified.

Glucosyltransferase Modification

In certain embodiments, DNA glucosyltransferases are used to transfer a glucose group to 5-hmC. DNA glucosyltransferases found in bacteriophage-infected E. coli transfer glucose from uridine diphosphate glucose (UDP-glucose) to hmC nucleotides in DNA. These enzymes are similar to the glucosyltransferase in trypanosomes that converts hydroxymethyluracil to base J, as described above. The enzymes can attach the glucose to hmC through an α or β linkage, as shown here:

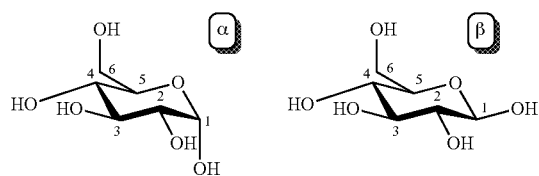

Exemplary enzymes for transferring glucose groups to hmC include, but are not limited to, T2-hmC-α-glucosyltransferase, T4-hmC-α-glucosyltransferase, T6-hmC-α-glucosyltransferase, and T2-hmC-β-glucosyltransferase. Other enzymes can be used to create diglucosylated hmC, such as T6-glucosyl-hmC-β-glucosyltransferase, which creates diglucosylated hmC with a β linkage between the two glucose groups. These enzymes are generally specific for hmC and do not typically alter other bases such as A, C, MeC, T, or G. As such, treating hmC-containing nucleic acids with such enzymes creates nucleic acids in which the hmC residues have been converted to monoglucosylated-hmC or multi-glucosylated-hinC. Glucosylated-hmC is much larger and bulkier than hmC, and therefore has a distinctive effect on polymerase activity when present in a template nucleic acid. Details on the glucosylation of 5-hmC by glucosyltransferases are known in the art, e.g., in Josse, et al. (1962) J. Biol. Chem. 237:1968-1976; and Lariviere, et al. (2004) J. Biol. Chem. 279:34715-34720.

The strategy for addition of glucose moieties to hmC described above can be modified in various ways. For example, currently known glucosylating enzymes (e.g., those that selectively glucosylate hmC or hmU) can be subjected to directed or molecular evolution to introduce mutations that improve the efficiency and/or specificity with which hmC is glucosylated, or that permit addition of adducts other than glucose to hmC. Alternatively or additionally, (a) the glucose adducts added could comprise a detectable label to provide another mode of detection, e.g., in addition to monitoring the kinetics of the reaction, and/or (b) further steps can be performed to add modifications in addition to the glucose adduct, e.g., that are linked to the nucleic acid through the glucose adduct. In yet further embodiments, a glucosyltransferase enzyme can be used that binds to the template but does not dissociate, and therefore results in a further modification (e.g., bound agent) that can be detected during single-molecule sequencing, e.g., by detection of a significant pause of nascent strand synthesis. Methods and strategies for detecting agent-nucleic acid interactions are detailed in section VI, below.

In further embodiments, both hmC and 5-MeC and be modified prior to sequencing. For example, the nucleic acid can be subjected to glucosylation to convert hmC to glucose-hmC, and subsequently the 5-MeC bases can be converted to hmC, e.g., using TET1 protein. Detection of glucose-hmC will be indicative of an hmC in the original nucleic acid, and detection of hmC will be indicative of a 5-MeC in the original nucleic acid. Alternatively, the hmC generated by conversion of 5-MeC can be further modified to produce a greater enhancement of detection while maintaining a signal distinct from that of the glucose-hmC generated by convsersion of hmC in the original nucleic acid. For example, an alpha linkage can be used to attach a glucose moiety to the original hmC, while a beta linkage is used to attach a glucose moiety to the 5-MeC-converted hmC. Alternatively or additionally, a different sugar group can be added to each, e.g., selected from glucose, maltose, sucrose, lactose, galactose, or multiples (e.g., di- or tri-glucosyl (or other sugar) groups) or combinations thereof.

Further, modifications to the template can be performed at many different stages of the method. For example, they can be introduced to a genomic DNA sample before or after fragmentation or shearing; they can be introduced after a nucleic acid fragment is incorporated into a sequencing template; they can be introduced in solution or at the reaction site, e.g., where a reaction component is immobilized; and/or they can be introduced within the reaction mixture, e.g., in the presence of a polymerase or other sequencing enzyme.

DMS Modification

In certain embodiments, the template may be modified by treatment with dimethyl sulfate (DMS) prior to sequencing. DMS is a chemical that methylates the N7 position of guanine in dsDNA, and to a lesser extent the N3 position of adenine in dsDNA. If proteins are bound to a DNA treated with DMS, the proteins will block the methylation of the sequences to which they are bound. The bound proteins can then be removed and the DNA treated with piperidine, which breaks the DNA backbone by removal of the methylated bases. Protected regions of the DNA are identified as having been bound to the proteins during the DMS treatment. DMS also modifies the N3 position of cytosine and the N1 position of adenine in single-stranded DNA or RNA so these bases can no longer base pair with their complement. Since both these positions are involved in base-pairing, regions that are double-stranded during DMS treatment are protected from modification. Reverse transcriptase PCR and gel analysis is subsequently used to identify regions that were unmodified, and are therefore likely regions that adopt secondary structures that protect them from DMS treatment.

The present invention provides methods for real-time, single-molecule sequencing of nucleic acids that have been subjected to DMS treatment as a means for detecting both binding sites of nucleic acid binding agents, as well as sites of secondary structure formation, e.g., G-quadruplex structures (also known as G-tetrads or $G_4$-DNA; see, e.g., Zheng, et al. (2009) "Molecular crowding creates an essential environment for the formation of stable G-quadruplexes in long double-stranded DNA," Nuc Ac Res 1-12, incorporated herein by reference in its entirety for all purposes). For example, dsDNA bound to one or more nucleic acid binding agents is subjected to DMS treatment, and the binding agents are subsequently removed. The resulting dsDNA is subjected to template-directed sequencing and pulse metrics are monitored to identify locations where guanine or adenine were methylated. For example, A and G template nucleotides that cause a distinguishable change in one or more pulse metrics are identified as not having been bound by the agent(s), and A and G template nucleotides that do not cause a distinguishable change in one or more pulse metrics are identified as having been bound by the agent(s). In certain embodiments, the DMS treatment takes place in vivo, and the dsDNA is subsequently extracted and sequenced to study transcription factor binding in the cell. Alternatively, dsDNA can be extracted from cells and subsequently exposed to one or more nucleic acid binding agents prior to treatment with DMS in vitro. The DMS treatment can performed in solution, or can be performed after the dsDNA is immobilized, e.g., at a reaction site. The nucleic acid binding agents that can be studied include, but are not limited to, transcription factors, polymerases, ribosomes, and associated cofactors to DNA. Investigators can thereby study which DNA regions are being actively transcribed in different cells, in healthy vs. diseased tissue, in different cell cycle stages, in response to various environmental stimuli, and the like. For example, in certain embodiments DMS is applied in vivo or in vitro to mRNAs bound by actively translating or stalled ribosomes. The resulting mRNA templates are subsequently sequenced in real time, and the reactions are monitored for altered kinetics, which are indicative of modified bases. Alternatively, the DMS-treated mRNAs can be heated to degrade modified regions, leaving only unmodified regions for sequencing. The sequence data so generated is used to identify the mRNAs to which a ribosome was bound, and therefore the mRNAs that were being actively translated in the sample from which they were extracted. Other methods of ribosome profiling are known in the art, e.g., Ingolia, et al. (2009) Science 324 (5924):218-23, the disclosure of which is incorporated herein by reference in its entirety for all purposes.

In further embodiments, DNA and RNA secondary structure profiling can be performed by applying DMS to single-stranded DNA or RNA (e.g., mRNA, siRNA, microRNA, rRNA, tRNA, snRNA, ribozymes, etc.) and sequencing the DMS-modified nucleic acid using an appropriate polymerase. (Methods for sequencing RNA molecules using RNA dependent polymerases are described in detail in U.S. Ser. No. 61/186,661, filed Jun. 12, 2009 and incorporated herein by reference in its entirety for all purposes.) Regions of the treated nucleic acid that elicit altered polymerase kinetics are identified as regions that were single-stranded during the DMS treatment, and regions of the treated nucleic acid that do not elicit altered polymerase kinetics are identified as regions that were double-stranded during the DMS treatment and therefore likely contained duplex secondary structure, e.g., hairpins. In certain embodiments, the nucleic acid is heated prior to sequencing to cause degradation of the modified regions. The remaining, undegraded nucleic acid is subsequently subjected to sequencing and the sequence data so generated is used to identify regions of the original nucleic acid that formed secondary structures that prevent DMS modification.

DMS modification can also be used to map regions that form non-B-form secondary structures, some of which have regulatory roles in vivo. For example, G-quadruplexes consist of stacks of Gs that protect the guanosines from DMS-modification, even in the absence of a nucleic acid binding agent. Subsequent sequence analysis is used to identify regions that were protected from DMS modification, and therefore are likely to have had some protective secondary structure.

Further, although described primarily in terms of DMS modification, other types of chemical and/or enzymatic modifications can also be used in an analogous fashion, as will be clear to one of ordinary skill in the art based on the teachings herein. For example, other methods of DNA or RNA footprinting are particularly useful in the methods herein, including, e.g., use of DNaseI, hydroxyl radicals, UV crosslinking between an agent and a nucleic acid to which it is bound, or UV irradiation for cleavage of nucleic acid that is not bound by an agent. Such methods are described more fully in the published literature and elsewhere herein.

The template altered by exposure to the reagent is sequenced, e.g., using a real-time, single-molecule methodology such as SMRT™ sequencing. In certain preferred embodiments, the sequencing is performed multiple times on the same template, e.g., by rolling-circle synthesis or another form of molecular redundant sequencing. The loci in the template containing altered nucleotides are identified by analysis of the resulting sequence reads. In cases in which the 5-MeC nucleotides were converted to non-altered nucleotide (e.g., thymine), molecular redundant sequencing on both the forward and reverse strands is useful for further refining the identification of the altered nucleotides since the transformation disrupts the normal Watson-Crick base pairing. For example, if MeC•G pair is converted to T•G, the forward and reverse reads will show non-complementary nucleotides at that position (A and C), indicating that the base pair in the template was non-standard, likely due to an alteration of a 5-MeC at that position. Methods for molecular redundant sequencing are further described in U.S. Pat. No. 7,476,503 and U.S. application Ser. Nos. 12/383,855 (filed Mar. 27, 2009), 12/413,258 (filed Mar. 27, 2009), 12/413,226 (filed Mar. 27, 2009), and 12/561,221 (filed Sep. 16, 2009), all of which are incorporated herein by reference in their entireties for all purposes.

Maintenance Methyltransferases

In certain situations, such as when the amount of sample nucleic acid is limiting, it is desirable to amplify the nucleic acid sample to increase the number of template molecules that can be subjected to analysis. However, as noted above, conventional amplification strategies such as PCR may not maintain modifications in the original nucleic acid sample, and the resulting amplicons would therefore lack the modifications. For example, methylation patterns in a template nucleic acid are not reproduced in amplicons from a PCR reactions. After a first round, the resulting amplicons are hemimethylated, and after a second round amplicons are produced that are entirely unmethylated from the nonmethylated strands synthesized in the first round. In each subsequent round, a greater majority of fully unmethylated strands are produced, effectively erasing the methylation pattern from the original nucleic acid. The present invention provides strategies for amplification of modification-containing nucleic acid template that maintain the modification in the amplicons so produced.

In some embodiments, a methylation pattern present in an original nucleic acid is maintained in amplicons produced in an amplification reaction. Maintenance methyltransferases function in an organism to ensure that methylation patterns are maintained during genome replication by catalyzing the transfer of a methyl group, e.g., from S-adenosyl methionine (SAM), to an unmethylated strand of a hemimethylated duplex. For example, DNMT1 predominantly methylates CpG di-nucleotides in hemimethylated portions of the mammalian genome, although it also has some activity on unmethylated DNA. This enzyme can be included in a reaction in which a methylated nucleic acid is being amplified, and during the amplification DNMT1 would methylate nascent strands at loci opposite the methylation in the parent strands. Additionally or alternatively, other types of maintenance methyltransferases can be included in the amplification reaction, e.g., E. coli DNA adenine methyltransferase (Dam). For standard PCR, either a thereto-stable form of the methyltransferase can be used, or fresh methyltransferase can be added between each cycle. Alternatively, isothermal amplification, such as multiple displacement amplification or loop-mediated isothermal amplification (LAMP) can be performed. For a review of a variety of isothermal amplification techniques, see Gill, et al. (2008) Nucleosides, Nucleotides & Nucleic Acids 27(3):224-243, the disclosure of which is incorporated herein by reference in its entirety for all purposes.

In some embodiments, a fusion protein comprising a polymerase and a modifying agent is used to introduce additional modifications to the template during a polymerase reaction. For example, the modifying agent could be linked to the polymerse in an orientation to associate with the template and introduce modifications ahead of the polymerase enzyme. As such, the modifications so introduced would be encountered by the polymerase and would elicit a response indicative of the presence of the modification. Alternatively, the modifying agent can bind to the template ahead of the polymerase, which would also produce a detectable kinetic response from the enzyme as it is either blocked by the bound modifying agent, or must displace it. Likewise, the modifying agent can bind to the duplex formed by the polymerse, and thereby cause a change in polymerase activity by serving as an "anchor," at least until it dissociates. It will be clear to one of ordinary skill in the art that various different modifying agents can be fused to the polymerse, including, but not limited to glycosylases, glucosyltransferases, hydroxylases (e.g., TET1), maintenance methyltransferases, and other agents that associate with and/or introduce nucleic acid modifications.

In further embodiments, a nucleic acid sample can be divided into aliquots, each of which is subsequently subjected to a different treatment (including "no treatment") prior to sequencing. For example, one aliquot may be left untreated while another is subjected to glucosylation, glycosylation, chemical modification, etc. The sequence data generated from the different aliquots is analyzed and compared, and differences in the sequence reads are indicative of modifications in the original template and/or in the modified template. For example, a genomic sample suspected of comprising 5-MeC and/or hmC nucleobases can be split into two aliquots, A and B. Aliquot A is treated with a glucosyltransferase to convert all hmC nucleobases to glucose-hmC, and is subsequently sequenced. Aliquot B is subjected to TET1 treatment to convert 5-MeC nucleobases to hmC, followed by treatment with a glucosyltransferase to convert all hmC (including those in the original nucleic acid sample) to glucose-hmC. After the two conversion steps, aliquot B is sequenced. The kinetic signatures from the sequencing of the nucleic acids in aliquot A are compared to the kinetic signatures from the sequencing of the nucleic acids in aliquot B. Those loci that have glucose-hmC in both aliquots were originally hmC, and those loci that have glucose-hmC in only aliquot B were originally 5-MeC. In this way, the distinct kinetic signature associated with hmC during single-molecule sequencing can be used to identify both hmC and 5-MeC within a nucleic acid sample.

VII. Detection of Agent-Nucleic Acid Interactions

Another example of a biological process that may be monitored in accordance with the invention is association of a nucleic acid binding agent (e.g., a protein, nucleic acid, or small molecule) with a single nucleic acid molecule. As for the chemical modifications to the template described above, use of such agents can serve to enhance the detection of the modification, e.g., by amplifying a signal indicative of the modification. Further, the methods are useful for mapping binding sites of binding agents that bind to a natural or unmodified nucleotide in a nucleic acid molecule. Many types of agents bind to nucleic acids, such as transcription factors, RNA and DNA polymerases, reverse transcriptases, histones, nucleases, restriction enzymes, replication protein A (RPA), single-stranded binding protein (SSB), RNA-binding proteins, microRNA-containing ribonucleoprotein complexes, anti-DNA antibodies, DNA damage-binding agents, modifying agents, agents that bind altered nucleotides (e.g., methylated), small RNAs, microRNAs, drug targets, etc. In particular, transcription factors are involved in gene expression regulation and are thus very important for the study of diseases such as cancer. Further, RPA binds single-stranded DNA during replication to keep DNA unwound and accessible to the polymerase. Current technologies for detecting the binding of a protein transcription factor to a DNA molecule involve bulk detection. Certain aspects of the invention provide methods for detecting the binding of a transcription factor or other nucleic acid binding agent to a single molecule of DNA. In some embodiments, the binding agents are detected while bound to a nucleic acid template; in some embodiments the positions at which the binding agents were associated are detected after the binding agents have dissociated or been removed from the template. The advantages of the methods described herein include, but are not limited to, improved resolution of kinetics (e.g., of association and dissociation), binding loci, and statistical analysis; and greater sensitivity and simplicity.

In certain aspects, the invention provides detection of binding of a nucleic acid binding agent onto a single nucleic acid molecule through a technology that involves observing the activities of single molecules of polymerases in real time and with high multiplex capabilities, thereby allowing the screening of multiple nucleic acid binding agents (or other components of the reaction) with high throughput. In particular, the invention employs analogous processes used for single-molecule, real-time DNA sequencing, and with some modifications, exploits such processes to characterize various aspects of binding of nucleic acids by proteins of interest. Such sequencing technology has been previously described, e.g., in Eid, et al. (incorporated herein above). In certain preferred embodiments, one or more components of the reaction are immobilized at a reaction site, e.g., in an optical confinement such as a ZMW. Alternatively or additionally, multiple reactions can be simultaneously monitored by immobilizing them at discrete, preferably optically resolvable, locations on a substrate, e.g. in an array of optical confinements. Further, to prevent displacement of the agent prior to a detectable affect on the reaction (e.g., a pause), the binding may be enhanced through various alterations to the reaction mixture (e.g., salt concentration, pH, temperature, etc.), or through alterations to the agent itself. For example, a DNA-binding protein may comprise various mutations that enhance binding under the conditions of the sequencing reaction, e.g., by lowering the Kd of the binding domain (e.g., a methyl binding domain) or by duplicating the domain to increase the effective concentration of the binding domain in the vicinity of the DNA template.

In certain preferred embodiments, a single nucleic acid template is bound to a sequencing engine (e.g., a polymerase or reverse transcriptase) that is synthesizing a nascent nucleic acid strand, e.g., during a template-directed sequencing reaction or a sequencing-by-synthesis reaction. The template can be any nucleic acid template appropriate for template-directed sequencing, e.g. single-stranded or double-stranded DNA, RNA, or a DNA/RNA hybrid. Further, the nucleic acid template can be linear or circular. For example, a dsDNA template can be bound by a polymerase in an optical confinement, e.g., a ZMW, as described above and in, e.g., Foquet, et al., and Levene, et al., both of which are incorporated herein supra. A nucleic acid binding agent, such as a transcription factor or DNA damage-binding agent, is added to the reaction mixture under conditions that promote binding of the agent to the template. If the template is bound by the agent in a location ahead of the polymerase, the bound agent impedes the translocation of the polymerase along the template, resulting in a pause or full stop in polymerization at or adjacent to the position at which the agent bound. Real-time monitoring of the ongoing sequencing reaction will allow detection of the pause or stop, which is indicative of (i) the fact that the agent bound the template, and (ii) the position on the template that was bound by the agent, e.g., based on the sequence of nucleotides incorporated immediately prior to the pause or stop. Further, a consensus sequence for the binding site of the agent can be determined by statistical analysis of the "binding-affected" (e.g., containing a pause or truncated) sequence reads generated in the presence of the agent and the non-binding-affected (e.g., full-length) sequence reads generated in the absence of the agent. For example, truncated sequence reads (or sequence reads having detectable pauses) generated in the presence of the agent provide a location on the template at which the polymerase was blocked, and full-length reads generated in the absence of the agent provide the binding site sequence. In certain embodiments, sequence reads from the region of the template immediately downstream of the point at which the polymerase is blocked are analyzed together to find a sequence (specific or degenerate) they have in common, and this common sequence is identified as the consensus binding site for the agent. Such analyses are routine in nucleic acid sequence analysis and require no further elaboration here.

In certain embodiments, a nucleic acid binding protein of interest is introduced into a reaction mixture comprising a pool of nucleic acid templates. The pool of templates is exposed to the protein under conditions that promote binding, and polymerase enzymes are subsequently added to the reaction mixture and allowed to bind the templates, e.g., at a single-stranded region comprising a bound oligonucleotide primer. The reaction mixture further comprises a set of detectably labeled nucleotides, wherein each type of nucleotide in the set is linked to a distinct label that is optically identifiable during polymerization, thereby providing a distinct signal for each nucleotide incorporation event that identifies the base incorporated into the nascent strand. The polymerase-template complexes are immobilized on a substrate such that signals emitted from each complex are optically resolvable from signals emitted from every other complex on the substrate. Preferably, the reaction mixture is lacking a component required for polymerization to prevent polymerase activity prior to immobilization. Such a component is subsequently added to the reaction mixture allowing the polymerase to commence synthesis of a nucleic acid strand complementary to the template to which it is bound. For those templates that were not bound by the protein, synthesis continues unimpeded and the template is fully sequenced in the optical confinement, generating a full-length sequence read for the template. In contrast, the templates that were bound by the protein are processed by the polymerase until the bound protein is encountered on the template, at which time the polymerase will pause or stop polymerizing the complementary strand. The truncated sequence read generated from such a stalled polymerase-template complex will provide sequence information for the template upstream of the protein binding site. Statistical analysis of this sequence information, both at the single molecule level and across the pool of templates, can be used to both identify the particular nucleic acid templates bound (or not bound) by the protein, as well as identifying the position at which the protein binds. For example, this technique can be used to map specific protein binding sites on the template, e.g., sequence-specific or lesion/damage-specific binding sites.

This assay can by easily modified to test the impact of various reaction conditions, e.g., pH, ionic strength, temperature, ion concentrations (e.g., divalent metal ion concentrations), and presence or absence of agents such as drugs, antibodies, or binding competitors. Other reaction condition variations that can affect incorporation kinetics include the number of phosphates attached to a nucleotide analog to be incorporated into a nascent strand, and the structure of the linker connecting a fluorophore to a phosphate group, e.g., a terminal phosphate group. These tests can be used to identify optimal reaction conditions, e.g., for causing a pause or stop in an ongoing sequencing reaction or for binding to a particular subset of the pool of template nucleic acids. Further, the assay can be used to test variants and/or mutants of known nucleic acid binding proteins to screen such mutants for desired characteristics, such as binding under stringent conditions or having altered sequence specificity for binding. The assay can also be used to test variants and/or mutants of polymerase enzymes for desired characteristics, such as the ability to bypass a particular nucleic acid binding protein. Further, the specificity of binding can be explored by performing the assay with different pools of nucleic acid templates.

In certain embodiments, the nucleic acid binding protein is a transcription factor (TF) with a specific consensus binding sequence, e.g., TGACTCA for AP1 or GGACTTCC for NF-κB. DNA template molecules that contain the consensus binding sequence are bound by the TF at that sequence, and those that do not are not bound by the TF. When the translocating polymerase encounters a bound TF, the polymerase stops polymerizing, and the cessation of signals emitted from the complex is indicative that the TF bound the template and, therefore, that the template contains the consensus binding sequence. As noted above, various reaction conditions can be tested for their effect on either the binding of the TF or the ability of the polymerase to bypass it or displace it from the template.

Statistical analysis of the sequence information from DNA templates that were bound by a TF can be used to further characterize the TF, e.g., by (i) identifying genes targeted by the TF, e.g., using publicly available genome sequence data; (ii) identifying the consensus binding sequence, e.g., using sequence data generated from the same templates in the absence of the TF; (iii) studying the interaction of multiple transcription factors; (iv) modulation of TF binding by other proteins, small molecules, etc.; (v) testing the temperature sensitivity of binding; (vi) identifying and characterizing the abundance of particular DNA-binding proteins, e.g., in a cell extract; and the like. For example, the identity and abundance of DNA-binding proteins can be compared between a) different tissues, cell lines, cell developmental stages, species, or subspecies; b) healthy and diseased samples; and c) in the presence and absence of environmental stressors and/or various agents (e.g., drugs, toxins, etc.). Yet further, variants and mutants of different components of the reaction mixture, TF, polymerase, template, etc., can be tested to identify those with particularly desirable characteristics, e.g., tight binding, protein displacement activity, non-consensus binding sequences with higher binding affinity to the TF, etc.

Mapping of Previously Bound Agents

In certain aspects, the invention provides methods to map binding sites on a nucleic acid after a binding agent has dissociated or been removed from the nucleic acid. In certain preferred embodiments, a binding/modifying agent introduces one or more modifications to the nucleic acid that can be detected during single-molecule sequencing after the agent is no longer associated with the nucleic acid. For example, such a binding/modifying agent can be a complex between a binding agent and a modifying agent that introduces one or more modifications into a nucleic acid molecule to which the binding agent is associated. After the one or more modifications are introduced, the binding/modifying agent is removed from the nucleic acid molecule, and the modifications are detected during single-molecule sequencing to map the portion(s) of the nucleic acid molecule at which the binding agent was previously associated, e.g., using both the sequence data and the polymerase activity during the reaction. In certain preferred embodiments, the binding agent is a transcription factor and the modifying agent introduces a modification (e.g., methyl group, sugar group, damage, etc.) at one or more nucleotides within or near the binding site of the transcription factor. For example, DamID is a technique in which a transcription factor-Dam methyltransferase fusion protein is used to map binding sites for the transcription factor by exposing a nucleic acid sample to the fusion protein under conditions in which binding and conversion of adenosine to $N^6$-methyladenosine occurs, and detecting the methylated bases by methylation-sensitive PCR. (See, e.g., van Steensel, et al. (2000) Nat. Biotechnol. 18(4):424-428; van Steensel, et al. (2001) Nat. Genet. 27(3):304-308; Orian, A. (2006) Curr. Opin. Genet. Dev. 16(2):1-8; Moorman, et al. (2006) Proc. Natl. Acad. Sci. USA 103(32):12027-12032; and Greil, et al. (2006) Methods Enzymol. 410:342-359, all of which are incorporated herein by reference in their entireties for all purposes.) The present invention improves upon this method, at least in part, with more efficient and high-throughput methods for detection of the modified bases during single-molecule sequencing, in which the transcription factor's binding site is mapped at the same time as a nucleic acid molecule to which it is or was bound is being sequenced. Single-molecule sequencing of $N^6$-methyladenosine is further described elsewhere herein.

In certain embodiments, the methods herein are also useful for examining the affinity of binding agent (e.g., transcription factor, histone, etc.) association with different nucleic acid sequences within a single reaction mixture. For example, a nucleic acid preparation (e.g., genomic DNA) is exposed to a limiting amount of a particular binding/modifying agent subsequently sequenced to identify not only the modified bases but also the one or more binding sites to which the agent bound. This sequence data is compared to the nucleic acid sequence of the nucleic acid preparation sans modification to determine the frequency of the binding sites within the preparation. These data are analyzed to determine the affinity of the binding agent for each binding site. For example, binding sites that are rare in the nucleic acid preparation but are frequently bound by the binding/modifying agent are identified as those to which the binding agent has a high affinity. Likewise, binding sites that are common in the nucleic acid preparation but are infrequently bound by the binding/modifying agent are identified as those to which the binding agent has a low affinity.

Binding/modifying agents comprise any modifying agent that can be linked to a binding agent and carry out modification to one or more bases in the vicinity of the binding site of the binding agent. Certain exemplary and nonlimiting modifying agents appropriate for inclusion in a binding/modifying agent include Dam methyltransferase (described above), Dcm cytosine methyltransferase, CpG cytosine methyltransferases (e.g., DNMT1, Sss1, etc.), C4-cytosine methyltransferases, hydroxylases (e.g., TET1 protein, which converts methylcytosine to hydroxymethylcytosine), glycosylases, nucleic acid damaging agents (e.g., nucleases), or combinations thereof. Additional enzymes that can function as modifying agents are provided in Lakshminarayan, et al. (2009) Cell Cycle 8(11):1698-1710, incorporated herein by reference in its entirety for all purposes.

In certain embodiments, a single modifying agent linked to a single binding agent can introduce multiple modifications into a nucleic acid to which the binding agent is bound, e.g., where multiple different recognition sequences for the modifying agent are present and within reach of the modifying agent. For example, a linker connecting the binding agent can be of a length and flexibility to facilitate multiple modifications at or around the binding site, e.g., both upstream and downstream of the binding site. Such multiple modification events at or around a binding site can facilitate more specific mapping of the exact binding site, e.g., by both increasing the likelihood that the modifying agent will find a sequence to be modified. For example, modifications made upstream and downstream of the binding site are indicative of a binding site located at an intermediate location on the template. However, such flexibility in modification location can also complicate the mapping of the binding site where only one or a few modifications in close proximity to one another are introduced. For example, if a modifying agent is tethered to the binding agent by a flexible linker that allows both upstream and downstream modifications, it may not be clear where the binding site is relative to a single modification. As such, in some embodiments a stiff linker can help to orient the modification site with the binding site.

In some embodiments, a combination of modifying agents are linked to a single binding agent such that multiple different types of modifications can be introduced at or near the binding site. Multiple different modifications will have a greater effect on the activity of the polymerase enzyme at the binding site during nascent strand synthesis than would a single modification, and would thereby enhance detection and mapping of the binding site by effectively increasing the "signal" in that region. In addition, given that certain modifying agents exhibit sequence specificity, and sequence context around a binding site sequence at one locus can vary from the sequence context around the same binding site sequence at a different locus, having multiple different kinds of modifying agents on a single binding agent increases the likelihood that a modification will be introduced at a given binding site sequence within an unknown sequence context by effectively broadening the sequence context within which a modification will occur (e.g., CpG dinucleotides occur more frequently in the genome than do GATC tetranucleotides). Flexible or stiff linkers, or a combination of different linker types, can be used to link the modifying agents to the binding agent.

Further, precise mapping of the binding site can also be advanced by recognition of one or more nucleosides that are not modified near a modified nucleoside. The presence of the modification is indicative of the presence of the modifying agent, and the absence of a modification to a base that could have been modified provides information about the conformation and placement of the binding/modifying agent on the nucleic acid molecule. As such, where a given region has two sites for modification and only one is modified, the lack of a modification at the other site can be indicative of its presence within the "footprint" of the binding agent or, alternatively, that it was outside of the reach of the binding/modifying agent. Yet further, multiple modifications, whether by a single or multiple modifying agents linked to a binding agent, can further distinguish between these two possibilities.

In certain embodiments, the association of multiple different binding agents on one or more nucleic acid templates are tested in a single reaction mixture. Each different binding agent is linked to a distinct modifying agent (or plurality thereof) such that a modification detected within the template is indicative of the presence of a particular binding/modifying agent. For example, the associations of two different binding agents having the same or unknown consensus binding sites can be differentiated based on the type of modification introduced. Alternatively or in addition, where information about the sequence of the binding site of the binding agent is known, sequence data from the modified region can also be used to identify the binding agent that associated with that region. For example, two different binding agents having two different consensus binding sites can be linked to the same type of modifying agent. The presence of the modification indicates that a binding/modifying agent was bound, and the sequence of the region identifies the particular binding agent. Multiple different binding/modifying agents can be tested simultaneously or sequentially within a given experiment, e.g., by being present together or by being added separately, e.g., via buffer exchange. Experiments in which different binding agents having the same or overlapping binding sites are present together also allow for the examination of competition and affinity for the binding sites.

Yet further, complex formation can also be monitored where two different modifying agents are linked to two different components of a complex of interest. The identification of two different modifications introduced into the nucleic acid at a given locus is indicative of complex formation at that locus. Both of the components can be binding agents that bind to the nucleic acid during complex formation, or a first may bind to the nucleic acid while the second binds to the first.

Although the methods are particularly useful for detection and mapping of transcription factor binding sites, use of these methods to map binding sites for other classes of binding agents is also contemplated. Further, combinations of different classes of binding agents can be simultaneously tested, e.g., on an arrayed format. Of particular interest is the mapping of binding sites for histones, replication protein A (RPA), single-stranded binding protein (SSB), RNA-binding proteins, microRNA-containing ribonucleoprotein complexes, anti-DNA antibodies, and agents that bind altered or damaged nucleotides that are not otherwise detectable by alterations in polymerase activity during single-molecule sequencing reactions, which maps not only the location of the binding agents on the nucleic acid molecule, but the modified or damaged nucleotides themselves. Finally, although it is preferred to remove the binding/modifying agent prior to sequencing, in certain embodiments the sequencing can be performed in the presence of the bound agents, e.g., where a polymerase is capable of displacing the bound agents during the reaction, or a researcher is desirous of only collecting sequence data upstream of the bound agents. In such cases, the additional modifications can serve to enhance a pause or other kinetic response otherwise detected when the polymerase encounters a bound agent not linked to a modifying agent.

Crosslinking-Facilitated Detection/Mapping of Binding Agents

In certain aspects, detection of bound agents is facilitated by crosslinking the bound agents to the nucleic acid to which they are bound. CLIP (crosslinking and immunoprecipitation) is one commonly used technique in which bound proteins are crosslinked to RNA in vivo in an effort to determine where on the RNA the protein has bound. Following crosslinking, the RNA is removed from the cells, fragmented, subjected to RNase digestion, immunoprecipitated, and SDS-PAGE purified to isolate RNA fragments bound by the proteins while removing unbound fragments. The bound proteins are subsequently removed from the fragments, e.g., by degradation. The resulting ~20-40 nucleotide RNA fragments are termed "sequence tags" and represent the regions of the original RNA that were bound by protein at the time of the crosslinking. The sequence tags (or "CLIP tags") are subjected to RT-PCR to generate cDNA "copies" of the RNA fragments. The cDNA copies are sequenced to identify specific regions in the RNA to which the proteins were bound, but even after sequencing the exact position of crosslinking cannot be determined. Rather, it is simply inferred that the protein was bound somewhere within the 20-40 nucleotides in the RNA that correspond to a given sequence tag.

The present invention provides a more precise method for determining the site of crosslinking between a nucleic acid and a bound agent, and therefore a more accurate means of determining exactly where the agent was bound to the nucleic acid. In certain embodiments, a nucleic acid of interest is prepared by standard CLIP methods through the removal of the bound agents. However, removal of the bound agent(s) results in modified nucleosides since remnants of the crosslinks remain on the nucleosides that were previously crosslinked to the binding agents. While these modified nucleotides are not detectable by conventional CLIP sequencing, the single-molecule real-time sequencing methods provided herein are sensitive to modified nucleotides, as described at length herein. Briefly, these modifications can be detected by observing polymerase activity during nascent strand synthesis using the modified nucleic acids as templates since changes in the kinetic signature (e.g., rate, error profile, etc.) of the polymerase are indicative of a modified base in the template. As such, this method provides not only the sequence of the nucleic acid fragment to which a binding agent was crosslinked, but also the exact position of the previously crosslinked nucleoside(s) within the fragment. One beneficial aspect of this method is that cDNA conversion is not necessary for RNA nucleic acids (as is it in the CLIP protocol) because the RNA is sequenced directly by an RNA-dependent polymerase (e.g., reverse transcriptase).

Various modifications of this method can be implemented. For example, it can be used to map binding sites on any kind of nucleic acid that can undergo crosslinking with a bound agent and subsequent sequencing, e.g., RNA, DNA, RNA-DNA hybrids, nucleic acids comprising additional modifications, etc. Further, the crosslinking need not occur in vivo, and can instead be carried out in vitro, e.g. to screen binding agents from a biological sample against an array of known nucleic acids, or to screen nucleic acids from a biological sample against an array of known binding agents. Further, RNase digestion is also unnecessary since the sequencing methods herein are capable of sequencing long nucleic acid fragments, and because the crosslinking sites can be determined specifically rather than being inferred. Yet further, standard CLIP uses gel purification to isolate fragments prior to protein removal, but this step is not necessary for single-molecule real-time sequencing since each fragment is individually sequenced. However, in certain embodiments enrichment of previously crosslinked fragments may be desired, e.g., by gel purification, column chromatography, and other methods known in the art. Additionally, in certain embodiments the bound agents are not removed prior to sequencing. As described elsewhere herein, agents bound to the template strand alter polymerase activity, and the sequence read information immediately prior to the alteration allow mapping of the bound agent on the template. However, in preferred embodiments it is beneficial to remove the bound agents, e.g., when their presence would permanently block the polymerase and sequence reads downstream of the binding site are desired. In yet further embodiments, the immunoprecipitation step can occur at a reaction site at which subsequent sequencing of a bound nucleic acid will occur. For example, a reaction site can comprise a bound antibody to immunoprecipitate a binding agent of interest, as well as a polymerase enzyme to sequence a bound nucleic acid molecule. In arrays of reaction sites, one could control which binding sites are sequenced at each reaction site on an array by controlling which antibody is localized at each. The bound agent can optionally be removed from the nucleic acid subsequent to binding of the polymerase to the nucleic acid, and before initiation of the sequencing reaction.

In certain aspects, crosslinking is facilitated by incorporating modified bases into a nucleic acid prior to exposure to a binding agent of interest. Photoactivatable ribonucleoside-enhanced crosslinking and immunoprecipitation (PAR-CLIP) is a technique in which cells are grown in the presence of a photoactivatable nucleoside (preferably thiol-modified 4-thiouridine (s4U), although other photoactivatable nucleosides can be used, e.g., 6-thioguanosine (s6G), 2-thiocytosine (s2C), and 4-thiothymidine (s4T)) and subsequently exposed to UV light to crosslink RNA comprising the photoactivatable nucleoside to RNA-binding proteins (RBPs) and/or microRNA-containing ribonucleoprotein complexes (miRNPs) that are interacting with it. After immunoprecipitation and RNase treatment to degrade the RNA template not bound by the RBPs and/or miRNPs, the remaining portion of the bound template is isolated, e.g., by radioactive labeling followed by SDS-PAGE. Once the template is isolated, the bound agent(s) can be removed and the template converted to cDNA with a reverse transcriptase. The resulting cDNA is subjected to sequencing and misincorporation events are used to identify and map the modified base. For example, the presence of a crosslinked s4U nucleoside in a cDNA template causes a G to be misincorporated into the complementary strand opposite the s4U nucleoside during sequencing. Scoring for T to C transition in the resulting sequence read data (as compared to the known wild-type polynucleotide sequence) enables mapping of the binding sites of RBPs and/or miRNPs within the RNA.

The present invention provides various improvements to the conventional PAR-CLIP technique using single-molecule sequencing to determine primary nucleic acid sequence at the same time as measuring polymerase kinetics to detect modified and/or crosslinked (or previously crosslinked) nucleobases. Similar to the conventional PAR-CLIP method described above, the photoactivatable nucleoside in a nucleic acid of interest is crosslinked to an agent bound to the nucleic acid. This crosslinking can be performed in vitro, or it can optionally be performed in vitro, in which case the crosslinked nucleic acids would need to be removed from the cells by methods known to those skilled in the art. Unlike conventional PAR-CLIP, the present invention provides a method for directly sequencing a crosslinked RNA without converting it to cDNA, e.g., by carrying out a single-molecule real-time sequencing reaction with a reverse transcriptase or other RNA-dependent polymerase. The polymerase kinetics will be altered by the presence of the crosslink and/or the bound agent, facilitating detection of the same. For example, the location of s4U can be mapped directly by detection of G misincorporations into the nascent strand, detection of altered error rates compared to uridine (e.g., a high rate of cognate or non-cognate sampling), and detection of altered kinetics (pulse width and interpulse duration) compared to uridine.

Along with no requirement for cDNA conversion, there are additional benefits to the direct sequencing methods provided here. For example, it can be used to map binding sites on any kind of nucleic acid that comprises a modified base that undergoes crosslinking with a bound agent and can undergo subsequent sequencing, e.g., RNA, DNA, RNA-DNA hybrids, nucleic acids comprising additional modifications, etc. Further, there is no need for RNase (or other nuclease) treatment because the methods herein can distinguish between the modified bases that are crosslinked and those that are not crosslinked. In fact, it is preferable to sequence a long template because a long sequencing read is generally easier to align and map to a known sequence, e.g., from a genomic sequence database. However, if it is desired to reduce the size of the template or to remove non-crosslinked modified nucleosides, RNase treatment can optionally be performed. There is also no requirement that the crosslinked nucleic acids be radioactively labeled and gel purified. Rather, a preparation of crosslinked and non-crosslinked nucleic acids can be applied to an array of optically resolvable polymerase enzymes, and sequencing can be carried out on single molecules of nucleic acid at each polymerase. Both the sequence reads and enzyme kinetics on each of the single molecules is used to identify which have modified nucleosides, and which of those are or were crosslinked to bound agents. Nevertheless, if it is desired to reduce the complexity of the nucleic acid sample, or to only subject crosslinked nucleic acids to sequencing, one can isolate those molecules by SDS-PAGE or other methods known in the art. Finally, in certain embodiments the bound agents are not removed prior to sequencing. As described elsewhere herein, agents bound to the template strand alter polymerase activity, and the sequence read information immediately prior to the alteration allow mapping of the bound agent on the template. However, in other embodiments it is beneficial to remove the bound agents, e.g., if their presence would permanently block the polymerase and sequence reads downstream of the binding site are desired. In this way, single-molecule real-time sequencing can be used for directly mapping binding sites to RNA without the additional step of cDNA conversion. In addition, simply converting a natural base to a modified base can facilitate sequencing of the template by altering the behavior of the polymerase at the modified base, as described elsewhere herein. This is of particular importance where a long template having a plurality of modified bases, only some of which are crosslinked to bound agents, is to be sequenced. In such embodiments, both the non-crosslinked and crosslinked modified bases are distinguishable from one another and also from the non-modified bases of the template. In yet further embodiments, the immunoprecipitation step can occur at a reaction site at which subsequent sequencing of a bound nucleic acid will occur. For example, a reaction site can comprise a bound antibody to immunoprecipitate a binding agent of interest, as well as a polymerase enzyme to sequence a bound nucleic acid molecule. In arrays of reaction sites, one could control which binding sites are sequenced at each reaction site on an array by controlling which antibody is localized at each. The bound agent can optionally be removed from the nucleic acid subsequent to binding of the polymerase to the nucleic acid, and before initiation of the sequencing reaction. For more information on the use of CLIP and PAR-CLIP in transcriptome studies, see Hafner, et. al. (2010) Cell 141: 129-141; Wang, et al. (2009) Methods 48(3):287-93; Ule, et al. (2003) Science 302:1212-1215; and Ule, et al. (2005) Methods 37(4):376-86, which are incorporated herein by reference in their entireties for all purposes.

When implemented on in an arrayed format, such investigations would be highly parallel, enabling high-throughput screening assays. Arrays of reactions are carried out on highly multiplexed confocal fluorescence microscope systems (see, e.g., Lundquist, et al., incorporated herein above) in which the instrument detects fluorescent signals from each reaction site on the array, resulting in a highly parallel operation. Although preferred embodiments use arrays of zero mode waveguides, as described elsewhere herein, these assays could also be performed in other systems capable of real-time single-molecule detection, e.g., using total internal reflection fluorescence (TIRF) microscopy or waveguide technology.

Although certain embodiments are described in terms of nucleic acid binding proteins, it will be appreciated that the methods and systems described herein are equally applicable to other nucleic acid binding agents capable of pausing, stopping, or otherwise disrupting processive template-directed synthesis of a nascent nucleic acid molecule, e.g., nucleic acids and analogs and mimetics thereof (e.g., protein nucleic acids), lipids, sugar-oligoamides, intercalating dyes, major and minor groove binders, etc.

VIII. Nucleic Acid Binding Agents as Analytical Tools

In certain aspects, nucleic acid binding agents are used in the methods, compositions, and systems of the invention to detect and/or reverse modifications in nucleic acid molecules. Such agents are typically used to enhance the response of a polymerase to a modification in the template nucleic acid. That is, the methods herein can be used to detect binding of an agent to the template, whether in response to a modification as described below, or simply an unmodified recognition site within the sequence of the template, as described above. Further, the effects of various agents on the creation, detection, or bypass of a nucleotide modification can also be tested and compared. For example, a template can be treated in various different ways (e.g., with and without a nucleic acid binding agent) and subsequently subjected to single-molecule sequencing-by-synthesis, which is monitored for a disruption in sequence read generation that is characteristic of binding of the agent to the template. In other embodiments, a template containing a known modification can be subjected to single-molecule sequencing-by-synthesis in the presence of various agents and/or reaction conditions. The reaction is monitored for the activity of the polymerase on the modified template to determine if the presence of any of the agents or other conditions impacts the ability of the polymerase to bypass or pause at the modification.

In certain specific embodiments, accentuating the differences in interpulse duration and/or pulse width between methylated and unmethylated DNA involves DNA binding proteins. It has been shown that some DNA polymerases stall when they encounter a DNA-bound protein complex. (See, e.g., M. Elias-Arnanz, et al., *EMBO J.* 1997, 16, 5775, incorporated herein by reference in its entirety for all purposes.) In SMRT™ sequencing, this stall is detected as an unusually long interpulse duration that would end when the binding protein dissociates from the DNA template or is displaced by the translocating polymerase. There are a number of proteins that can bind stably and specifically to methylated DNA including members of the MBD family of human proteins, all of which contain a methyl-CpG binding domain (MBD). For example, MECP2, MBD1, MBD2, and MBD4 all bind specifically to methylated DNA, and are involved in repressing transcription from methylated gene promoters. Binding of these proteins to a template nucleic acid is expected to cause a translocating polymerase to pause proximal to the bound protein. As such, an increased pause duration during single-molecule sequencing reactions is indicative of a methylated base in the template nucleic acid. It is therefore important that the protein bind tightly to its target nucleic acid sequence. Natural MBD proteins only have micromolar Kd affinities for methyl-CpG sequences, so engineered MBD proteins that bind more tightly to the methylated template sequence can enhance detectability of methylated bases. For example, a multimerized MBD1 protein is provided in Jorgensen, et al., *Nucleic Acids Research* 2006, 34(13), e96. Such engineered proteins can have a single methyl binding domain with a lower Kd (sub-micromolar) or multiple methyl-binding domains that increase the effective concentration of the methyl-binding domain in the vicinity of the methylated DNA template. More information on the MBD family of proteins is provided, e.g., in B. Hendrich, et al., *Mol Cell Biol* 1998, 18(11), 6538; and I. Ohki, et al., *EMBO J* 2000, 18(23), 6653.

In addition, the mammalian UHRF1 (ubiquitin-like, containing PHD and RING finger domains 1) protein binds tightly to methylated DNA and is required for its maintenance. Crystal structures of the SRA domain of this protein bound to DNA show that the 5-MeC is flipped out of the DNA duplex and stabilized by hydrophobic stacking and hydrogen bonding to SRA protein residues. (See, e.g., G. V. Avvakumov, et al. and H. Hashimoto, et al., both supra.) Further, McrBC is an endonuclease that cleaves DNA containing 5-methylcytosine or 5-hydroxymethylcytosine or N4-methylcytosine on one or both strands, but does not act upon unmethylated DNA. McrBC requires GTP for cleavage, but in the presence of a non-hydrolyzable analog of GTP, the enzyme will bind to methylated DNA specifically, without cleavage. (See, e.g., Irizarry, R. A. et al. (2008) *Genome Res.*, 18, 780-790; and Hublarova, P. et al. (2009) *Int J Gynecol Cancer*, 19, 321-325, the disclosures of which are incorporated herein by reference in their entireties for all purposes.) Finally, the monoclonal antibody to 5-MeC, used for methylated DNA immunoprecipitation, also binds specifically to methylated cytosine. (See, e.g., N. Rougier, et al., *Genes Dev* 1998, 12, 2108; and M. Weber, et al., supra, which are incorporated herein by reference in their entireties for all purposes.) All of the above-mentioned proteins are candidates for interfering with normal. DNA polymerase processivity during SMRT™ sequencing. In order to enhance, decrease, or otherwise modify their polymerase stalling effects, any of these proteins can be engineered to alter their affinity for methylated DNA sites, e.g., by introducing mutations into their active sites or other domains involved in binding. See, e.g., H. F. Jorgensen, et al., *Nucleic Acids Res* 2006, 34, e96, the disclosure of which is incorporated by reference herein in its entirety for all purposes. For example, in order to ensure the protein can cause a pause prior to displacement, a weakly binding protein can be altered to increase the binding strength. Likewise, in order to allow eventual displacement of the protein by the polymerase, a protein with a high binding strength can be altered to weaken the binding strength.

In yet further embodiments, an antibody against 5-MeC could be used to bind 5-MeC in a template nucleic acid, similar to the process used in methylated DNA immunoprecipitation assays (M. Weber, et al., *Nat Genet* 2005, 37, 853). As such, the antibody essentially acts as an enhancer of the signal indicating the presence of the modification in the template by virtue of altering the polymerase dynamics. Various components of such reactions can be detectably labeled, e.g., the antibody, template, incorporated nucleotides, and combinations thereof, as described further elsewhere herein.

In still further embodiments, methyltransferases can be used to further facilitate detection of methyl-modified template nucleic acids. As described above, DNA methyltransferases catalyze the addition of methyl groups to DNA based upon recognition of methylation sites. For some methyltransferases (e.g., maintenance methyltransferases), the most active binding site in a nucleic acid is a hemi-methylated site in which one strand of the nucleic acid is methylated and the opposite strand is not. An enzymatically inactive methyl transferase (i.e., one that is unable to methylate nucleic acids) will therefore preferably bind to a hemi-methylated strand of DNA. In a real-time, template-directed sequencing reaction, a methylated single-stranded template becomes hemimethylated after nascent strand synthesis. A detectably labeled methyltransferase can therefore be detected interacting with the hemimethylated product of the synthesis reaction in real-time.

In certain embodiments, a circular template is used to permit rolling-circle synthesis by the polymerase in which a single-stranded circular template is converted to a double-stranded circular template. In preferred embodiments, the polymerase is capable of strand displacement such that after proceeding around the template once it begins to displace the nascent strand ahead of it as synthesis continues. This process eventually results in long concatemer containing multiple copies of the complement to the original template molecule. In such a system, a single-stranded methylated template is converted to a double-stranded hemimethylated template. A methyltransferase present in the reaction mixture can bind the hemimethylated sites and, if detectably labeled, this binding can be readily monitored in real time. When the polymerase encounters a bound methyltransferase, a pause may be detected prior to dissociation of the methyltransferase. The location of the pause in the resulting sequence reads can be used to map the position of the methylated site within the template molecule, even in the absence of a detectable label on the methyltransferase. For example, the pause can be used to identify the binding of the methyltransferase, e.g., in cases in which the methyltransferase is not detectably labeled, and in such cases the methyltransferase would essentially serve to extend the pause at a methylated site, thereby facilitating identification of such a site in the template nucleic acid.

Other types of modifications can also be detected and/or reversed by nucleic acid binding agents. For example, among all types of DNA damage, oxidative base damage by reactive oxygen species (ROS) has been recognized as a major cause of cell death and mutagenesis in aerobic organisms (see, e.g., Finkel, et al. (2000) Nature 408(6809): 239-47, which is incorporated herein by reference in its entirety for all purposes). DNA oxidative lesions (e.g., abasic sites) are primarily recognized and repaired by base excision repair (BER) pathways (see, e.g., Fromme et al. (2004) Adv Protein Chem 69: 1-41, which is incorporated herein by reference in its entirety for all purposes). In humans, the BER pathway for detecting and repairing a common oxidative lesion, 7,8-dihydro-8-oxoguanine ("8-oxoG"), begins with recognition of the lesion by a human oxoguanine DNA glycosylase 1 (hOgg1), which is a DNA glycosylase/apurinic (AP) lyase (see, e.g., Klungland, et al. (2007) DNA Repair (Amst) 6(4): 481-8, which is incorporated herein by reference in its entirety for all purposes).

The modified base 8-oxoG is discussed at length supra. Recent fluorescence and crystallography studies of hOgg1 found that this DNA glycosylase recognizes the oxidative DNA lesion 8-oxoG by scanning the DNA duplex, flipping the DNA base out, and transferring the damaged base from a pre-sampling binding site to the damage recognition binding site. Single-molecule experiments revealed the rapid sliding activity of hOgg1 on DNA duplex. For more detailed information on these studies, see Banerjee, et al. (2005) Nature 434(7033): 612-8, and Blainey, et al. (2006) Proc Natl Acad Sci USA 103(15): 5752-7, the disclosures of which are incorporated herein by reference in their entireties for all purposes.

In certain embodiments, the methods provided by the invention expose a nucleic acid template to a damage-recognition agent that binds to the template at a damaged nucleotide in a manner that blocks bypass of the lesion by a polymerase translocating along the template. The blockage causes a cessation of incorporation-dependent signaling from the reaction site, thereby indicating the damage-recognition agent has bound a damaged nucleotide in the template. In some aspects, the methods further include exposing a damaged template to additional reaction components that act to repair the damage, restoring the template and allowing dissociation of the damage-recognition agent from the previously damaged nucleotide. Elements of the damage-repair (e.g., base excision repair (BER)) machinery can be provided in the original reaction mixture, or can be added to an ongoing reaction. If the polymerase pauses but does not dissociate, the polymerization reaction can continue after DNA repair has been completed and the repair machinery has dissociated from the template or translocated away from the previously-damaged site.

In preferred embodiments, the damage-recognition agent is a protein involved in BER such as DNA gycosylases/apurinic (AP) lyases, e.g., hOGG1 (human oxoguanine DNA glycosylase 1), yOGG1 (yeast homolog of hOGG1), FPG protein (MutM; bacterial homolog of hOGG1); and others known in the art. Other proteins that can be used as a damage-recognition agent include other DNA glycosylases, e.g., AlkA, Nth, Nei, MutY, uracil DNA glycosylases (UDG), single-strand selective monofunctional uracil-DNA glycosylase (SMUG), thymine DNA glycosylase (TDG), NEIL (e.g., hNEIL1 and hNEIL2), etc. Reaction components for repair of a damaged template bound by the damage-recognition agent include, e.g., AP endonucleases, DNA polymerase beta, and ligase, among others known in the art. See, e.g., McCullough, et al. (1999) Annu Rev Biochem 68: 255-85, which is incorporated herein by reference in its entirety for all purposes. Further, additional proteins that stimulate damage recognition may also be included in an analytical reaction; e.g., HAP1 (APE1) protein has been found to stimulate hOGG1 activity (Vidal, et al. (2001) Nuc. Ac. Res. 29(6):1285-1292).

In certain embodiments, more than one polymerase may be present in a template-directed sequencing reaction in which one or more lesions may be present on the template nucleic acid. For example, "bypass polymerases" have been discovered in both prokaryotes and eukaryotes, most of which belong to the Y-family of polymerases and/or are considered to be repair polymerases. In contrast to replicative polymerases, they operate at low speed, low fidelity, and low processivity. However, because their active sites adopt a more open configuration than replicative polymerases they are less stringent and can accommodate altered bases in their active sites. For more information on bypass polymerases, see, e.g., Cordonnier, et al. (1999) Mol Cell Biol 19(3):2206-11; Friedberg, et al. (2005) Nat Rev Mol Cell Biol 6(12):943-53; Holmquist, et al. (2002) Mutat Res 510(1-2):1-7; Lehmann, A. R. (2002) Mutat Res 509(1-2):23-34; Lehmann, A. R. (2006) Exp Cell Res 312(14):2673-6; Masutani, et al. (1999) Nature 399(6737):700-4; and Ohmori, et al. (2001) Mol Cell 8(1):7-8, the disclosures of which are incorporated herein by reference in their entireties for all purposes. Certain of these polymerases can bypass lesions in a nucleic acid template and carry out "translesion synthesis" or TLS. As such, DNA replication in the presence of such lesions was found to require multiple polymerases and the "polymerase switch model" was developed (see, e.g., Friedberg, et al. (2005) Nat Rev Mol Cell Biol 6(12):943-53; Kannouche, et al. (2004) Cell Cycle 3(8):1011-3; Kannouche, et al. (2004) Mol Cell 14(4):491-500; and Lehmann, et al. (2007) DNA Repair (Amst) 6(7): 891-9, all of which are incorporated herein by reference in their entireties for all purposes). In brief, the polymerase switch model is model for lesion bypass during replication that involves replacement of a replicative polymerase with a bypass polymerase at a lesion, synthesis of the nascent strand by the bypass polymerase until past the lesion, and subsequent replacement of the bypass polymerase with the more processive, higher fidelity replicative polymerase for continued replication past the lesion.

In certain preferred embodiments, one or more bypass polymerases are included in a template-directed nucleic acid sequencing reaction. For example, during the course of a reaction in which a replicative polymerase encounters and is blocked by a lesion in a template nucleic acid, the replicative polymerase is replaced by a bypass polymerase at the site of the lesion, and the bypass polymerase synthesizes a segment of the nascent strand that is capable of base-pairing with the damaged base, and may further include one or more bases prior to and/or past the site of the lesion in a process called "translesion synthesis." The limited processivity of the bypass polymerase causes it to dissociate and be replaced by the replicative polymerase following translesion synthesis. The replicative polymerase continues to synthesize the nascent strand until another blocking lesion is encountered in the template, at which point it is once again replaced by a bypass polymerase for translesion synthesis. (See, e.g., Friedberg, et al. (2005) Nat Rev Mol Cell Biol 6(12):943-53; and Kannouche, et al. (2004) Mol Cell 14(4):491-500, incorporated herein by reference above.) The process continues until the template has been replicated or the reaction is tea Initiated, e.g., by the investigatior. One particular advantage of the polymerase switch method of template-dependent sequencing is that is it tolerant of most types of lesions in the template nucleic acid. As such the damaged template can be sequenced through a lesion, thereby allowing reinitiation of synthesis downstream of the lesion and increasing read lengths on lesion-containing templates.

Various different bypass polymerases known to those of ordinary skill in the art can be used with the methods and compositions provided herein, include prokaryotic polymerases (e.g., DNA polymerase IV, polymerase V, Dpo4, Dbh, and UmuC) and eukaryotic polymerases (e.g., DNA polymerase η, DNA polymerase ι, DNA polymerase κ, and Rev1). In eukaryotes, multiple bypass polymerases participate in translesion synthesis, and a processivity factor, proliferating cell nuclear antigen ("PCNA"), is also required and can be included in a sequencing reaction.

In certain preferred embodiments, the template or primer is immobilized during the template-dependent synthesis reaction to ensure that the template remains at the reaction site during polymerase switching. Alternatively or additionally, one or more polymerases can be immobilized at the reaction site. Various immobilization strategies useful in different aspects of the invention are provided elsewhere herein.

Since the portion of the nascent strand corresponding to the site of the lesion in the template is synthesized by a bypass polymerase, the sequence reads generated therefrom are expected to be less reliable than those generated from regions of the nascent strand synthesized by the replicative polymerase. As such, generation of redundant sequence information during a sequencing reaction is a preferred means of generating complete and accurate sequence reads. Redundancy can be achieved in various ways described elsewhere herein, including carrying out multiple sequencing reactions using the same original template with the sequence data generated in the multiple reactions combined and subjected to statistical analysis to determine a consensus sequence for the template. For example, the sequence data from a region in a first copy of the template that was replicated by a lower fidelity bypass polymerase can be supplemented and/or corrected with sequence data from the same region in a second copy of the template that was replicated with a higher fidelity replicative polymerase. Further, a template can be amplified (e.g., via rolling circle amplification) to generate a concatemer comprising multiple copies of the template that is subsequently sequenced to generate, a sequencing read that is internally redundant. The sequence data from a first segment of the concatemer (corresponding to a first region of the template) that was replicated by the bypass polymerase can be supplemented and/or corrected with sequence data from a second segment of the concatemer (that also corresponds to the first region of the template) that was replicated by the replicative polymerase. Further, as noted above, redundancy can also benefit identification and characterization of lesions that occur in the same position in a plurality of templates, or that occur at a single position in a template that is subjected to resequencing. For example, since base incorporation by the bypass polymerase is promiscuous, replicate sequencing reads for the region containing the lesion may show more than one "complementary base" being incorporated at the same position in different reads (of the same or an identical template), and detection of such promiscuity is indicative that there is a lesion at that position in the template nucleic acid(s).

In certain embodiments, a polymerase in the reaction mixture may comprise a detectable label to indicate when that polymerase is associated with the template nucleic acid. For example, a bypass polymerase can comprise a detectable label that will indicate when the bypass polymerase is carrying out translesion synthesis. The nucleotides incorporated into the nascent strand during that time can therefore be identified and "tagged" as corresponding to a region of the template that contains one or more lesions, thereby allowing targeting of statistical analysis to these sequence reads, e.g., as described above.

In yet further embodiments, a nucleic acid binding agent specifically binds to secondary structure in the nucleic acid template, e.g., hairpin loops, stem-loops, internal loops, bulges, pseudoknots, base-triples, supercoiling, internal hybridization, and the like. Binding of an agent to such structures inhibits passage of the polymerase through the structures to a greater extent than the enzyme is inhibited in the absence of the agent, thereby increasing the resulting pause time and facilitating detection of the secondary structure. Examples of agents that have binding specificity for specific structures and/or strandedness in nucleic acids include, e.g., intercalating agents, nuclease-deficient endonucleases (e.g., with a specificity for a double-stranded region within a stem-loop structure), polymerases, and various eukaryotic initiator proteins.

Figure 6:
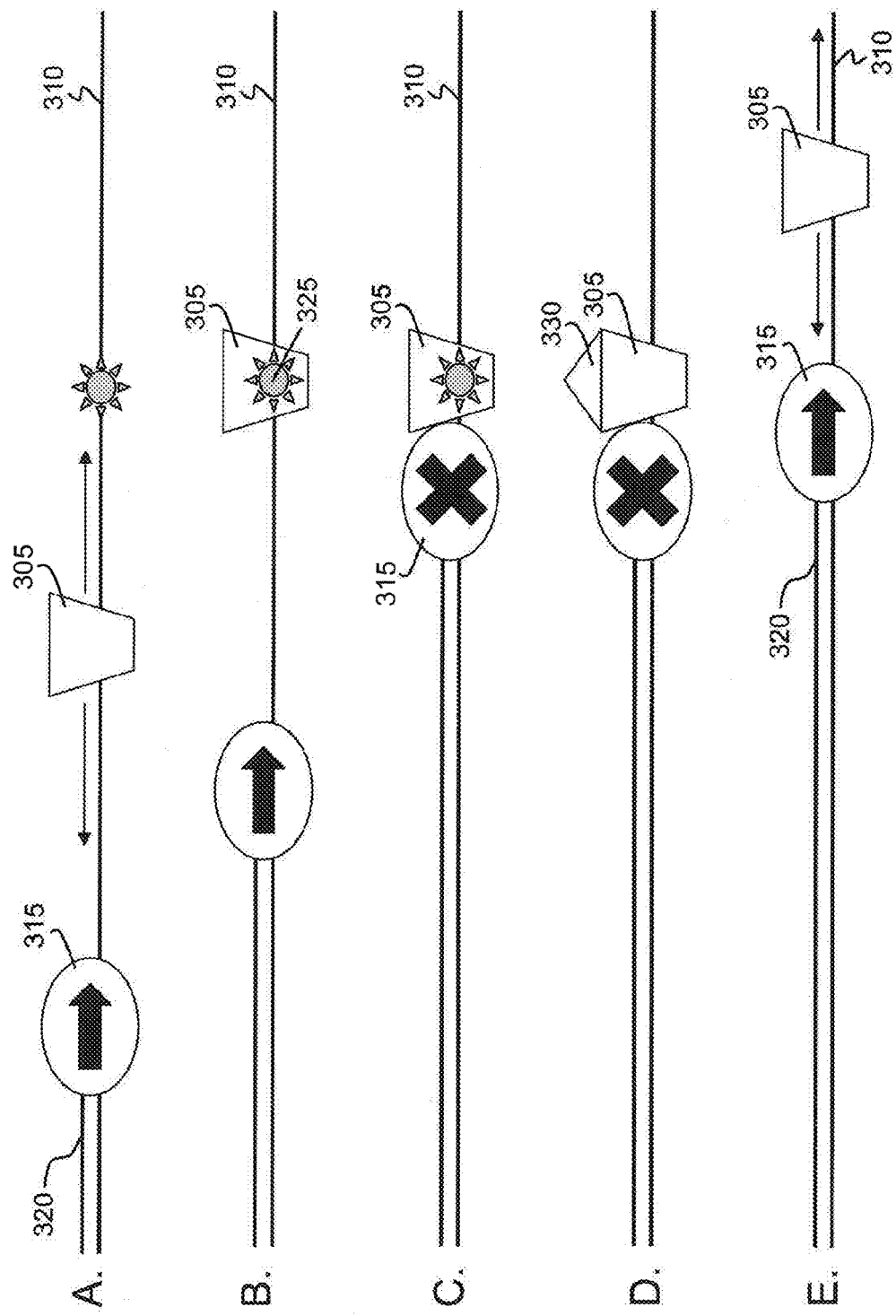
FIGS. 6A-6E provide a illustrative embodiment of a reaction comprising a linear template and a damage-binding agent that recognizes a lesion in a single-stranded template.

As noted above, various different types of templates for template-directed polymerization reactions can be used, e.g., single-stranded or double-stranded DNA, single-stranded or double-stranded RNA, DNA/RNA hybrids, and analogs, hybrids, derivatives, and mimetics thereof. Further, the template can contain a combination of single-stranded and double-stranded regions, e.g., such as the templates described in U.S. Ser. No. 12/383,855 and 12/413,258, both filed on Mar. 27, 2009 and incorporated herein by reference in their entireties for all purposes. The type of template used is limited only by the substrate specificity of the polymerase and damage-binding agent in the reaction. For example, FIG. 6 provides an illustrative embodiment of such a reaction comprising a linear template and a damage-binding agent that recognizes a lesion in a single-stranded template. In A, the damage-binding agent (305) is scanning a linear, single-stranded nucleic acid template (310) ahead of a polymerase (315) performing template-directed polymerization of a nascent nucleic acid strand (320). In B, the damage-binding agent (305) has detected and bound to a lesion (325) in the single-stranded template (310). In C, the polymerase (315) has caught up with the damage-binding agent (305) and its progress along the template (310) is blocked. In D, the lesion has been repaired by repair machinery (330) recruited by the damage-binding agent (305). In E, the repair machinery has dissociated from the template (310) and the damage-binding agent (305) has translocated away from the previously damaged site, thereby allowing the polymerase (315) to resume synthesis of the nascent strand (320).

Figure 7:
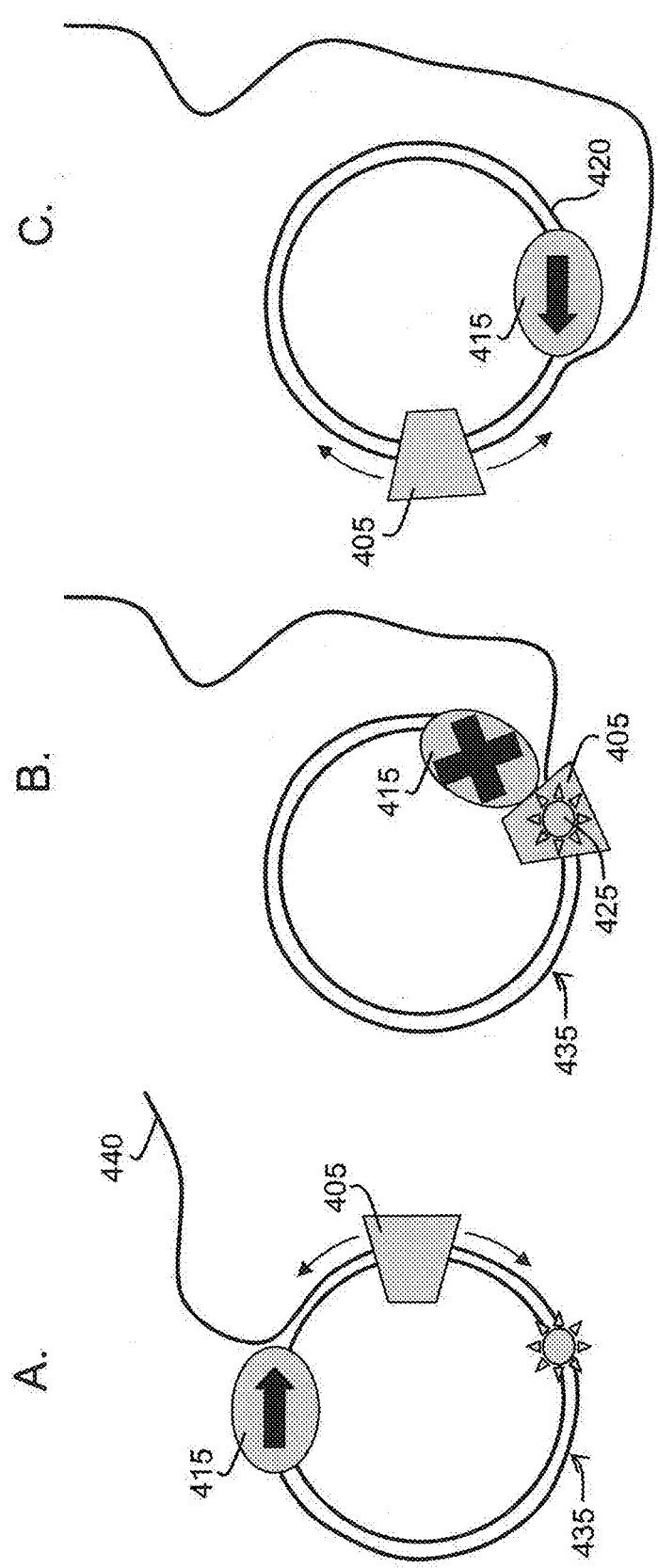
FIGS. 7A-7C illustrate an embodiment of the invention comprising a circular template and a damage-binding agent that recognizes a lesion in a double-stranded template.

In some embodiments, a damage-binding agent with specificity for double-stranded nucleic acid may be used in a reaction comprising a single-stranded template, e.g., when the scanning and damage detection/binding is expected to occur after the polymerase has converted the single-stranded template to a double-stranded template by template-dependent polymerization, e.g., after a single-stranded circle has been converted to a double-stranded circle during "rolling-circle replication." For example, although an initial substrate in a reaction is a circular single-stranded nucleic acid template, after a polymerase has processed the template one time it becomes a double-stranded template and an appropriate substrate for a damage-binding agent that specifically scans and binds double-stranded nucleic acid. For example, FIG. 7 illustrates an embodiment comprising a circular template and a damage-binding agent that recognizes a lesion in a double-stranded template. In A, the damage-binding agent (405) is scanning a circular, double-stranded nucleic acid template (435) ahead of a polymerase (415) performing template-directed polymerization while displacing the 5' end of the nascent nucleic acid strand being synthesized (440). In B, the damage-binding agent (405) has detected and bound to a lesion (425) in the double-stranded template (435), and the progress of the polymerase (415) is blocked by the bound damage-binding agent (405). In C, the lesion has been repaired and the damage-binding agent (405) has translocated away from the previously damaged site, thereby allowing the polymerase (415) to resume synthesis of the nascent strand (420).

Although various embodiments are described in terms of recognition and, optionally repair of 8-oxoG lesions, other types of DNA damage can also be addressed by the methods herein. For example, in the case of hOGG1, the N-glycosylase activity releases damaged purines from double-stranded DNA, generating an apurinic (AP) site. The AP-lyase activity cleaves 3' to the AP site leaving a 5' phosphate and a 3'-phospho-$\alpha$, $\beta$-unsaturated aldehyde. In addition to 8-oxoG (when paired with cytosine), hOGG1 also recognizes and removes 8-oxoA (when base paired with cytosine), foramidopyrimidine (fapy)-guanine and methyl-fapy-guanine (Bjoras, M. et al. (1997) *EMBO J.,* 16, 6314-6322; and Boiteux, S, and Radicella, J. (1999) *Biochimie,* 81, 59-67, the disclosures of which are incorporated herein by reference in their entireties for all purposes). Other types of DNA damage that can be bound and, optionally, repaired by the methods herein include BER enzymes that repair other DNA base lesions (small DNA base modifications, abasic sites, etc.), e.g. AAG/MPG for methylated lesions, UDG/SUMG1 for repairing uracil in DNA, apurinic endonuclease (APE) for abasic sites, etc. Also included are nucleotide excision repair (NER) enzymes that repair more bulky DNA lesions, such as DNA base adducts and DNA intra- and inter-strand crosslinks. Furthermore, although the DNA polymerase switch methods described above are suitable for detecting and bypassing most DNA lesions that block a replicative polymerase, certain small base modifications like 8-oxoG can be bypassed by a replicative polymerase, and thus methods that include binding agents that block the polymerase at the site of a lesion can help ensure that such lesions are detected, and optionally removed, from the template to prevent the sequence data generated from the template-dependent sequencing reactions to be adversely affected.

In certain embodiments, hOGG1 is included in a template-directed DNA sequencing reaction in the presence of a polymerase and a set of nucleotides, each of which bears a label that is optically detectable and that distinctively identifies the base (e.g., A, G, T, or C). Detection of an optical signal upon interaction with the polymerase and incorporation into the nascent strand allows the practitioner to identify the base incorporated and, by complementarity, the sequence of the template DNA molecule. In preferred embodiments, the incorporation of nucleotides into the nascent strand continues in a processive fashion, generating an ordered set of optical signals that can be analyzed to provide a sequence for both the nascent strand and, by complementarity, the template strand. The hOGG1 enzyme associates with the template, "scans" for damage, and specifically binds to locations at which such damage occurs. As such, if the template DNA molecule contains or acquires (e.g. during the course of the analytical reaction) DNA damage recognized by hOGG1, it is bound by hOGG1, bypass of the lesion by the polymerase is blocked, and the incorporation-based signal is slowed or stopped (e.g., by stalling or dissociation of the polymerase). Although such a blockage can cause dissociation of the polymerase, in certain preferred embodiments the polymerase merely pauses until the damaged nucleotide is repaired and hOGG1 and any other repair machinery dissociates from the template, at which time polymerization resumes and additional sequence data is generated from the template at and downstream of the site of the previously damaged nucleotide.

In certain preferred embodiments, one or more reaction components is immobilized at a reaction site, e.g., in an optical confinement such as a zero mode waveguide (ZMW). In some embodiments, the polymerase is immobilized and the nucleic acid template and damage-binding agent are free in solution. Methods for immobilizing a polymerase enzyme are available in the art and provided elsewhere herein. In other embodiments, the nucleic acid template can be immobilized at the reaction site with the polymerase and damage-binding agent free in solution. For example, in preferred embodiments the damage-binding agent translocates upon the template faster than the polymerase so it does not impede progress of the template-dependent sequencing reaction on an undamaged template. However, upon binding a lesion, the damage-binding agent will stop and bind to the site, blocking progress of a translocating polymerase past the lesion. For example, hOGG1 translocates much faster than phi29 polymerase on undamaged DNA, but after encountering a damaged nucleotide the enzyme will bind to the site and wait for other components of the BER, machinery. Alternatively or additionally, the damage-binding agent may be immobilized at the reaction site. For example, in the case of hOGG1 only a single enzyme is required for DNA binding, scanning, and lesion recognition. Immobilization of a single damage-binding agent at the reaction site increases the likelihood that a single template at each reaction site will be scanned for damage. Methods for immobilizing various reaction components are known in the art as described elsewhere herein.

In certain aspects, the methods for detection of nucleic acid damage can be used to test various elements of an experimental system to identify sources of such damage. For example, various buffer conditions or other components of an analytical reaction (e.g., reaction components or radiation that can induce production of oxygen radicals) can be tested to identify those that cause the least amount of damage for use in an experimental system. Further, such damage can be intentionally introduced into a nucleic acid template by the practitioner, e.g., at one or more specific locations in a template. This provides a means for controlling the progress of the polymerase, and therefore controlling the timing of production of sequence reads from different portions of the template. For example, if the template is extremely long (e.g., thousands or tens of thousands of base pairs in length), it may be beneficial to temporarily pause the reaction at one or more points on the template to allow orientation of the sequence read to the template. In particular, a pause in emission of signal pulses is indicative that the polymerase has reached a particular location on the template, and the investigator can reinitiate polymerization by addition of repair agents/proteins to the reaction mixture. Such repair agents may be washed out of the reaction mixture and, optionally, reintroduced at a later point during the course of the reaction, e.g., by buffer exchange.

In certain aspects, the use of binding agents specific for modifications of interest can facilitate enrichment of a nucleic acid preparation of those modifications. As described at length herein, a plethora of agents can specifically bind a variety of modifications within a nucleic acid molecule. While described elsewhere as having a direct impact on a single molecule sequencing reaction, these agents can also be used as a "tag" for isolating nucleic acids having modifications from a mixture of nucleic acids. In some embodiments, an antibody specific for a modification of interest is introduced to a nucleic acid sample suspected of having the modification under conditions that promote binding of the antibody to the modification. The antibody is typically linked to a solid support, e.g., a bead or column, such that nucleic acids that are not bound can be removed, e.g., by washing or buffer exchange. Subsequently, the nucleic acids bound to the antibody are released and subjected to sequencing with most or all of the nucleic acids sequenced having the modification of interest. In other embodiments, proteins that specifically recognize and bind to a modification of interest are used to target and enrich the modification in a nucleic acid mixture. For example, J-binding protein 1 (JBP1) binds specifically to base J-containing duplex DNA (see, e.g., Cross, et al. (1999) EMBO J. 18:6573-6571; and Borst, et al. (2008) Annu. Rev. Microbiol. 62:235-251.) JBP1 can be immobilized to allow base J-containing nucleic acids to be captured while nucleic acids lacking base J are not bound and can be removed. In yet further embodiments, a modification-comprising nucleic acid may be further modified to facilitate capture. For example, T4 phage β-glucosyl-transferases can add a glucose moiety to 5-hydroxymethylcytosine within a nucleic acid template, and binding agents (e.g., antibodies) specific to the resulting glucosyl-5-hydroxymethylcytosine can be used to enrich for nucleic acids comprising this modified base. It will be clear to one of ordinary skill that other binding agents, e.g., those described herein, can also be used for such enrichment procedures, to the extent that they can either be immobilized themselves, or be bound by an immobilized binding agent, e.g. an antibody other binding partner. Further, where multiple different modifications are to be sequenced, multiple enrichments can be performed, e.g., within a single reaction mixture where all modifications are collected together, or in separate aliquots of the original nucleic acid sample where each modification is separately enriched.

Enrichment strategies are beneficial, both for reducing experimental variation and increasing efficiency of identifying modifications within a nucleic acid sample. For example, in certain preferred embodiments a nucleic acid sample is exposed to a binding agent that specifically binds a modification of interest, the nucleic acid sample is fragmented, and fragments comprising the modification are retained by virtue of their association with the binding agent. In doing so, the resulting nucleic acid sample is less complex and more enriched for fragments of interest than was the original nucleic acid sample. This "enriched sample" is divided into two aliquots, only one of which is subjected to an amplification reaction that does not maintain the modifications in the resulting amplicons. These amplicons represent the regions of the original nucleic acid sample that comprised the modifications, but since the modifications are no longer present they serve as the reference sequence to which the sequence of the unamplified fragments in the enriched sample (i.e., which still comprise the modifications) will be compared. The fragments in both the amplified unamplified aliquots are sequenced and statistically analyzed to determine positions at which they differ, which are indicative of modifications in the original template. Although the complexity reduction step is preferred, it is not required. For example, the original nucleic acid sample can also be divided and only a portion amplified to remove the modifications and provide a "reference" sample. In certain embodiments, the amplified and unamplified fragments (whether enriched or not) are capped with hairpins or stem-loop structures to create closed, circular sequencing templates. Optionally, the hairpins or stem-loop structures comprise different sequences or "barcodes" that allow sequenced-based identification of the origin of the fragment contained therein. For example, the amplified fragments will be ligated to a first pair of hairpins, and the unamplified fragments will be ligated to a second pair of hairpins, wherein the sequence of the first pair is distinct from the sequence of the second pair, e.g., in either one or both hairpins within each pair. In such embodiments, the two template preparations can be included in the same sequencing reaction, e.g., in an arrayed format, and the resulting sequence information can be analyzed to both determine whether a particular fragment is from the amplified or unamplified aliquot, and to identify modifications present in the unamplified fragments, and therefore the original nucleic acid sample. Sequencing both amplified and unamplified fragments together is particularly beneficial to ensure that sequencing reaction conditions are identical for both, thereby reducing experimental variation. Other alterations to the described methods will be recognized by those of ordinary skill in the art in light of the teachings herein. For example, the sequence determination can be carried out by other methodologies well known in the art.

IX. Data Analysis

Analysis of the data generated by the methods described herein is generally performed using software and/or statistical algorithms that perform various data conversions, e.g., conversion of signal emissions into basecalls, conversion of basecalls into consensus sequences for a nucleic acid template, and conversion of various aspects of the basecalls and/or consensus sequence to derive a reliability metric for the resulting values. Such software, statistical algorithms, and use thereof are described in detail, e.g., in U.S. Patent Publication No. 20090024331 and U.S. Ser. No. 61/116,439, the disclosures of which are incorporated herein by reference in their entireties for all purposes. Specific methods for discerning altered nucleotides in a template nucleic acid are provided in U.S. Ser. No. 61/201,551, filed Dec. 11, 2008, and incorporated herein by reference in its entirety for all purposes. These methods include use of statistical classification algorithms that analyze the signal from a single-molecule sequencing technology and detect significant changes in one or more aspects of signal morphology, variation of reaction conditions, and adjustment of data collection parameters to increase sensitivity to changes in signal due to the presence of modified or damaged nucleotides.

In certain aspects, the invention provides methods for detecting changes in the kinetics (e.g., slowing or pausing) or other reaction data for real-time DNA sequencing. As discussed at length above, detection of a change in such sequencing applications can be indicative of secondary structure in the template, the presence of modifications in the template, the presence of an agent bound to the template, and the like. It is appreciated that the kinetic activity of single molecules does not follow the regular and simple picture implied by traditional chemical kinetics, a view dominated by single-rate exponentials and the smooth results of ensemble averaging. In a large multi-dimensional molecular system, such as the polymerase-DNA complex, there are processes taking place on many different time scales, and the resultant kinetic picture can be quite complex at the molecular level. (See, e.g., Herbert, et al. (2008) Ann Rev Biochem 77:149.) As such, a real-time single-molecule sequencing technology should be adaptable to such non-exponential behavior. For example, pauses during a real-time sequencing reaction are detectable as regions in the trace of observed signals over time in which it appears that the enzyme has significantly slowed as compared to the average rate of incorporation. As such, methods are provided to analyze the data generated in the vicinity of a pause site, and in particular algorithmic methods for classifying and removing or down-weighting the occurrence of pauses in the context of single-molecule sequencing. General information on algorithms for use in sequence analysis can be found, e.g., in Braun, et al. (1998) Statist Sci 13:142; and Durbin, et al. (1998) *Biological sequence analysis: Probabilistic models of proteins and nucleic acids*, Cambridge University Press: Cambridge, UK.

Figure 8:
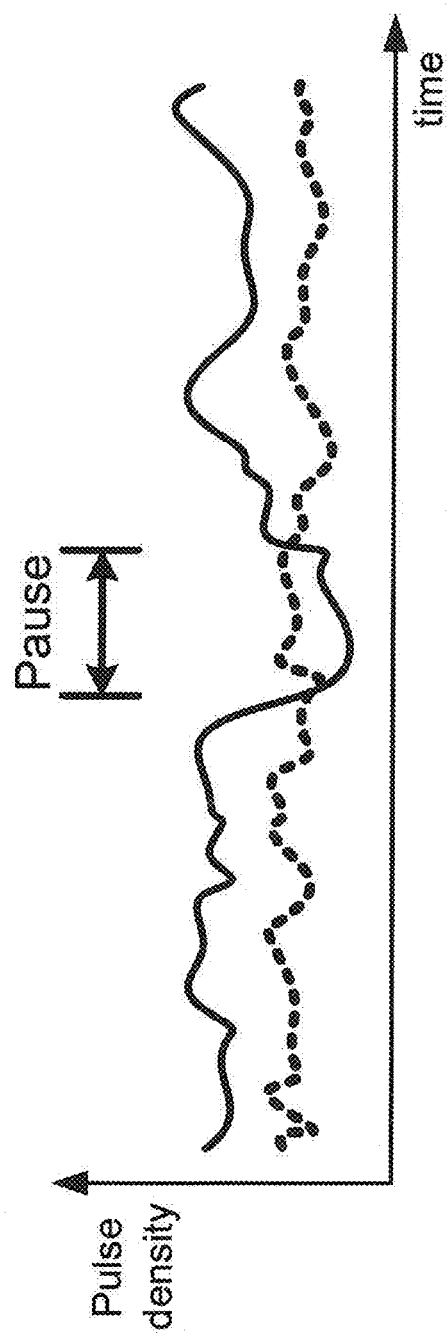
FIG. 8 illustrates an observation of true incorporations (solid line) versus stochastic pulses (dashed line) across time.

In certain preferred embodiments, the methods utilize a segmentation algorithm for discriminating pause regions in a real-time signal generated by monitoring single-molecule kinetics, in particular by monitoring DNA synthesis by DNA polymerase. The central observation is that during a pause the density of signal events (incorporations) is lowered, where the density refers to the number of events per a fixed unit of time. At the same time, stochastic events arising from Poisson processes, such as sticks (signals that do not correspond to an incorporation event, e.g., dyes that enter the detection volume but are not linked to nucleotides that are incorporated into the nascent strand) should continue at the same density as normally observed. FIG. 8 illustrates an observation of true incorporations (solid line) versus stochastic pulses (dashed line) across time. A pause is identified in the region of the trace in which the observation of true incorporations dips below the observation of stochastic pulses. As such, by observation of differences in local densities, pauses in incorporation activity can be identified.

In some embodiments, a basic detection approach uses higher order summary statistics. IPD is typically distributed exponentially with different rates assigned to different hidden states, e.g., $\lambda_C$ for unmethylated states and $\lambda_{CM}$ for methylated states. Modifications are detected by examining the ratio $\lambda_{CM}/\lambda_C$ between two samples. For example, where $\lambda_{CM}/\lambda_C \gg 1$, there is evidence of a 5-MeC in the template nucleic acid. It follows that $IPD_C \sim$ Exponential $(\lambda_C)$ and $IPD_{CM} \sim$ Exponential $(\lambda_{CM})$, then $Z = \lambda_{CM} IPD_{CM}/\lambda_C IPD_C$ has a probability density function $f(z)=1/(z+1)^2$. However, while this ratio-based approach can be effective, it is a basic approach that does not take advantage of all aspects of the reaction data.

Other features that are related to pausing and can contribute to a full model of the phenomenon. In particular, the local sequence context of the template strand can also influence and inhibit the activity of the polymerase along the template. For example, the local sequence context that influences and/or inhibits activity of the polymerase may extend for at least about one, two, three, four, five, seven, ten, fifteen, twenty nucleotide positions, and these positions may lie upstream or downstream of the modification, or may flank the modification in the template. Other known models can also be used in the methods described herein, as will be clear to one of ordinary skill upon review of the teachings herein.

In certain embodiments, a mixture model is used to specifically model the multiple states that can exist for a given site in a given sample. For example, a given site can be both methylated and unmethylated over the space of multiple molecules, and the state at a given site can also influence rate variation at neighboring sites. Assuming IPDs are distributed as described above, the probability density function for the mixture model is given by:

$$f(IPD_i|\theta) = \pi \lambda_C \exp(-\lambda_C IPD_i) + (1-\pi)\lambda_{CM} \exp(-\lambda_{CM} IPD_i), \text{ for molecules } i=1, \ldots, M.$$

$\pi$ represents the unknown fraction of molecules in a given sample that are unmethylated. $1/\lambda_C$ and $1/\lambda_{CM}$ are the means of the two exponential distributions, and $\theta=(\pi, \lambda_C, \lambda_{CM})$. Therefore, $$L = \prod_{i=1}^{M} (\pi \lambda_C \exp(-\lambda_C IPD_i) + (1-\pi)\lambda_{CM} \exp(-\lambda_{CM} IPD_i))$$

Further, consider a random class vector $C=(C_1, \ldots, C_n)$, where C can take on multiple rates. A general prior probability for a given realization of this rate class vector can be written as:

$$Pr(C=c) = \frac{e^{H(c)}}{\sum_d e^{H(d)}}.$$

The following potential function can provide a way to consider site-to-site interactions:

$$H(c) = \sum_{i=1}^{n} \lambda_{c_i} + \sum_{j=1}^{k} \sum_{i=1}^{n-j} \omega_j 1_{\{c_i = c_{i+j}\}}.$$

In a preferred embodiment, an algorithm for use in detecting changes during template-directed nucleic acid synthesis comprises the following general steps. First, a classifier is created that can distinguish between true incorporations and stochastic pulses. Features that can help discriminate between the two include, e.g., pulse height, pulse width, local signal-to-noise ratio, dye channel, and the $\chi^2$ metric for the measured spectrum. Many different statistical classification algorithms known in the art can be used in this classifier. Certain preferred algorithms include classification-and-regression trees (CART), naïve Bayesian classifiers, kernel density methods, linear discriminant functions, and neural networks. Further, the pulse classifier does not need to be particularly powerful (in an optimal specificity/sensitivity sense), because a strength of the approach relies on the greater significance associated with observing clusters of weakly significant events.

A second step is to slide a fixed-length window across the observed signal trace and count the number of incorporations versus stochastic pulses in each window using the classifier. Choice of the window size is determined by the length scale of events to be detected; a reasonable choice in practice is 10 seconds, but a practioner may increase or decrease the window size according to a particular implementation of the invention. Regions of the trace in which the stochastic pulse density exceeds the incorporation density for an extended period of time, e.g., 5-15 seconds, or more preferably about 10 seconds, are identified as corresponding to a likely pause site. These regions can be found using standard peak-finding techniques, e.g., threshold detection, finite-state machines, multi-scale methods, etc. This method has the further advantage of focusing on pause regions that have detrimental effects in the downstream use of sequencing data. The mere occurrence of a pause during sequencing is not consequential to the use of the data for DNA sequence analysis, however the occurrence of a large number of stochastic pulses in the pause region does complicate the use of the resulting data.

A variation on this exemplary algorithm is to use the time between true pulses that are identified by the classifier as a discriminator for finding pause regions, where regions that have a large difference between true pulses are candidate regions for pauses. For example, A plot of $\Delta t$ (the time between true pulses) versus time will have local maxima at the location of candidate pauses.

Figure 9:
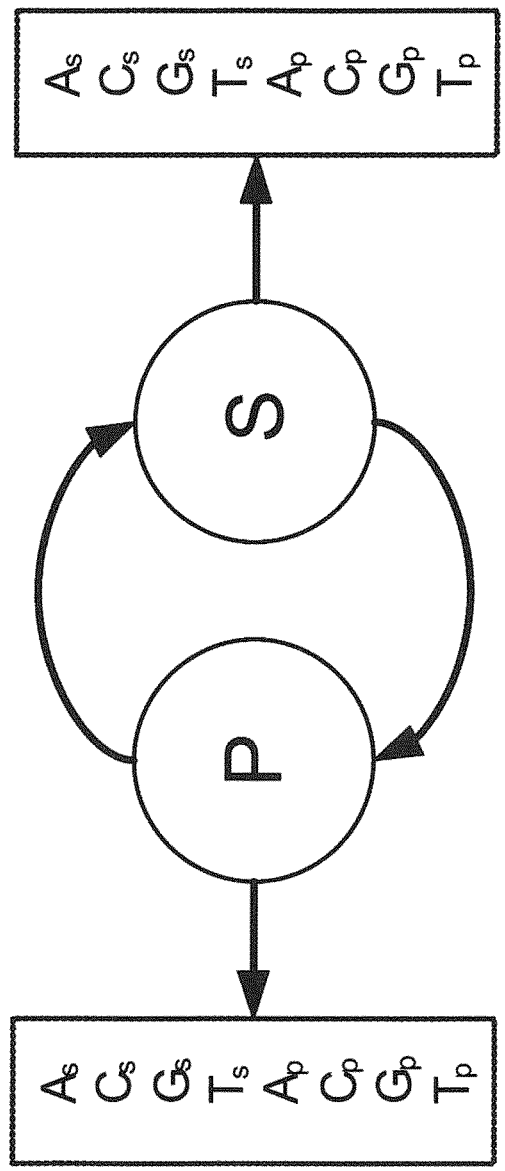
FIG. 9 provides an illustrative example of a simple hidden Markov model for classifying pause (P) versus sequencing (S) states within a sequencing trace.

A more sophisticated algorithm for use in detecting pause regions is a segmenting algorithm based on a hidden Markov model (HMM) architecture. FIG. 9 provides an illustrative example of a simple hidden Markov model for classifying pause (P) versus sequencing (S) states within a sequencing trace. The use of this model assumes that each pulse can be labeled as either a probable incorporation ($A_S$, $C_S$, $G_S$, $T_S$) or a stochastic pulse ($A_P$, $C_P$, $G_P$, $T_P$). By fitting this model on multiple instances of sequence data (using e.g. the Baum-Welch algorithm), good emission and transition probabilities that correspond to the hidden pause and sequencing states can be generated. When subsequently presented with any particular signal (observed labels), the model can be queried for the underlying sequencing of hidden states using the Viterbi algorithm. This model is more powerful than the more simple algorithmic approaches suggested above in several ways. First, this model permits the modeling of per-nucleotide likelihoods for incorporations or sticks during the pauses or sequencing states. An example where this is useful is if a stick/incorporation classifier for one nucleotide is particularly effective and if the pulses for another nucleotide are difficult to classify in this way. This model permits some nucleotide-specific differences in the classification power for stochastic pulses versus incorporations. A further advantage of this approach is that it is more adaptable to detecting regions across multiple time scales, where HMM segmentation approaches are usually better able to handle multi-time scale classification. The final assignment of pause regions is made by computing the log-odds ratio $$\log \frac{p\langle P | x_i \rangle}{p\langle S | x_i \rangle}$$

across the pulses ($x_i$) and identifying regions of high pause likelihood.

A more powerful algorithmic architecture for segmentation is the use of the conditional random field framework (CRF). The object is to predict the conditional probability of a signal arising from a pause or sequencing state given the observed pulses:

$$p\langle y | x \rangle = \frac{\exp[w^T F(x, y)]}{\sum_{y'} \exp[w^T F(x, y')]},$$

where y is the sequence of desired labels (pause, sequencing), x is the observed pulse data (both basecalls and other pulse features), w is the weight vector learned from the training data, and the F function is the feature vector. The weights in the CRF can be trained using labeled sequences using standard techniques from the CRF literature (for example, Lafferty et al (2001) Proc. 18th International Conference on Machine Learning, 282-289, which is incorporated herein by reference in its entirety for all purposes). By labeling the sequence in this way, regions of high pause probability can be identified using the methods described above. One advantage of this method is the lack of a requirement for a per-pulse classifier for distinguishing between incorporation and stochastic pulses. It can also better integrate knowledge of the inter-pulse spacing and other information, such as sequence context, into a broad model. Potential disadvantages are the large amount of training data required to build the model and the algorithmic complexity involved in constructing a CRF model.

The application of such algorithmic methods to identify pause sites and/or regions with locally high stochastic pulses in sequencing trace data is useful in a number of contexts. For example, pulses in regions that are predicted to exhibit enzyme pausing can be labeled as less confident (lower quality value) for their use in downstream analyses such as sequence variant detection in resequencing applications or overlap detection for de novo assembly. In other embodiments, pulses from regions with a high probability of containing a cluster of stochastic pulses can be removed from the reported basecalled sequence, thereby improving the accuracy of sequence data for downstream use without resorting to secondary information such as quality values. In other embodiments, the occurrence of pauses can be associated with other observables of interest, such as the probable DNA sequence or the occurrence of modified nucleotide bases. For example, sequences upstream of a pause site can be called in part based on their known effect on pausing. That is, if a pause occurs downstream of a sequence, then the sequence is more likely to be one that facilitates or exacerbates pausing than one that has no effect or that reduces the likelihood of pausing. As such, if sequencing of a modification is known to increase the likelihood of pausing, then this information can be incorporated into a Bayesian likelihood model for identifying modified bases. In further embodiments, the pause detection methods described herein can also be used to increase the understanding of the biophysics of polymerase activity, thereby providing useful feedback to efforts to better develop single-molecule, real-time sequencing techniques.

Algorithms for the identification of regions in sequence data belong to the general category of sequence labeling or segmentation algorithms, which are generally known in the art. The mapping of this problem to sliding-window analysis, HMMs, or CRFs is natural in this context. Other algorithms that approach the same problem are multiple change-point analysis such as the Gibbs sampler (see, e.g., Lee, P. M. (2004) *Bayesian Statistics: An Introduction*, Oxford University Press: New York, N.Y., the disclosure of which is incorporated herein by reference in its entirety for all purposes), or locally weighted polynomial regression (see, e.g., Braun, et al., supra).

Figure 11:
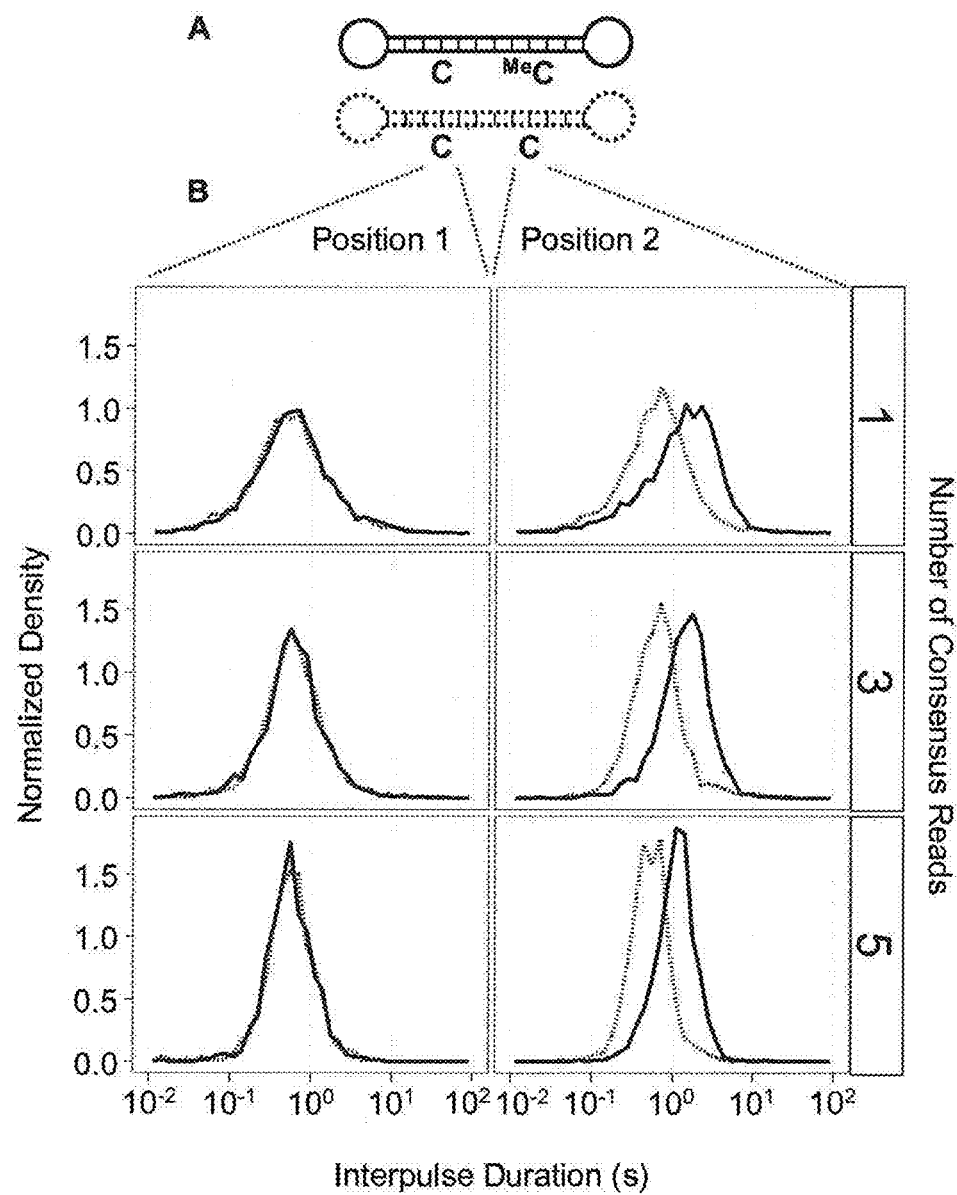
FIG. 11A provides a schematic for exemplary template nucleic acids of the invention.
FIG. 11B provides graphs plotting interpulse duration for template nucleic acids as depicted in 11A.
Figure 14:
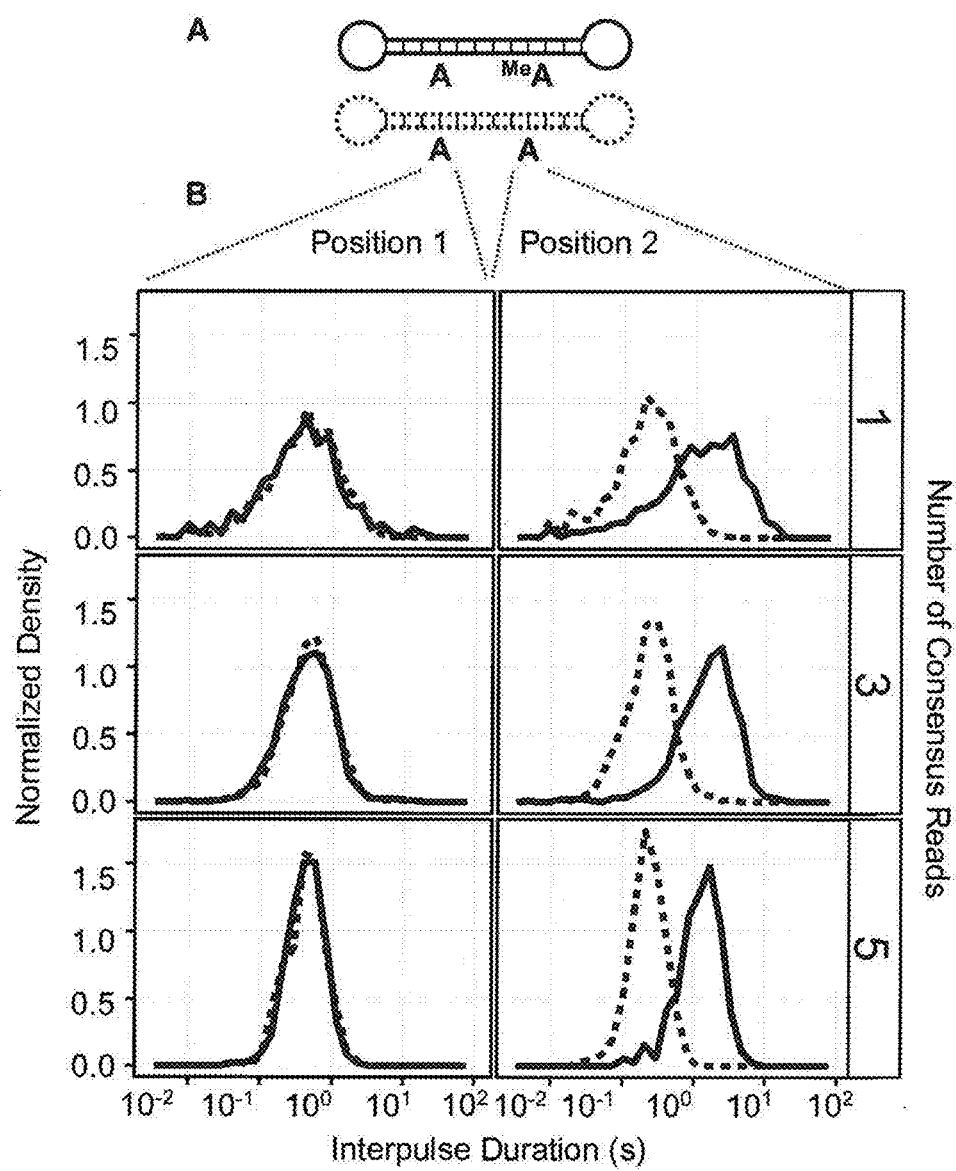
FIG. 14A provides a schematic for exemplary template nucleic acids of the invention.
FIG. 14B provides graphs plotting interpulse duration for template nucleic acids as depicted in 14A.
FIG. 14C provides a ROC curve for the data provided in 14B.

In general, data analysis methods benefit when the sequencing technology generates redundant sequence data for a given template molecule, e.g. by molecular redundant sequencing as described above. The distribution of IPDs for each read at that position is an exponential. The decay constant for the exponential of a methylated base and for that of an unmethylated base may be different. However, because of the large amount of overlap between two exponentials, it is still challenging to use one read to distinguish between the two populations. However, if one takes the mean of multiple reads at a single position, the distribution of this mean is a gamma function (convolution of several exponentials), which is more Gaussian-like and better separated than exponentials. This enables better distinguishability of the two populations. For example, FIG. 14 provides actual data showing that for two different positions in a single circular template, one always unmethylated, and one differentially methylated, an increase in the number of reads for the template corresponds to an increased resolution between IPDs for methylated vs. unmethylated adenosines. If the underlying distributions are exponential, as just discussed, then the mean value is the only metric that can be used for making the distinction (the standard deviation is the same as the mean). If the distribution is non-exponential for each read position, as it would be for the methylcytosine IPD' that is weighted over numerous neighboring positions and thus itself has a gamma-like distribution, then when doing consensus reads of the same position, one can take into account the mean of the gamma-like weighted IPD' distributions along with other information, e.g. its standard deviation, its skewness, or other characteristics of the distribution. FIG. 11 shows actual molecular consensus distributions for methylcytosine, given the underlying gamma-like weighted IPD' distributions of individual reads, but in this figure only the means of these underlying distributions were utilized. The plotted distributions could become even more well-separated if other characteristics had been taken into account. The data used to generate FIGS. 14 and 11 is more fully described in the Examples herein.

In certain embodiments, methods may be employed that use weighted sums of signal features at multiple positions to determine the status of a base, e.g., whether or not it is methylated in a template nucleic acid. In particular, interpulse duration (IPD) information from multiple positions can be used to determine whether or not a given cytosine is methylated, e.g., by comparing nascent strand synthesis data for a differentially methylated template (Me+) to such data for a fully unmethylated template (Me−). In certain preferred embodiments, a pseudo IPD is created for a given template position that is actually a weighted sum of the IPDs for the surrounding positions. More specifically, $$IPD'_j = \sum_i w_i \times \frac{IPD_{ji}}{\langle IPD_j \rangle_{Me-}},$$

where j is the index of the cytosine in question; i is an index that ranges over all the neighboring positions that yield a change in IPD due to cytosine being either methylated or unmethylated; and $\langle IPD_i \rangle_{Me}$, is the average IPD at that particular position in the Me− template. The individual weights for the multiple positions (all together which would likely sum to 1) could be based on a combination of the following metrics, assuming we are comparing two templates that are identical aside for one being methylated and the other being unmethylated at a given position: the ratio of or difference in IPD between the two templates at that given position; the statistical significance of the distinguishability between the IPD distributions of the two templates at that given positions; the number of observations used when creating the IPD distributions; and the neighboring sequence context. An example $w_i$ could be $$w_i = \log\left[\frac{\langle IPD_i \rangle_{Me+}}{\langle IPD_i \rangle_{Me-}}\right].$$

This signal can also be weighted by the prior probability of seeing a Me+ signal.

In certain aspects, the invention provides a general-purpose approach to discriminating between Me+ and Me− using features in a real-time sequencing-by-synthesis trace comprising signals emitted during the incorporation of optically detectable nucleotides into a nascent strand by a polymerase enzyme. Such traces and various methods of analysis thereof are further described elsewhere, e.g., in U.S. Patent Publication No. 20090024331, incorporated herein by reference in its entirety for all purposes. A first stage of this approach includes the development of a classifier for distinguishing methylated from unmethylated cytosines in a nucleic acid template. A set of features is measured for every pulse (discrete event or signal) in the trace. For example, a set of measurable features might be {pulse width, pulse duration, pulse height, pulse amplitude variability}. Call the values of these features $f_1^i, f_2^i, \ldots, f_k^i$, for pulse i. For each cytosine pulse in the methylated and unmethylated template data sets (which may or may not be restricted to CpG), tabulation is performed for the local pulse features $$\vec{f} = \{f_1^{i-3}, f_2^{i-3}, \ldots, f_k^{i-1}, f_1^i, f_2^i, \ldots, f_k^i, \ldots, f_1^{i+3}, f_2^{i+3}, \ldots, f_k^{i+3}\}.$$

In this example, a local context extending 3 pulses to the left and right of the pulse of interest is assumed, but this context size is flexible and, in certain embodiments, can be application-specific.

The observed data likelihoods $p(\vec{f}|Me+)$ and $p(\vec{f}|Me-)$ are derived, e.g., by a kernel density method or simple binning and tabulation of the features. Thus, a generalized signal for determining methylation status on the trace has been determined:

$$w_i = \log\left[\frac{p(\vec{f}|Me+)p(Me+)}{p(\vec{f}|Me-)p(Me-)}\right],$$

where p(Me+) and p(Me−) are the prior probabilities of methylated or un-methylated positions, respectively.

Various standard classification algorithm development techniques known to those of ordinary skill in the art may be applied to refine this approach, both to reduce training set bias and to improve sensitivity. Such techniques include but are not limited to cross-validation, boosting, and bootstrap aggregating (bagging). In certain embodiments, the set of feature inputs is restricted to those that are most correlated with the Me+ and Me− status of a position. In certain embodiments, the major component in a principal components analysis can serve as a better weighted combination of the most important features. In further embodiments, leave-one-out cross-validation can be valuable in selecting a robust predictive algorithm, e.g., by mitigating overfitting to the observed data that can occur when developing a classifier on a training set. Further, in some embodiments a boosting approach (training of a hierarchy of classifiers on the progressively more difficult regions of feature space) is applied to improve sensitivity.

More sophisticated signals can be employed to detect multiple, closely spaced CpGs. In certain embodiments, the data likelihoods described above can be measured for the case of two CpG sites with a known methylation state located a known distance apart, e.g., 2 base pairs apart. The signal generalizes to $$w_i = \underset{\mu \in \{++,+-,-+,--\}}{\operatorname{argmax}} \log\left[\frac{p(\vec{f}_\alpha, \vec{f}_\beta|\mu)p(\mu)}{\sum_{\mu'} p(\vec{f}_\alpha, \vec{f}_\beta|\mu')p(\mu')}\right],$$

where p(μ) and p(μ') are the prior probabilities of (methylated, un-methylated) configurations (this joint distribution would be assumed to be independent unless otherwise shown).

Figure 15:
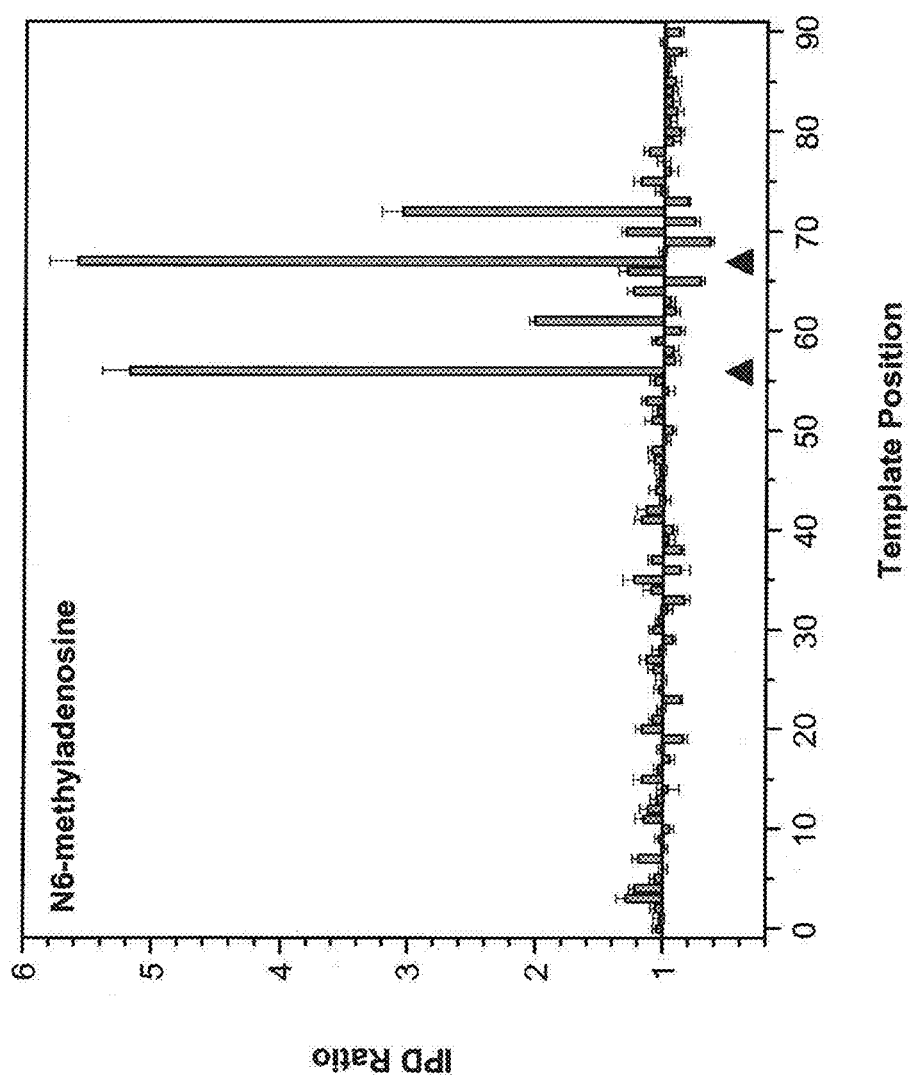
FIG. 15 provides a graph plotting IPD ratio against template position for a template nucleic acid comprising $N^6$-methyladenosine modifications.

Although described primarily in the context of detection of methyl cytosine, these methods are also applicable to methyl-adenosine or any other base modification for which IPDs are used as a metric for detection. FIG. 15 provides data showing differences between ratios of IPDs for methylated adenosines and unmethylated adenosines in a template nucleic acid, and the data used to generate FIG. 15 is further described in the Examples herein. This data also shows that $N^6$-methyladenosine, like methylcytosine, has an effect on IPD not only at the methylated base but also at multiple, neighboring positions, as well. Further, in light of the above teachings it will be clear to one of ordinary skill that the approach can be extended to pulse metrics other than IPD, such as pulse width, branch rate, mismatch rate, deletion rate, etc. In addition, the general classifier approach suggested in steps 2+3 can be implemented with many standard statistical classification algorithms, i.e. linear discriminant analysis, multi-dimensional regression, kernel methods, classification and regression trees, neural networks, and support vector machines. The approach can also incorporate data from multiple strands of a duplex template. For example, because the CG sequence for cytosine methylation and the GATC sequence for adenosine methylation is the same on the reverse complement strand, these bases can be methylated on both complementary strands. If the general statistical distribution for the fraction of sites that are hemi-methylated vs. fully methylated is known, then information regarding IPD or other metrics gained from the complementary strand can be used to increase the accuracy with which a call is made on a particular strand. For example, if after analyzing each strand separately it is concluded that there is a 95% chance that stand A is methylated and a 55% chance that complementary strand B is methylated, but it is known that there is a 80% chance that if one strand is methylated then so is the other, then the confidence in calling strand B as methylated is increased.

Further, the incorporation of a double-stranded nucleic acid fragment into a closed circular single-stranded template (e.g., as described in U.S. Patent Publication No. 20090298075) elegantly allows comparison of the polymerase kinetics on the forward and reverse strand. Since the forward and reverse strands are reverse complements of each other, one must construct the expectation of the ratios of the parameters of interest (e.g., pulse width, IPD, etc.) from an entirely unmodified sample, e.g., using amplification to produce amplicons that do not comprise the modification(s). The subsequent analysis on the sample comprising the modifications comprises performing a likelihood analysis that the ratio observed is sufficiently different from the expected ratio. This means that all other aspects of the experiment are normalized out since they are identical for sequencing on the forward and reverse strands. For example, in SMRT™ sequencing, such aspects of the experiment include, but are not limited to, the specific polymerase, its position in the reaction site (e.g., within a ZMW), the illumination (e.g., beamlet alignment, power, wavelengths, etc.), temperature at that reaction site, local concentrations of reactants (e.g., polymerase, nucleotides, etc.), and the like. Each time the modification is sequenced as the polymerase repeatedly translocates around the template, the sequence data generated directly adds to the confidence in the ration and informs the p-value confidence in whether a modification is present at a specific position within the template.

As noted elsewhere herein, another modified base for which IPDs may be used as a metric for detection is 5-hydroxymethylcytosine (5-hmC). It was recently found to be abundant in human and mouse brains, as well as in embryonic stem cells (see, e.g., Kriaucionis, et al. (2009) "The nuclear DNA base 5-hydroxymethylcytosine is present in Purkinje neurons and the brain" *Science* 324 (5929): 929-30; and Tahiliani M et al. (May 2009) "Conversion of 5-methylcytosine to 5-hydroxymethylcytosine in mammalian DNA by MLL partner TET1" *Science*. 324 (5929): 930-35, incorporated herein by reference in their entireties for all purposes). In mammals, it can be generated by oxidation of 5-methylcytosine, a reaction mediated by the Tet family of enzymes. Conventional bisulfite sequencing does not effectively distinguish 5-hmC from 5-MeC because 5-hmC tends to remain unmodified like 5-MeC. As such, mass spectrometry is the typical means of detecting 5-hmC in a nucleic acid sample. The methods described herein provide a high-throughput, real-time method to distinguish between C, 5-MeC, and 5-hmC by monitoring deviations from normal polymerase kinetics, including IPD and pulse width.

Experiments were carried out to test the ability of the methods of the invention to distinguish between 5-MeC and 5-hmC, and it was found that 5-hmC causes an increase in IPD at certain positions surrounding the 5-hmC site in the template, and also decreases the pulse width at that position. Further, the data generated suggests that 5-hmC may also increase the pulse width at the position following the 5-hmC site. Both the difference in IPD and the difference in pulse width between C and 5-hmC were larger in magnitude than were the differences in IPD and pulse width between C and 5-MeC, and these larger magnitudes are likely to make 5-hmC even more detectable than 5-MeC. Without being bound by theory, the reason for the higher magnitude differences for these two measures may be due to the additional oxygen atom present in 5-hmC as compared to 5-MeC. This additional oxygen could yield additional steric and charge-based interactions between the polymerase and the DNA template that slow the binding and/or incorporation of the complementary base into the nascent strand.

Based on the findings that indicate the easier detection of 5-hmC as compared to 5-MeC, in certain embodiments template nucleic acids can be treated to convert 5-MeC to the more easily detected 5-hmC, e.g., by treatment with an enzyme such as TET1, which converts 5-methylcytosine to 5-hydroxymethylcytosine in mammalian DNA (see, e.g., Tahiliani M et al., supra). Although this technique would not permit distinction between 5-MeC and 5-hmC in the template (since the 5-MeC converted to 5-hmC would be indistinguishable from any 5-hmC originally present in the template), it will nonetheless be useful for facilitating detection 5-MeC patterns in template nucleic acids with the caveat that the patterns so discovered may, in vivo, also include 5-hmC bases.

In order to maximally use the IPD and pulse width signals from multiple positions surrounded the 5-hmC site, one could use a technique to find the optimal weighting of different positions for IPD and pulse width in order to distinguish 5-hmC, 5-MeC, and C from one another. An example of one such technique is principle component analysis, and others are known in the art. Principle component analysis can be described as finding the eigenvector (using each metric such as IPD or pulse width at each position as a different basis vector, such that if you have 10 positions in question and two metrics, your basis will have 2×10=20 dimensions) with the greatest eigenvalue. For a review of principle component analysis, see e.g. Jolliffe I. T. Principal Component Analysis, Series; Springer Series in Statistics, 2nd ed., Springer, N.Y., 2002, the disclosure of which is incorporated herein by reference in its entirety for all purposes.

X. Systems

The invention also provides systems that are used in conjunction with the compositions and methods of the invention in order to provide for real-time single-molecule detection of analytical reactions. In particular, such systems typically include the reagent systems described herein, in conjunction with an analytical system, e.g., for detecting data from those reagent systems. In certain preferred embodiments, analytical reactions are monitored using an optical system capable of detecting and/or monitoring interactions between reactants at the single-molecule level. For example, such an optical system can achieve these functions by first generating and transmitting an incident wavelength to the reactants, followed by collecting and analyzing the optical signals from the reactants. Such systems typically employ an optical train that directs signals from the reactions to a detector, and in certain embodiments in which a plurality of reactions is disposed on a solid surface, such systems typically direct signals from the solid surface (e.g., array of confinements) onto different locations of an array-based detector to simultaneously detect multiple different optical signals from each of multiple different reactions. In particular, the optical trains typically include optical gratings or wedge prisms to simultaneously direct and separate signals having differing spectral characteristics from each confinement in an array to different locations on an array based detector, e.g., a CCD, and may also comprise additional optical transmission elements and optical reflection elements.

An optical system applicable for use with the present invention preferably comprises at least an excitation source and a photon detector. The excitation source generates and transmits incident light used to optically excite the reactants in the reaction. Depending on the intended application, the source of the incident light can be a laser, laser diode, a light-emitting diode (LED), a ultra-violet light bulb, and/or a white light source. Further, the excitation light may be evanescent light, e.g., as in total internal reflection microscopy, certain types of waveguides that carry light to a reaction site (see, e.g., U.S. Application Pub. Nos. 20080128627, 20080152281, and 200801552280), or zero mode waveguides, described below. Where desired, more than one source can be employed simultaneously. The use of multiple sources is particularly desirable in applications that employ multiple different reagent compounds having differing excitation spectra, consequently allowing detection of more than one fluorescent signal to track the interactions of more than one or one type of molecules simultaneously (e.g., multiple types of differentially labeled reaction components). A wide variety of photon detectors or detector arrays are available in the art. Representative detectors include but are not limited to an optical reader, a high-efficiency photon detection system, a photodiode (e.g. avalanche photo diodes (APD)), a camera, a charge-coupled device (CCD), an electron-multiplying charge-coupled device (EMCCD), an intensified charge coupled device (ICCD), and a confocal microscope equipped with any of the foregoing detectors. For example, in some embodiments an optical train includes a fluorescence microscope capable of resolving fluorescent signals from individual sequencing complexes. Where desired, the subject arrays of optical confinements contain various alignment aides or keys to facilitate a proper spatial placement of the optical confinement and the excitation sources, the photon detectors, or the optical train as described below.

The subject optical system may also include an optical train whose function can be manifold and may comprise one or more optical transmission or reflection elements. Such optical trains preferably encompass a variety of optical devices that channel light from one location to another in either an altered or unaltered state. First, the optical train collects and/or directs the incident wavelength to the reaction site (e.g., optical confinement). Second, it transmits and/or directs the optical signals emitted from the reactants to the photon detector. Third, it may select and/or modify the optical properties of the incident wavelengths or the emitted wavelengths from the reactants. Illustrative examples of such optical transmission or reflection elements are diffraction gratings, arrayed waveguide gratings (AWG), optical fibers, optical switches, mirrors (including dichroic mirrors), lenses (including microlenses, nanolenses, objective lenses, imaging lenses, and the like), collimators, optical attenuators, filters (e.g., polarization or dichroic filters), prisms, wavelength filters (low-pass, band-pass, or high-pass), planar waveguides, wave-plates, delay lines, and any other devices that guide the transmission of light through proper refractive indices and geometries. One example of a particularly preferred optical train is described in U.S. Patent Pub. No. 20070036511, filed Aug. 11, 2005, and incorporated by reference herein in its entirety for all purposes.

In a preferred embodiment, a reaction site (e.g., optical confinement) containing a reaction of interest is operatively coupled to a photon detector. The reaction site and the respective detector can be spatially aligned (e.g., 1:1 mapping) to permit an efficient collection of optical signals from the reactants. In certain preferred embodiments, a reaction substrate is disposed upon a translation stage, which is typically coupled to appropriate robotics to provide lateral translation of the substrate in two dimensions over a fixed optical train. Alternative embodiments could couple the translation system to the optical train to move that aspect of the system relative to the substrate. For example, a translation stage provides a means of removing a reaction substrate (or a portion thereof) out of the path of illumination to create a non-illuminated period for the reaction substrate (or a portion thereof), and returning the substrate at a later time to initiate a subsequent illuminated period. An exemplary embodiment is provided in U.S. Patent Pub. No. 20070161017, filed Dec. 1, 2006.

In particularly preferred aspects, such systems include arrays of reaction regions, e.g., zero mode waveguide arrays, that are illuminated by the system, in order to detect signals (e.g., fluorescent signals) therefrom, that are in conjunction with analytical reactions being carried out within each reaction region. Each individual reaction region can be operatively coupled to a respective microlens or a nanolens, preferably spatially aligned to optimize the signal collection efficiency. Alternatively, a combination of an objective lens, a spectral filter set or prism for resolving signals of different wavelengths, and an imaging lens can be used in an optical train, to direct optical signals from each confinement to an array detector, e.g., a CCD, and concurrently separate signals from each different confinement into multiple constituent signal elements, e.g., different wavelength spectra, that correspond to different reaction events occurring within each confinement. In preferred embodiments, the setup further comprises means to control illumination of each confinement, and such means may be a feature of the optical system or may be found elsewhere is the system, e.g., as a mask positioned over an array of confinements. Detailed descriptions of such optical systems are provided, e.g., in U.S. Patent Pub. No. 20060063264, filed Sep. 16, 2005, which is incorporated herein by reference in its entirety for all purposes.

The systems of the invention also typically include information processors or computers operably coupled to the detection portions of the systems, in order to store the signal data obtained from the detector(s) on a computer readable medium, e.g., hard disk, CD, DVD or other optical medium, flash memory device, or the like. For purposes of this aspect of the invention, such operable connection provides for the electronic transfer of data from the detection system to the processor for subsequent analysis and conversion. Operable connections may be accomplished through any of a variety of well known computer networking or connecting methods, e.g., Firewire®, USB connections, wireless connections, WAN or LAN connections, or other connections that preferably include high data transfer rates. The computers also typically include software that analyzes the raw signal data, identifies signal pulses that are likely associated with incorporation events, and identifies bases incorporated during the sequencing reaction, in order to convert or transform the raw signal data into user interpretable sequence data (see, e.g., Published U.S. Patent Application No. 2009-0024331, the full disclosure of which is incorporated herein by reference in its entirety for all purposes).

Exemplary systems are described in detail in, e.g., U.S. patent application Ser. No. 11/901,273, filed Sep. 14, 2007 and U.S. patent application Ser. No. 12/134,186, filed Jun. 5, 2008, the full disclosures of which are incorporated herein by reference in their entirety for all purposes.

Further, the invention provides data processing systems for transforming raw data generated in an analytical reaction into analytical data that provides a measure of one or more aspects of the reaction under investigation, e.g., transforming signals from a sequencing-by-synthesis reaction into nucleic acid sequence read data, which can then be transformed into consensus sequence data. In certain embodiments, the data processing systems include machines for generating nucleic acid sequence read data by polymerase-mediated processing of a template nucleic acid molecule (e.g., DNA or RNA). The nucleic acid sequence read data generated is representative of the nucleic acid sequence of the nascent polynucleotide synthesized by a polymerase translocating along a nucleic acid template only to the extent that a given sequencing technology is able to generate such data, and so may not be identical to the actual sequence of the nascent polynucleotide molecule. For example, it may contain a deletion or a different nucleotide at a given position as compared to the actual sequence of the polynucleotide, e.g., when a nucleotide incorporation is missed or incorrectly determined, respectively. As such, it is beneficial to generate redundant nucleic acid sequence read data, and to transform the redundant nucleic acid sequence read data into consensus nucleic acid sequence data that is generally more representative of the actual sequence of the polynucleotide molecule than nucleic acid sequence read data from a single read of the nucleic acid molecule. Redundant nucleic acid sequence read data comprises multiple reads, each of which includes at least a portion of nucleic acid sequence read that overlaps with at least a portion of at least one other of the multiple nucleic acid sequence reads. As such, the multiple reads need not all overlap with one another, and a first subset may overlap for a different portion of the nucleic acid sequence than does a second subset. Such redundant sequence read data can be generated by various methods, including repeated synthesis of nascent polynucleotides from a single nucleic acid template, synthesis of polynucleotides from multiple identical nucleic acid templates, or a combination thereof.

In another aspect, the data processing systems can include software and algorithm implementations provided herein, e.g. those configured to transform redundant nucleic acid sequence read data into consensus nucleic acid sequence data, which, as noted above, is generally more representative of the actual sequence of the nascent polynucleotide molecule than nucleic acid sequence read data from a single read of a single nucleic acid molecule. Further, the transformation of the redundant nucleic acid sequence read data into consensus nucleic acid sequence data identifies and negates some or all of the single-read variation between the multiple reads in the redundant nucleic acid sequence read data. As such, the transformation provides a representation of the actual nucleic acid sequence of the nascent polynucleotide complementary to the nucleic acid template that is more accurate than a representation based on a single read.

Various methods and algorithms for data transformation employ data analysis techniques that are familiar in a number of technical fields, and are generally referred to herein as statistical analysis. For clarity of description, details of known techniques are not provided herein. These techniques are discussed in a number of available reference works, such as those provided in U.S. Patent Publication No. 20090024331 and U.S. Ser. No. 61/116,439, filed Nov. 20, 2008, the disclosures of which are incorporated herein by reference in their entireties for all purposes.

The software and algorithm implementations provided herein are preferably machine-implemented methods, e.g., carried out on a machine comprising computer-readable medium configured to carry out various aspects of the methods herein. For example, the computer-readable medium preferably comprises at least one or more of the following: a) a user interface; b) memory for storing raw analytical reaction data; c) memory storing software-implemented instructions for carrying out the algorithms for transforming the raw analytical reaction data into transformed data that characterizes one or more aspects of the reaction (e.g., rate, consensus sequence data, etc.); d) a processor for executing the instructions; e) software for recording the results of the transformation into memory; and f) memory for recordation and storage of the transformed data. In preferred embodiments, the user interface is used by the practitioner to manage various aspects of the machine, e.g., to direct the machine to carry out the various steps in the transformation of raw data into transformed data, recordation of the results of the transformation, and management of the transformed data stored in memory.

As such, in preferred embodiments, the methods further comprise a transformation of the computer-readable medium by recordation of the raw analytical reaction data and/or the transformed data generated by the methods. Further, the computer-readable medium may comprise software for providing a graphical representation of the raw analytical reaction data and/or the transformed data, and the graphical representation may be provided, e.g., in soft-copy (e.g., on an electronic display) and/or hard-copy (e.g., on a print-out) form.

The invention also provides a computer program product comprising a computer-readable medium having a computer-readable program code embodied therein, the computer readable program code adapted to implement one or more of the methods described herein, and optionally also providing storage for the results of the methods of the invention. In certain preferred embodiments, the computer program product comprises the computer-readable medium described above.

In another aspect, the invention provides data processing systems for transforming raw analytical reaction data from one or more analytical reactions into transformed data representative of a particular characteristic of an analytical reaction, e.g., an actual sequence of one or more template nucleic acids analyzed, a rate of an enzyme-mediated reaction, an identity of a kinase target molecule, and the like. Such data processing systems typically comprise a computer processor for processing the raw data according to the steps and methods described herein, and computer usable medium for storage of the raw data and/or the results of one or more steps of the transformation, such as the computer-readable medium described above.

Figure 10:
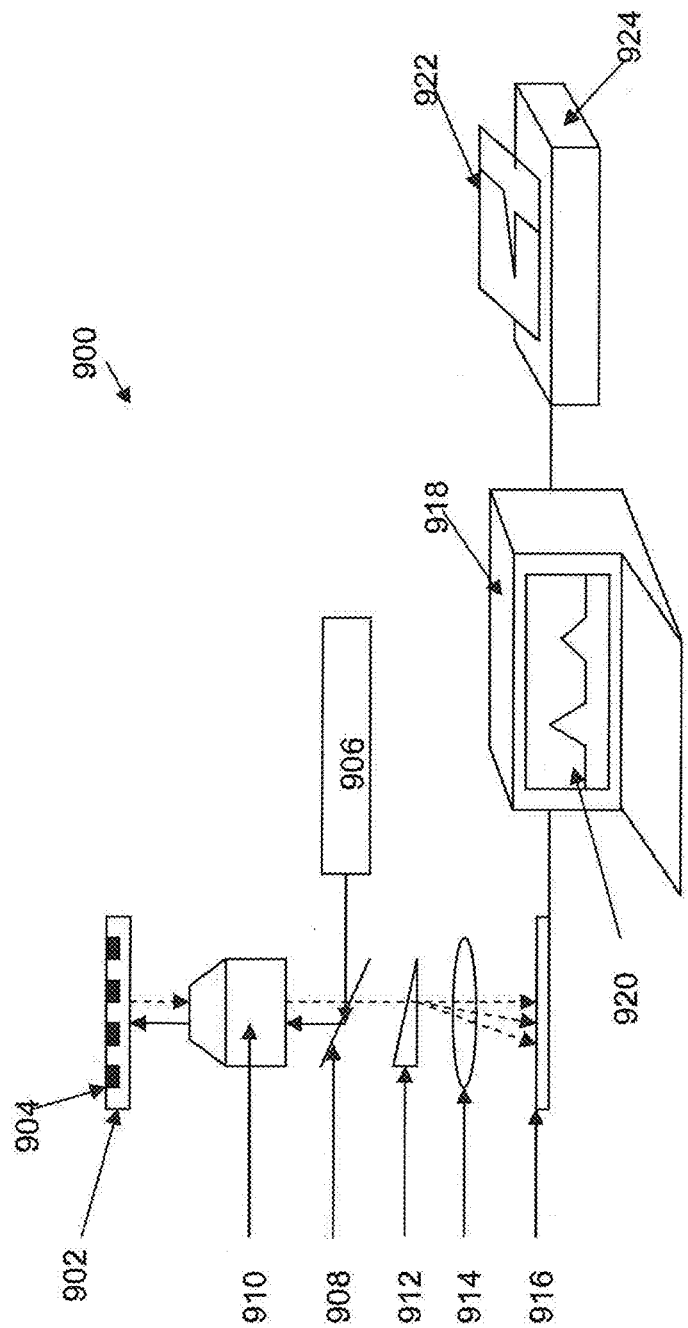
FIG. 10 provides an illustrative example of a system of the invention.

As shown in FIG. 10, the system 900 includes a substrate 902 that includes a plurality of discrete sources of chromophore emission signals, e.g., an array of zero mode waveguides 904. An excitation illumination source, e.g., laser 906, is provided in the system and is positioned to direct excitation radiation at the various signal sources. This is typically done by directing excitation radiation at or through appropriate optical components, e.g., dichroic 908 and objective lens 910, that direct the excitation radiation at the substrate 902, and particularly the signal sources 904. Emitted signals from the sources 904 are then collected by the optical components, e.g., objective 910, and passed through additional optical elements, e.g., dichroic 908, prism 912 and lens 914, until they are directed to and impinge upon an optical detection system, e.g., detector array 916. The signals are then detected by detector array 916, and the data from that detection is transmitted to an appropriate data processing system, e.g., computer 918, where the data is subjected to interpretation, analysis, and ultimately presented in a user ready format, e.g., on display 920, or printout 922, from printer 924. As will be appreciated, a variety of modifications may be made to such systems, including, for example, the use of multiplexing components to direct multiple discrete beams at different locations on the substrate, the use of spatial filter components, such as confocal masks, to filter out-of focus components, beam shaping elements to modify the spot configuration incident upon the substrates, and the like (See, e.g., Published U.S. Patent Application Nos. 2007/0036511 and 2007/095119, and U.S. patent application Ser. No. 11/901,273, all of which are incorporated herein by reference in their entireties for all purposes.)

XI. Bar Coding Applications

Many genomic applications use unique non-natural DNA sequences ("bar codes") to provide sequence-encoded sample tracking. DNA bar codes are designed to be highly detectable against the dominant sequence composition expected for a particular genomic sample. Current methods rely exclusively on the differences in the base sequence composition of the bar codes. However, these base-sequence-based bar-coding methods can fail due to base-calling errors that are inherent to in single-molecule sequencing methods, thereby limiting the ability to experimentally distinguish the bar codes from each other and from the biological nucleic acid under investigation.

In certain aspects, the present invention provides methods for improving the ability to distinguish between different bar codes, as well as between bar code sequence reads and template sequence reads. In certain embodiments, the methods comprise addition of modifications to a bar code sequence in order to facilitate detection during single-molecule sequencing. For example, a bar code sequence can be subjected to methylation, hydroxymethylation, glycosylation, or addition of other moieties that cause a distinct change in polymerase kinetics. In other embodiments, a bar code sequence can be modified to contain non-natural bases. (See, e.g., Krueger, et al. (2009) Chem. Biol. 16(3):242-248, incorporated herein by reference in its entirety for all purposes.) Alternatively, a bar code sequence can comprise a binding site for a binding agent that, when bound to the template, detectably alters polymerase activity. Other methods for modifying nucleic acids to alter the kinetic signature of a polymerase during nascent strand synthesis described elsewhere herein can also be used. During a sequencing reaction, the resulting bar-code sequence read is identifiable not only on the basis of the base sequence information generated, but also on the basis of the activity of the polymerase enzyme as it processed the template molecule.

XII. Metagenomic Identification

Metagenomics is an important, emerging field. For example, researchers are interested in characterizing the human microbiome in both healthy and diseased individuals. Determining the identity and distribution of microbial organisms from a metagenomic sample can be challenging using primary sequence information alone. SMRT™ sequencing provides reaction data related to both reaction kinetics and primary sequence information, which can provide information about DNA methylation or modifications. In particular, one can utilize the additional reaction kinetics data provided by SMRT™ sequencing to aid in metagenomic analysis and identification. For example, if a particular organism's genome is known to have a specific DNA methylation pattern that is distinct from another organism, despite their primary sequences being very similar, the kinetic signatures can be detected by SMRT™ sequencing and used to help identify the organism by association with the known methylation patterns. Furthermore, various DNA modifications have different kinetic signatures as detected by SMRT™ sequencing, enabling them to be distinguished from one another. Coupled with the fact that some organisms contain certain DNA modifications while others do not, this could enhance metagenomic analysis. For example, it is known that certain bacterial phases have glucosylated-hydroxymethylcytosine in their genomes, whereas certain bacteria contain $N^6$-methyladenosine, 5-methylcytosine, and N4-methylcytosine, and certain trypanosome contain glucosylated-hydroxymethyluracil (Base J), and other organisms may contain ribonucleotides in their genomes. Furthermore, some organisms' genomes may be more susceptible to damage (e.g., 8-oxoG, thymidine dimers) than others. Detection of the kinetic signature from one of these DNA modifications makes it more likely that the read came from a specific organism, even if the primary sequence itself is not unique enough to identify with a specific organism. Much metagenomic analysis is performed on ribosomal RNA (rRNA), which is known to contain many modifications (many of which could be organism-specific). This invention could also be applied to SMRT, direct RNA sequencing (10401) that does not comprise cDNA conversion, which has also been shown to have kinetic signatures sensitive to modified bases (e.g., pseudouridine).

XIII. Examples

Detection of 5-methylcytosine (5-MeC)

Methylation sequencing on a SMRT™ Sequencing platform (see, e.g., P. M. Lundquist, et al., supra) was performed on short, synthetic DNA oligos with contrived patterns of methylated and unmethylated bases, along with control sequences having the same primary sequence but without any methylation. These templates provided unequivocal fluorescence pulse patterns and tempos that demonstrated how the combination of sequence context and methylation status affected interpulse duration. For example, SMRT™ sequencing experiments were performed using synthetic DNA templates that only differed by a single methylated vs. unmethylated cytosine. The difference in average interpulse durations between the two templates was visible both at the 5-MeC position and in the vicinity of the 5-MeC position.

Because the interpulse duration between any two successive incorporation events is stochastic in nature and has an exponential distribution (Eid, et al., supra), a single sequencing measurement may not always yield enough information to determine methylation status with certainty. Therefore, in certain embodiments a highly processive, strand-displacing polymerase is used, and this polymerase carries out multiple laps of synthesis around a circular DNA template (J. Korlach, et al., Proc Natl Acad Sci USA 2008, supra). This mode of operation provides repeated sequencing of the same DNA molecule to generate multiple sequence reads, e.g., by rolling circle replication. The statistical distribution of interpulse durations obtained at a particular template site will thus indicate its methylation state.

In particular, FIG. 11A shows a schematic of two templates for use in SMRT™ sequencing. Both are comprises a double-stranded region flanked by two single-stranded hairpins or stem-loop structures. A polymerase binds to a primed location on the template, e.g., via a primer hybridized to one of the single-stranded hairpins, and commences processing the template to generate a nascent strand complementary to the strand upon which the polymerase is translocating. The strand displacement activity of the polymerase permits passage through the double-stranded region which is unwound to transform the template into a circular form. The polymerase then proceeds around the other single-stranded hairpin and on through the previously displaced strand of the double-stranded region. The polymerase can continue to process the template in a "rolling-circle" fashion to generate a concatemer comprising multiple copies of complements to both strands of the double-stranded region, as well as the hairpins. The two templates are identical except at position 2, where the top template comprises a methylated cytosine (5-MeC) and the bottom template comprises a non-methylated cytosine. (Position 1 is a non-methylated cytosine in both templates.) FIG. 11B provides an illustrative depiction of the difference in IPD for the methylated template as compared to the unmethylated template. For each row, the histograms depict the distributions of mean weighted IPD (averaged over the labeled number of circular consensus sequencing subreads (in this context, a sequence read generated from a single pass of the polymerase around the template). Specifically, "1" indicates the sequencing data was derived from a sequence read generated in a single pass around the template; "3" indicates the data was derived from a sequence read generated in three passes around the template; and "5" indicates the data was derived from a sequence read generated in five passes around the template. The data from the methylated template is shown as a solid line, and the data from the unmethylated template is shown as a dotted line. At Position 1, the distributions of weighted IPD for the two templates are very similar. At Position 2, the average weighted IPD after a single subread (top histogram) is longer in the methylated template than in the unmethylated template. After 3 and 5 circular subreads, the distributions overlap even less. The interpulse duration (IPD) was clearly lengthened by the presence of 5-MeC. These results demonstrated the ability to use SMRT™ sequencing technology to perform methylation sequencing of DNA. Weighted IPDs are described elsewhere herein.

Figure 12:
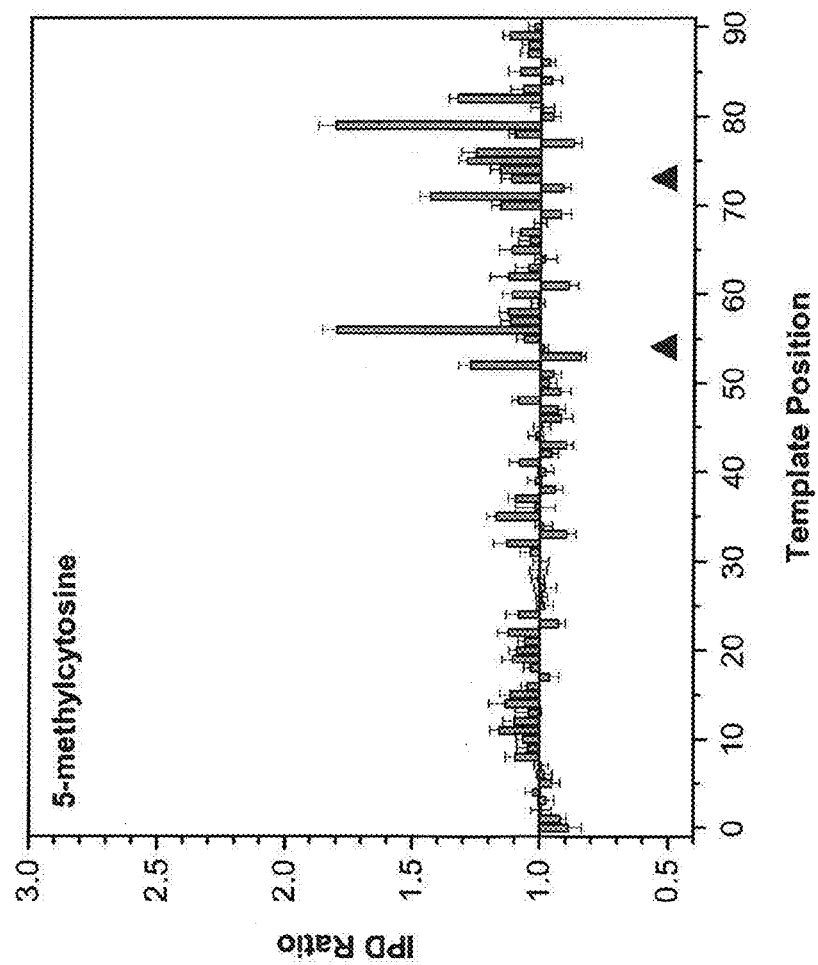
FIG. 12 provides a graph plotting IPD ratio against template position for a template nucleic acid comprising 5-methylcytosine modifications.

Further, methylcytosine was shown to have an effect on interpulse duration (IPD) not only at the methylated base, but over a range of several bases upstream and downstream of the position of the methylcytosine. Specifically, an increase in IPD was observed at some positions in the presence of methylcytosine relative to the same position in the absence of methylcytosine. FIG. 12 provides a plot depicting the ratio of the average IPD in the methylated template to the average IPD in the unmethylated template, plotted versus DNA template position. The two templates are identical except for the methylated bases in the methylated template, which are indicated by arrowheads in FIG. 12.

Figure 13:
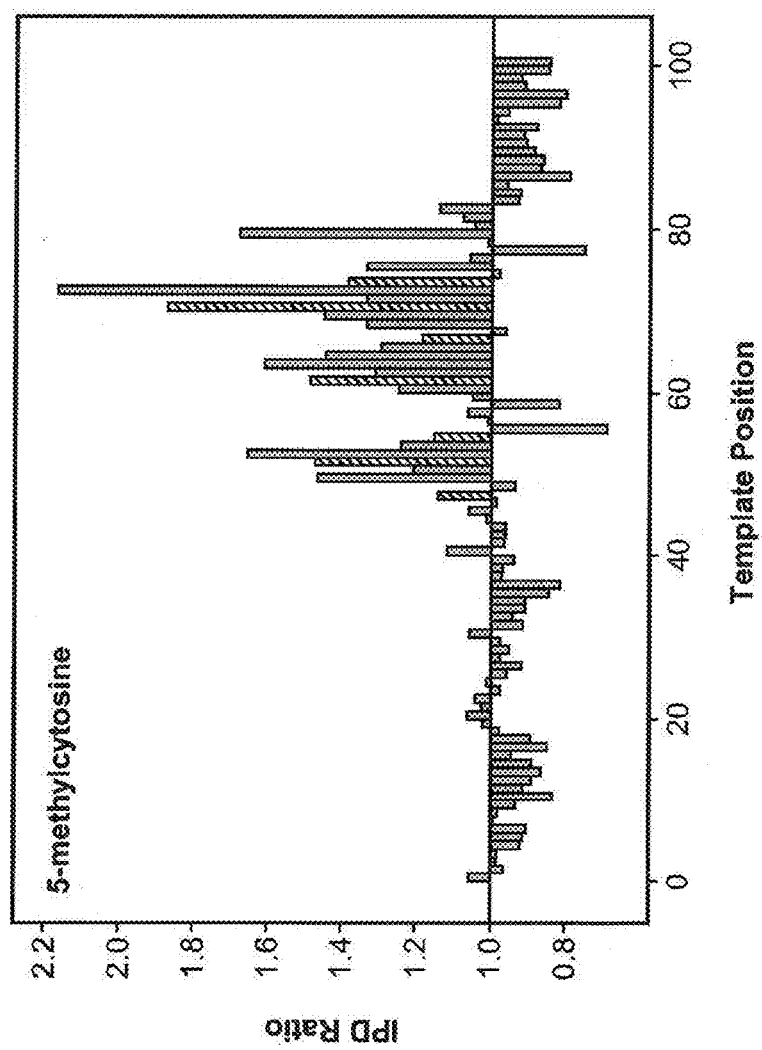
FIG. 13 provides a graph plotting IPD ratio against template position for a template nucleic acid comprising 5-methylcytosine modifications.

FIG. 13 provides another data set illustrating the ratio of IPD for a different methylated template vs. an identical but unmethylated template as a function of position. Seven cytosines (shown with crosshatching) were differentially methylated (5-MeC) between the two templates. That data clearly showed that IPD was increased in the region comprising the methylated bases. Interestingly, the effect on IPD occurred mostly downstream of the methylated positions. As such, data from nascent strand synthesis at positions in the template that are near the differentially methylated site, in addition to the differentially methylated site itself, is useful for methylation detection during real-time nascent strand synthesis.

Detection of $N^6$-methyladenosine ($N^6$-MeA)

Similar methods as those used to detect 5-MeC were used to detect $N^6$-MeA in similarly constructed template nucleic acids. FIG. 14A shows a schematic of two templates, both of which comprise a double-stranded region flanked by two single-stranded hairpins or stem-loop structures. The methylated template has an A within a GATC context at Position 1 and a $^m$A within a GATC context at Position 2, whereas the unmethylated template has an A at both positions. Otherwise, the two templates are identical. As described above, a polymerase binds to a primed location on the template and commences processing the template to generate a nascent strand, using its strand displacement activity to unwind the double-stranded region and proceed around the template. FIG. 14B shows plots of mean IPD generated from sequencing data using these two templates for varying numbers of consensus reads, as described above. The data from the methylated template is shown as a solid line, and the data from the unmethylated template is shown as a dotted line. For each row in FIG. 14B, the histograms depict the distributions of mean IPD (averaged over the labeled number of consensus sequencing subreads, i.e. the number of times the polymerase made one complete pass around the template to generate a complementary nascent strand). At Position 1, the distributions of IPD for the two templates are very similar. At Position 2, the average IPD after a single subread (top histogram) is ~5× longer in the methylated template than in the unmethylated template. After 3 and 5 circular subreads, the distributions overlap even less. The interpulse duration (IPD) was clearly lengthened by the presence of $N^6$-MeA, demonstrating that the SMRT™ sequencing technology can be used to perform methylation sequencing of DNA comprising a methylated base other than 5-MeC. Further details on the detection of $N^6$-MeA, as well as other modifications within a template nucleic acid, are provided in Flusberg, et al. (2010) Nature Methods 7(6):461-465, incorporated herein by reference in its entirety for all purposes.

Receiver operating characteristic (ROC) curves, parameterized by IPD threshold, for assigning a methylation status to an adenosine nucleotide are provided in FIG. 14C. True positive means that an $^m$A is correctly called as $^m$A, whereas a false positive means that an A is mistakenly called as $^m$A. These ROC curves, based on the IPD distributions from Position 2 in FIG. 14B, are shown for a single read (solid line), and for 3 (long-dashed line) or 5 (short-dashed line) molecular redundant sequencing reads produced by the polymerase processing the template one, three, or five times, respectively. The dotted horizontal line bisecting the graph depicts the ROC curve for randomly guessing the methylation status. The normalized area under the ROC curve is 0.80 after the first circular subread but increases to 0.92 and 0.96 after three and five circular subreads, respectively. In fact, after five subreads, >85% of $^m$A bases can be detected at this template position with a false positive rate of only ~5%.

Like methylcytosine, methyladenosine was also shown to have an effect on IPD over a range of several bases upstream and downstream of the position of the methyladenosine. Specifically, an increase in IPD was observed at some positions in the presence of methyladenosine relative to the same position in the absence of methyladenosine. FIG. 15 provides a plot depicting the ratio of the average IPD in the methylated template to the average IPD in the unmethylated template, plotted versus DNA template position. The two templates are identical except for the methylated bases in the methylated template, which are indicated by arrowheads in FIG. 15.

Detection of 5-hydroxymethylcytosine

Figure 16:
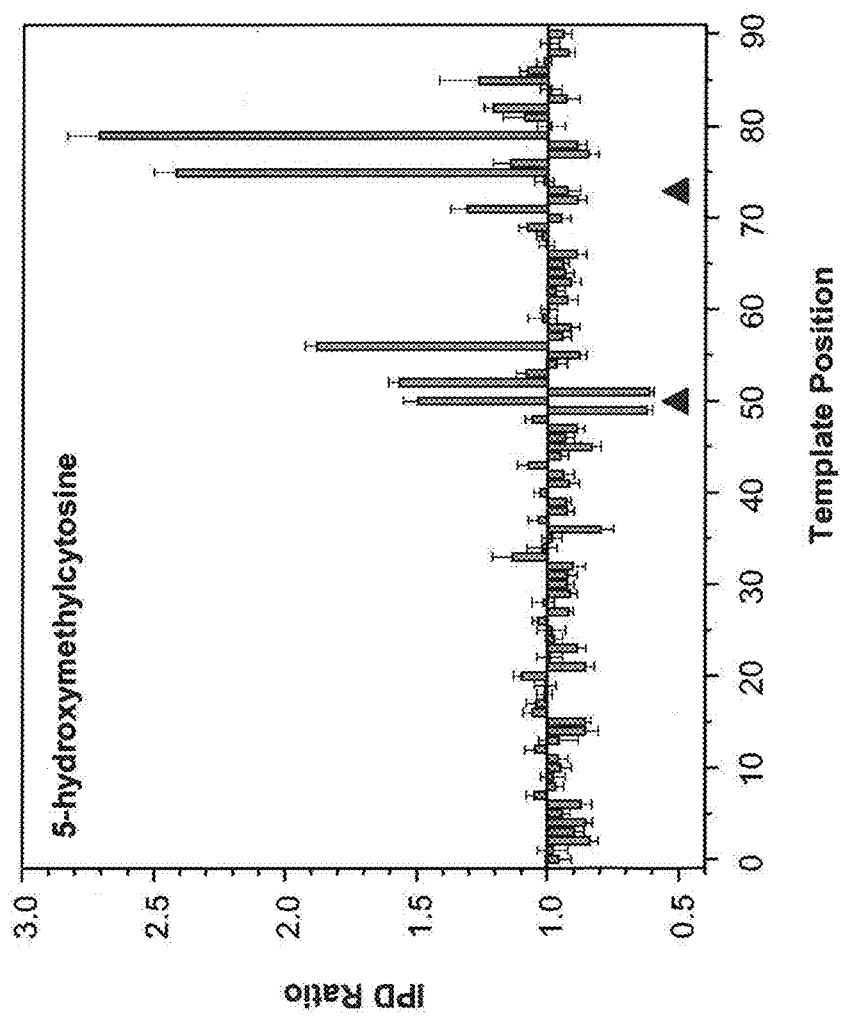
FIG. 16 provides a graph plotting IPD ratio against template position for a template nucleic acid comprising 5-hydroxymethylcytosine modifications.
Figure 17:
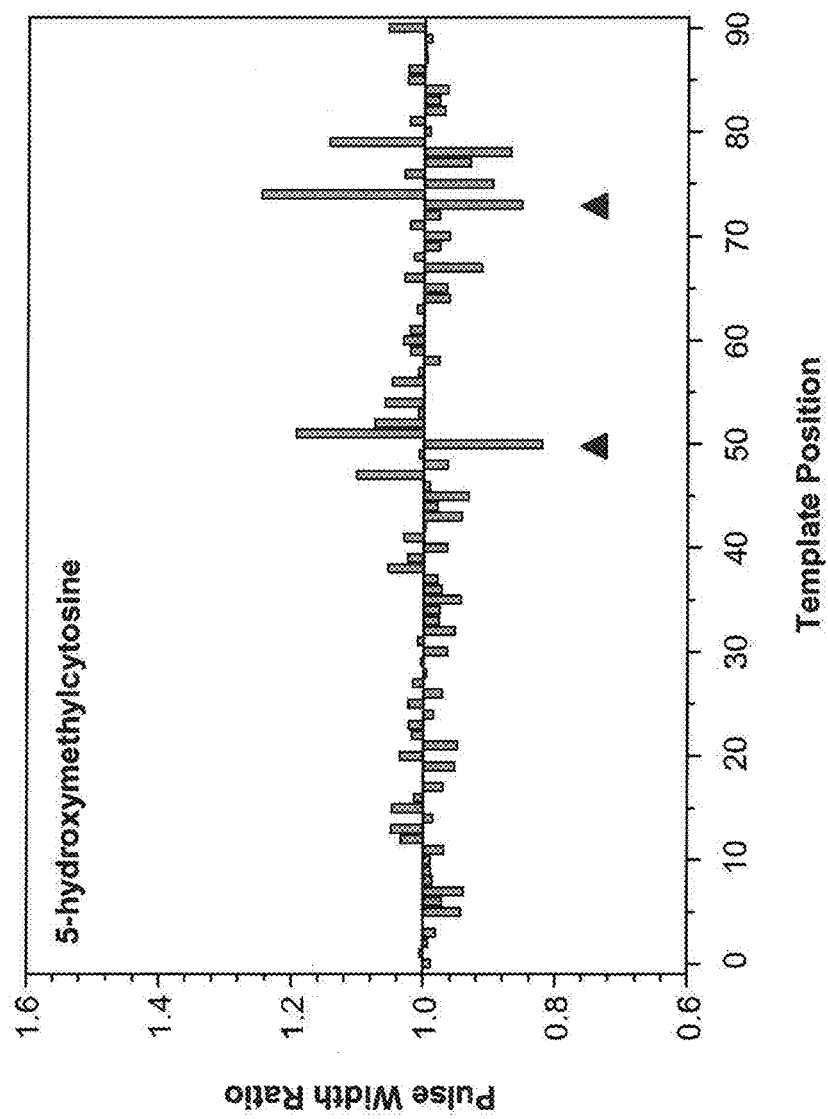
FIG. 17 provides a graph plotting pulse width ratio against template position for a template nucleic acid comprising 5-hydroxymethylcytosine modifications.

Similar to 5-MeC and $N^6$-MeA, 5-hydroxymethylcytosine was also tested and shown to have an effect on IPD over a range of several bases upstream and downstream of the position of the 5-hydroxymethylcytosine. Specifically, an increase in IPD was observed at some positions in the presence of 5-hydroxymethylcytosine relative to the same position in the absence of 5-hydroxymethylcytosine. FIG. 16 provides a plot depicting the ratio of the average IPD in the hydroxymethylated template to the average IPD in the unmethylated template, plotted versus DNA template position. The two templates are identical except for the hydroxymethylcytosine in the hydroxymethylated template, which are indicated by arrowheads in FIG. 16. Templates comprising 5-hydroxymethylcytosine bases were also tested and the presence of these modifications was shown to have an effect on pulse width. FIG. 17 provides a plot of pulse width ratio (pulse width for methylated template divided by pulse width for unmethylated template) vs. template position where the modified positions comprise 5-hydroxymethylcytosine bases. Variably hydroxymethylated positions are indicated by the arrowheads.

Detection of 8-oxoguanosine (8-oxoG)

Figure 18:
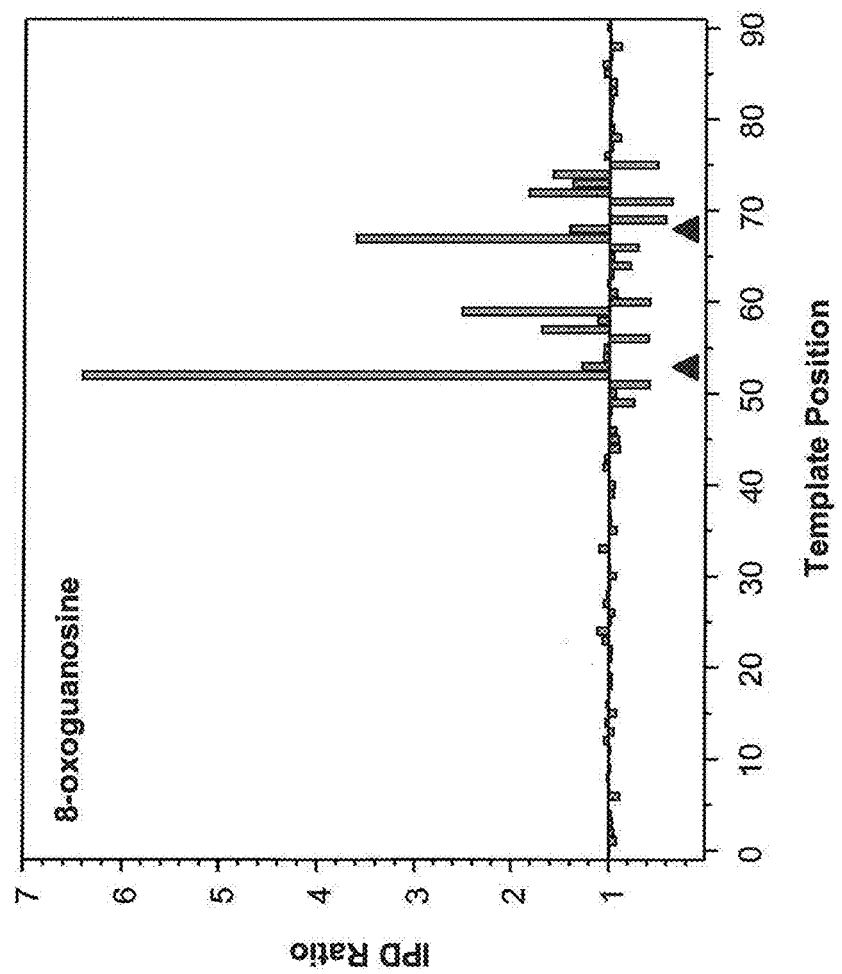
FIG. 18 provides a graph plotting IPD ratio against template position for a template nucleic acid comprising 8-oxoguanosine modifications.
Figure 19:
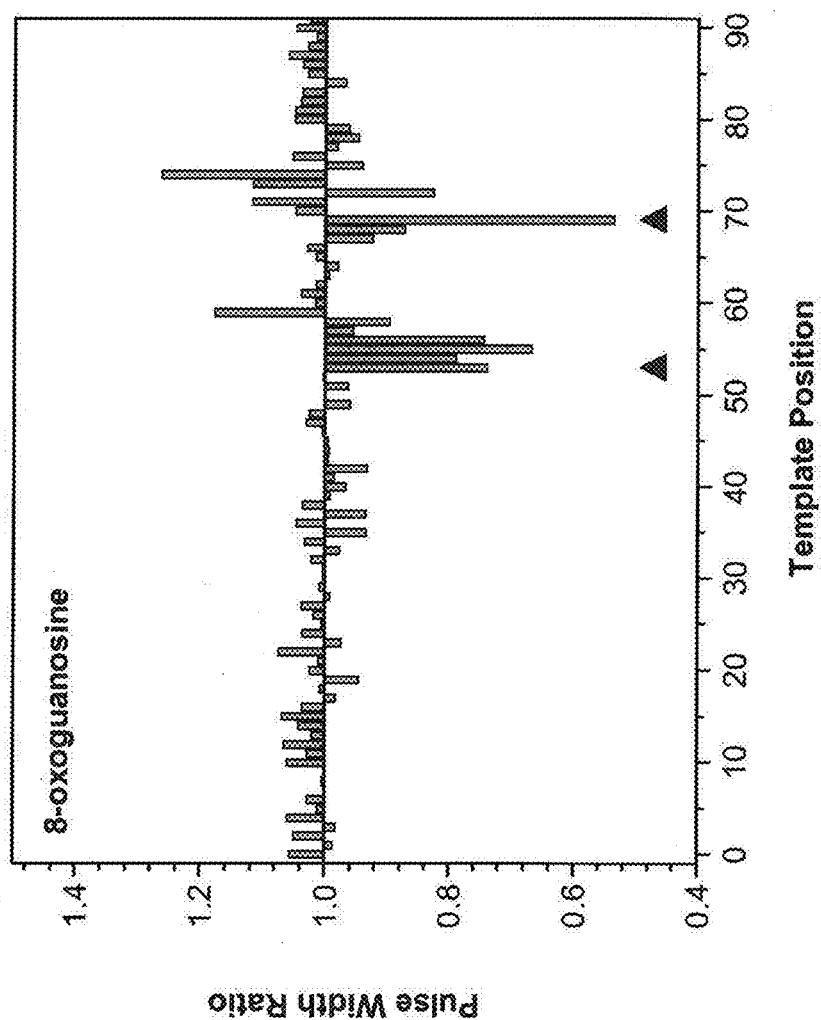
FIG. 19 provides a graph plotting pulse width ratio against template position for a template nucleic acid comprising 8-oxoguanosine modifications.
Figure 21:
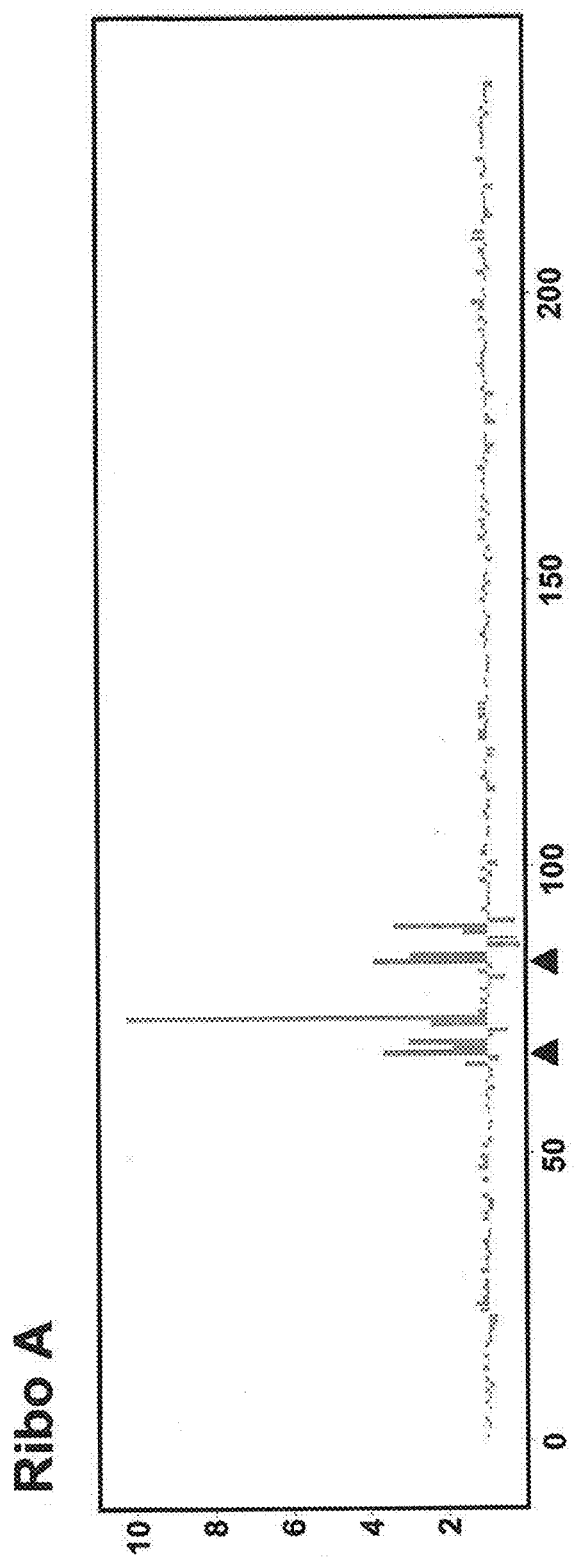
FIG. 21 provides a graph plotting IPD ratio against template position for a template deoxyribonucleic acid comprising adenosine ribonucleosides.
Figure 22:
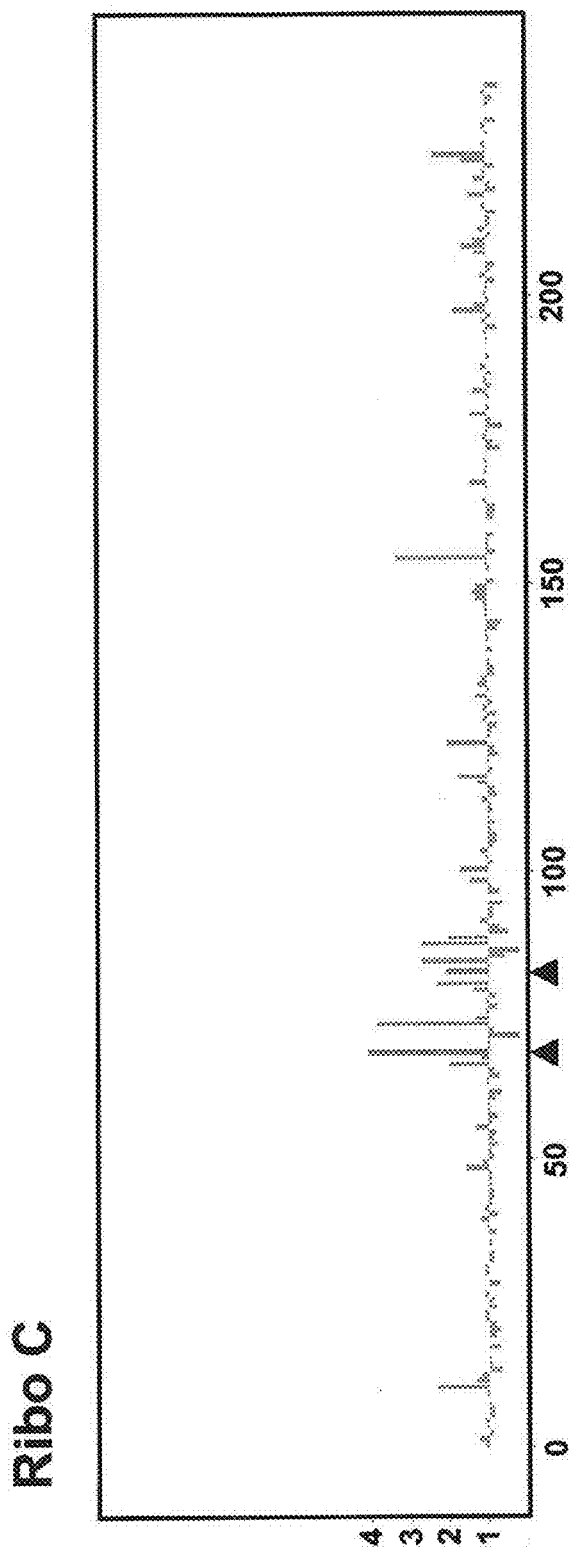
FIG. 22 provides a graph plotting IPD ratio against template position for a template deoxyribonucleic acid comprising cytidine ribonucleosides.
Figure 23:
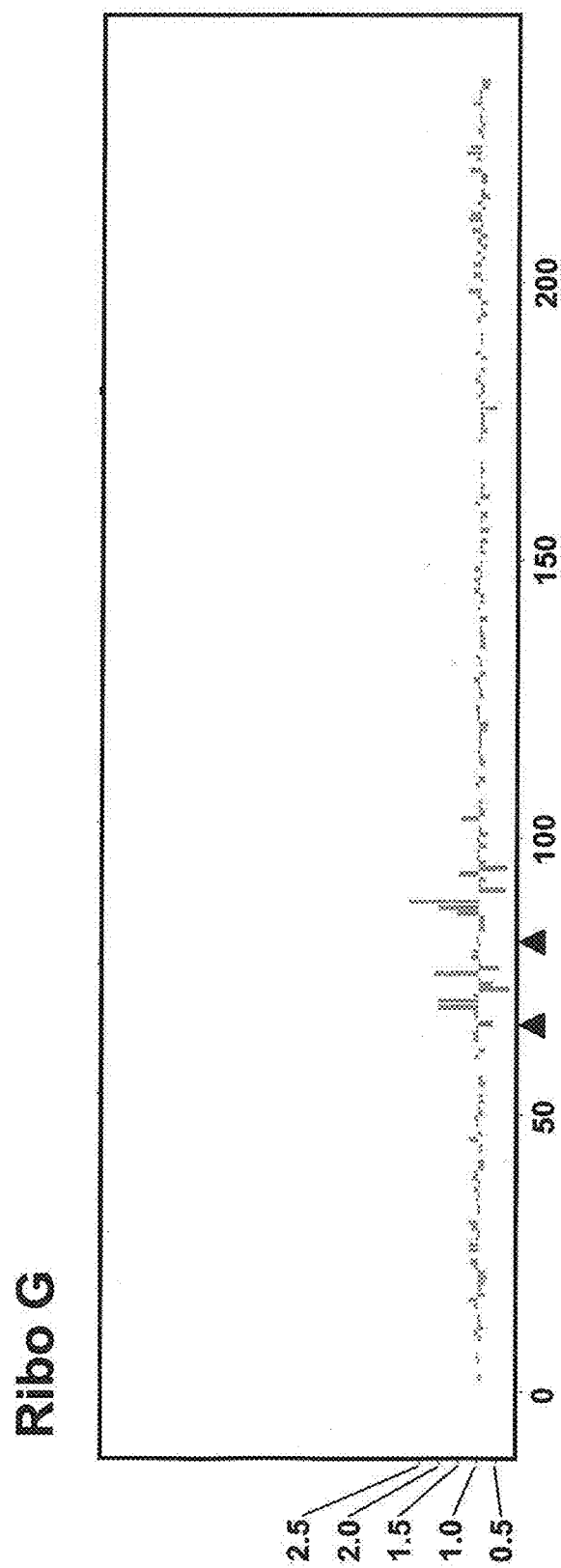
FIG. 23 provides a graph plotting IPD ratio against template position for a template deoxyribonucleic acid comprising guanosine ribonucleosides.
Figure 24:
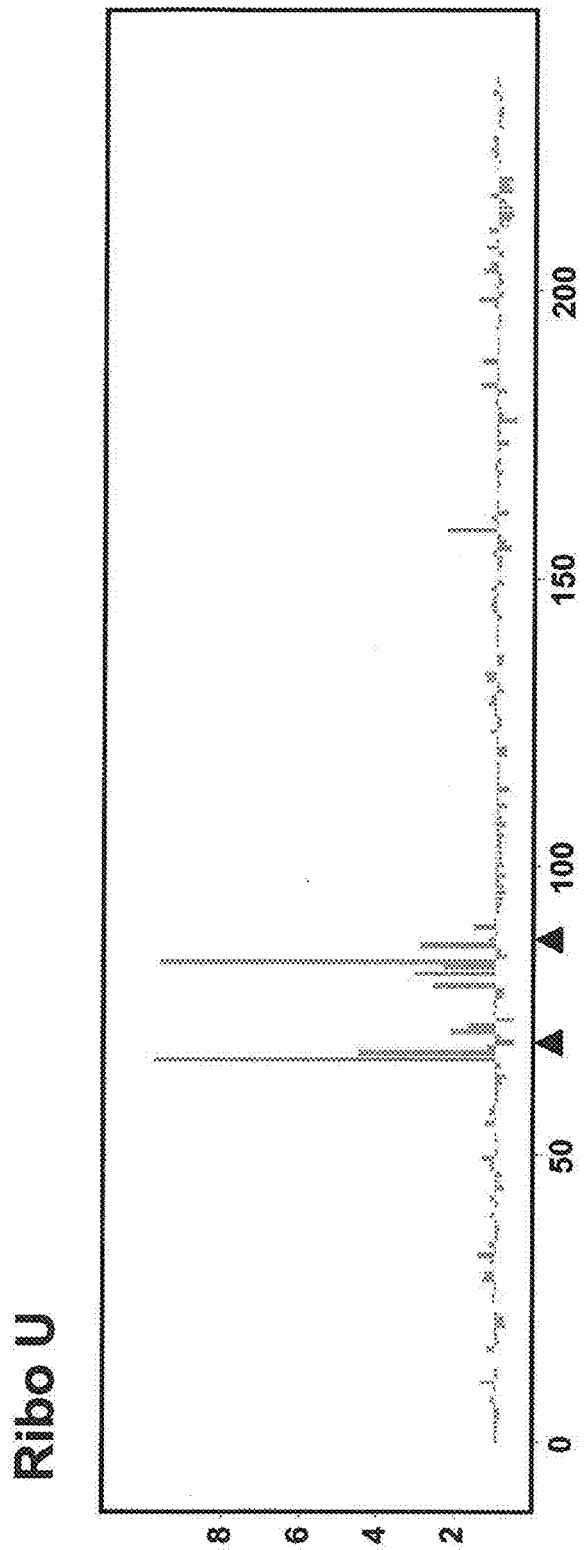
FIG. 24 provides a graph plotting IPD ratio against template position for a template deoxyribonucleic acid comprising uridine ribonucleosides.

8-oxoguanosine was also subjected to single molecule real-time sequencing and was shown to affect IPD both at the site of the modifications as well as at proximal unmodified positions in the template. An increase in IPD was observed at some positions in the presence of 8-oxoguanosine relative to the same position in the absence of 8-oxoguanosine. FIG. 18 provides a plot depicting the ratio of the average IPD in the 8-oxoguanosine template to the average IPD in the unmodified template, plotted versus DNA template position. The two templates are identical except for the 8-oxoguanosine in the modified template, which are indicated by arrowheads in FIG. 18. These data showed that, compared to G, 8-oxoG altered IPD significantly over a window of ~10 neighboring bases surrounding the 8-oxoG position. Some positions saw an increase in IPD by a factor of as much as 6.5×. Templates comprising 8-oxoG bases were also tested and the presence of these modifications was shown to have an effect on pulse width. FIG. 19 provides a plot of pulse width ratio (pulse width for an 8-oxoG template divided by pulse width for template with no 8-oxoG) vs. template position where the modified positions comprise 8-oxoG bases. Variable positions are indicated by the arrowheads. Further, 8-oxoG altered pulse width over a window of 7-8 neighboring bases by as much as 40%, and such alteration included both increases and decreases in pulse width.

Detection of Ribonucleosides within DNA

The presence of ribonucleotides within DNA has recently been shown in yeast, e.g., in Nick McElhinny, et al. (2010) Proc. Natl. Acad. Sci. USA 107(10:4949-4954; Nick McElhinny, et al. (2010) Nat. Chem. Biol. 6(10):774-781, the disclosures of which are incorporated herein by reference in their entireties for all purposes. At least one functionally significant role for ribonucleosides within DNA is known, namely in yeast mate pair switching. They also represent potential sites of genomic instability. Conventional sequencing methods are not generally capable of distinguishing deoxyribonucleotides from ribonucleotides, e.g., dA from rA, dC from rC, etc. In contrast, the methods provided here in are able to distinguish deoxyribonucleotides from ribonucleotides within a template nucleic acid molecule. Closed circular DNA templates were constructed comprising the sequences provided in FIG. 20 within a double-stranded portion (comprising two complementary oligonucleotides ordered from Integrated DNA Technologies) flanked by two hairpin or stem-loop structures using methods described elsewhere herein and in Flusberg, et al. (2010) Nature Methods 7:461-465, incorporated herein by reference in its entirety for all purposes. The templates are identical except for the two adenosines, cytidines, uridines, or guanosines in the modified Ribo A, Ribo C, Ribo U, and Ribo G templates, respectively. The templates were subjected to single molecule real-time sequencing, and the presence of ribonucleosides was shown to affect IPD both at the site of the modifications as well as at proximal unmodified positions in the template. An increase in IPD was observed at some positions in the presence of a ribonucleoside relative to the same position in the absence of the ribonucleoside in the control template. FIGS. 21, 22, 23, and 24 provide plots depicting the ratio of the average IPD in the Ribo A, Ribo C, Ribo G, and Ribo U templates, respectively, to the average IPD in the control template, plotted versus DNA template position. The ribonucleosides in the modified templates are indicated by arrowheads in FIGS. 21-24. These data showed that, compared to deoxyribonucleoside, a ribonucleoside altered IPD significantly over a window of ~10 neighboring bases surrounding the modified position. Some positions saw an increase in IPD by a factor of as much as 6.5×.

Detection of Glucose-Modified 5-hydroxymethylcytosine

Figure 25:
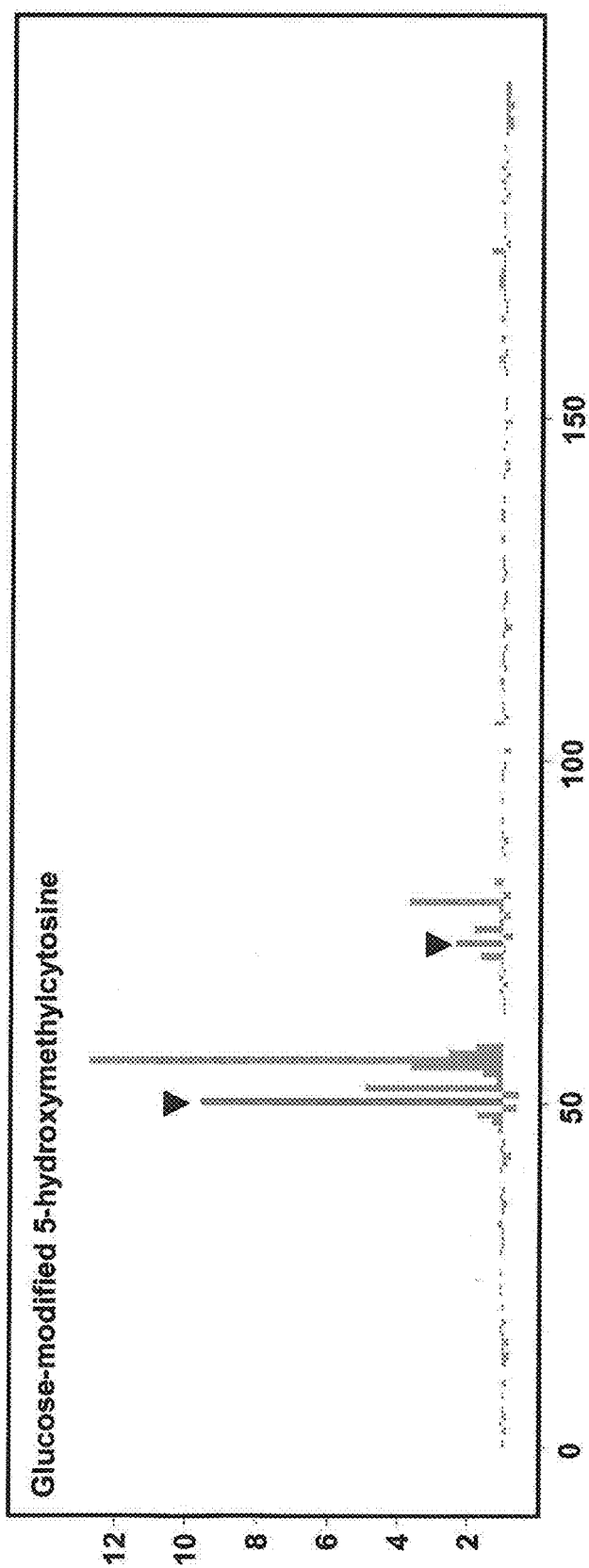
FIG. 25 provides a graph plotting IPD ratio against template position for a template deoxyribonucleic acid comprising glucose-modified 5-hydroxymethylcytosine.

Glucose-modified 5-hydroxymethylcytosine was also tested and shown to have an effect on IPD over a range of several bases upstream and downstream of the position of the glucose-modified 5-hydroxymethylcytosine. Closed, circular single-stranded templates were constructed containing a synthetic template containing two hmC residues in a duplex region flanked by single stranded linkers. Two micrograms of this template was labeled with a glucose moiety using T4 phage β-glucosyltransferase (New England Biolabs, Inc.). The samples were incubated at 37° C. for 60 minutes in the presence of 40 µM UDP-glucose following the manufacturer's recommendation. The resulting samples were cleaned up using a QIAGEN PCR Purification column and sequenced using previously described methods (Flusberg, et al. (2010) Nature Methods 7:461-465). An increase in IPD was observed at some positions in the presence of glucose-modified 5-hydroxymethylcytosine relative to the same positions in the absence of glucose-modified 5-hydroxymethylcytosine. FIG. 25 provides a plot depicting the ratio of the average IPD in the glucose-modified template to the average IPD in the unmodified template, plotted versus DNA template position. The two templates are identical except for the glucose-modified hydroxymethylcytosines in the modified template, which are indicated by arrowheads in FIG. 25. Average IPD ratios for glucose-modified hydroxymethylcytosine increased by as much as five-fold relative to detection of unmodified hydroxymethylcytosine (FIG. 16.)

Detection of Modified Bases in RNA Templates

Figure 26:
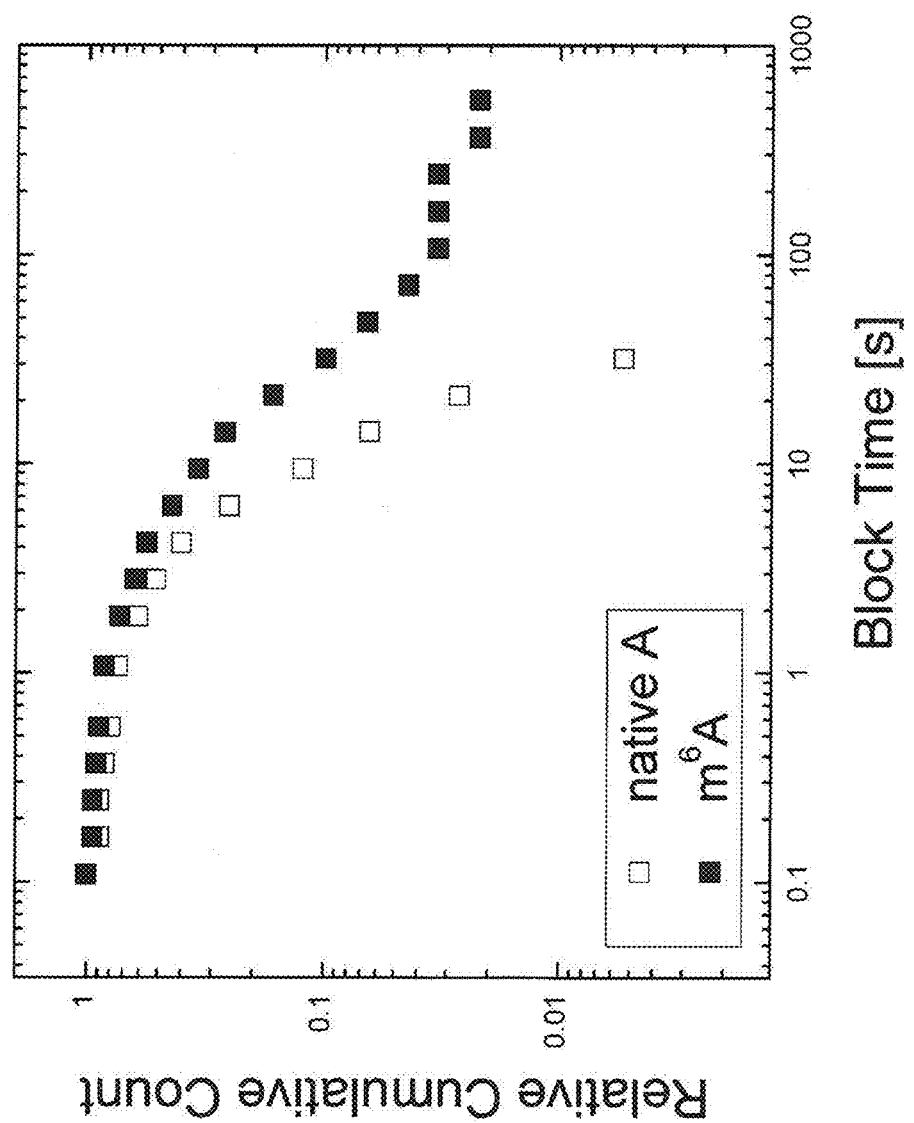
FIG. 26 provides a graph plotting block times for a template ribonucleic acid comprising $N^6$-methyladenosine and a template ribonucleic acid lacking $N^6$-methyladenosine.

As noted elsewhere herein, the methods described herein can also be used for detection of modified nucleotides in RNA templates during template-dependent RNA sequencing. $N^6$-methyladenosine is a common post-translational modification of cellular and viral RNAs. RNA templates containing $N^6$-methyladenosine modifications at defined positions were produced by solid-phase nucleic acid synthesis. In addition, control RNA templates with identical sequences were synthesized without the above-mentioned modification. All RNA oligomers were hybridized to a complementary DNA primer that had been previously biotinylated at its 5'-end. Each DNA primer-RNA template hybrid was then immobilized via a biotin-streptavidin linkage in a ZMW. Single-molecule real-time RNA sequencing (as described in U.S. patent application Ser. No. 12/767,673, filed Apr. 26, 2010, and incorporated herein by reference in its entirety for all purposes) was initiated by the addition of reverse transcriptase under the following reaction conditions: 50 mM Tris pH 8.25, 10 mM KCl, 5 mM DDT, 0.1 mM $CaCl_2$, 2.5 mM $MgCl_2$, and 0.05 mM EGTA at 25° C. The kinetics of incorporation of complementary bases across from the modified site was evaluated and compared to the same sequence context lacking the modification. In these RNA sequencing reactions, base incorporations are detected as a combination of pulses of cognate sampling and incorporation. A "block" is defined as part of a sequencing trace containing pulses of the same base, indicating at least one of that base was incorporated into the nascent strand. "Block time" is defined as the time from the start of the first pulse of a block to the end of the last pulse of that block. FIG. 26 provides a plot depicting the relative cumulative count of events relative to observed block time in the $N^6$-methyladenosine modified template (filled squares) and the unmodified template (open squares). This plot clearly shows that the $N^6$-methyladenosine bases generally exhibit substantially longer block times than do the unmodified adenosine bases, and they can be distinguished from one another during single-molecule, real-time RNA sequencing. Further, the pulses within each block are characterized by standard parameters, including interpulse duration. For example, the values for IPD are sensitive to the presence of $N^6$-methyladenosine modifications, e.g., the distances between individual pulses increase in the presence of this modification. These increased IPDs are reflected in a higher $K_{off}$ obtained from the distributions of IPDs shown in FIG. 27.

It is to be understood that the above description is intended to be illustrative and not restrictive. It readily should be apparent to one skilled in the art that various embodiments and—modifications may be made to the invention disclosed in this application without departing from the scope and spirit of the invention. The scope of the invention should, therefore, be determined not with reference to the above description, but should instead be determined with reference to the appended claims, along with the full scope of equivalents to which such claims are entitled. All publications mentioned herein are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications, and publications are referenced. To the extent not already expressly incorporated herein, all published references and patent documents referred to in this disclosure are incorporated herein by reference in their entirety for all purposes.

What is claimed is:

1. A method for enhancing identification of a modification of interest, the method comprising:
   a) providing a DNA template comprising the modification of interest, the modification of interest being characterized by a first kinetic signature during processing by a polymerase, wherein the modification of interest is a methylated base or a hydroxymethylated base;
   b) converting the modification of interest into a further modification, by subjecting the DNA template to a treatment to introduce the further modification, wherein the treatment comprises exposure to a modifying agent selected from the group consisting of a glycosylase, bisulfite, a hydroxylase, a glucosyltransferase, NMIA, and CDI, wherein the further modification is characterized by a second kinetic signature during processing by the polymerase, and further wherein the second kinetic signature is distinct from the first kinetic signature;
   c) providing the polymerase, which is capable of processing the DNA template;
   d) contacting the DNA template comprising the further modification with the polymerase;
   e) monitoring processing of the DNA template comprising the further modification by the polymerase; and
   f) detecting a change in the kinetics of the polymerase during the processing, wherein the change is indicative of the second kinetic signature, thereby detecting the further modification, and enhancing identification of the modification of interest that was present in the DNA template prior to the converting.

2. The method of claim 1, wherein the DNA template comprises two single-stranded portions and one double-stranded portion, wherein the two single-stranded portions are single-stranded hairpins.

3. The method of claim 1, wherein the DNA template comprises a first polynucleotide region comprising the modification of interest and a second polynucleotide region complementary to the first polynucleotide region, where the first polynucleotide region and the second polynucleotide region are on a single strand of the DNA template.

4. The method of claim 1, wherein the treatment comprises addition of a glucose moiety to a nucleobase comprising the modification of interest, wherein the change in the kinetics of the polymerase during the processing is greater than in the absence of the glucose moiety.

5. The method of claim 4, wherein the nucleobase is a hydroxymethylcytosine nucleobase, which is converted to β-glucosyl-5-hydroxymethylcytosine by the addition of the glucose moiety.

6. The method of claim 1, wherein the processing results in the synthesis of a nascent nucleic acid strand.

7. The method of claim 1, wherein the processing is a single-molecule sequencing reaction.

8. The method of claim 6, wherein the monitoring detects incorporation of single nucleotides into the nascent nucleic acid strand to generate a sequence read that is complementary to the DNA template.

9. The method of claim 8, wherein the change occurs at the further modification and at one or more positions upstream or downstream of the further modification.

10. The method of claim 8, further comprising mapping the modification of interest within the DNA template, the mapping comprising:
    a) analyzing a portion of the sequence read that was generated immediately prior to, during, or immediately after the detecting the change in kinetics to determine a sequence complementary to the DNA template;
    b) determining the complement of the sequence complementary to the DNA template in f; and
    c) mapping the modification of interest at a position in the DNA template that is proximal to the complement of the sequence complementary to the DNA template in f.

11. The method of claim 1, wherein the DNA template and the polymerase form a complex that is immobilized at a reaction site on a substrate.

12. The method of claim 1, wherein the DNA template is a plurality of DNA templates that are optically resolvable from one another during the monitoring.

13. The method of claim 1, wherein the second kinetic signature comprises kinetic changes in the polymerase at one or more positions upstream or downstream of the further modification.

14. The method of claim 1, wherein the DNA template further comprises a third modification, wherein the third modification is:
    (i) different from both the modification of interest and the further modification; and
    (ii) is characterized by a third kinetic signature during processing by the polymerase, wherein the third kinetic signature is distinct from both the first kinetic signature and the second kinetic signature;
    and further wherein said detecting comprises distinguishing between the further modification and the third modification during the processing based upon their kinetic signatures.

15. The method of claim 4, wherein the glucose moiety comprises a detectable label.

* * * * *

SEQUENCE LISTING

```
<160> NUMBER OF SEQ ID NOS: 6

<210> SEQ ID NO 1
<211> LENGTH: 44
<212> TYPE: DNA
<213> ORGANISM: Artificial Sequence
<220> FEATURE:
<223> OTHER INFORMATION: Ribo A template
```

```
<220> FEATURE:
<221> NAME/KEY: ribonucleotide
<222> LOCATION: (15)..(15)
<220> FEATURE:
<221> NAME/KEY: ribonucleotide
<222> LOCATION: (31)..(31)

<400> SEQUENCE: 1
ccagactcgg gcatacttga tcgaccatgc ataggcggaa caac          44

<210> SEQ ID NO 2
<211> LENGTH: 36
<212> TYPE: DNA
<213> ORGANISM: Artificial Sequence
<220> FEATURE:
<223> OTHER INFORMATION: Complement to Ribo A, C, U, and G templates;
      complement to Control template

<400> SEQUENCE: 2
ttccgcctat gcatggtcga tcaagtatgc ccgagt                   36

<210> SEQ ID NO 3
<211> LENGTH: 44
<212> TYPE: DNA
<213> ORGANISM: Artificial Sequence
<220> FEATURE:
<223> OTHER INFORMATION: Ribo C template
<220> FEATURE:
<221> NAME/KEY: ribonucleotide
<222> LOCATION: (16)..(16)
<220> FEATURE:
<221> NAME/KEY: ribonucleotide
<222> LOCATION: (30)..(30)

<400> SEQUENCE: 3
ccagactcgg gcatacttga tcgaccatgc ataggcggaa caac          44

<210> SEQ ID NO 4
<211> LENGTH: 44
<212> TYPE: DNA
<213> ORGANISM: Artificial Sequence
<220> FEATURE:
<223> OTHER INFORMATION: Ribo U template
<220> FEATURE:
<221> NAME/KEY: ribonucleotide
<222> LOCATION: (17)..(17)
<220> FEATURE:
<221> NAME/KEY: ribonucleotide
<222> LOCATION: (32)..(32)

<400> SEQUENCE: 4
ccagactcgg gcatacutga tcgaccatgc auaggcggaa caac          44

<210> SEQ ID NO 5
<211> LENGTH: 44
<212> TYPE: DNA
<213> ORGANISM: Artificial Sequence
<220> FEATURE:
<223> OTHER INFORMATION: Ribo G template
<220> FEATURE:
<221> NAME/KEY: ribonucleotide
<222> LOCATION: (11)..(11)
<220> FEATURE:
<221> NAME/KEY: ribonucleotide
<222> LOCATION: (29)..(29)

<400> SEQUENCE: 5
ccagactcgg gcatacttga tcgaccatgc ataggcggaa caac          44
```

```
<210> SEQ ID NO 6
<211> LENGTH: 44
<212> TYPE: DNA
<213> ORGANISM: Artificial Sequence
<220> FEATURE:
<223> OTHER INFORMATION: Control template

<400> SEQUENCE: 6
ccagactcgg gcatacttga tcgaccatgc ataggcggaa caac                    44
```